US011786610B2

(12) United States Patent
Lockhart et al.

(10) Patent No.: US 11,786,610 B2
(45) Date of Patent: Oct. 17, 2023

(54) TREATMENT OF PRIMARY CILIARY DYSKINESIA WITH SYNTHETIC MESSENGER RNA

(71) Applicant: TranscripTx, Inc., Sunnyvale, CA (US)

(72) Inventors: David J. Lockhart, Redwood City, CA (US); Brandon Wustman, San Diego, CA (US); Mirko Hennig, Sunnyvale, CA (US); Daniella Ishimaru, Sunnyvale, CA (US)

(73) Assignee: TranscripTx, Inc., Menlo Park, CA (US)

( * ) Notice: Subject to any disclaimer, the term of this patent is extended or adjusted under 35 U.S.C. 154(b) by 0 days.

(21) Appl. No.: 18/048,253

(22) Filed: Oct. 20, 2022

(65) Prior Publication Data

US 2023/0190957 A1    Jun. 22, 2023

Related U.S. Application Data

(63) Continuation of application No. 16/941,028, filed on Jul. 28, 2020, which is a continuation of application No. 16/192,622, filed on Nov. 15, 2018, now abandoned, which is a continuation of application No. PCT/US2017/034723, filed on May 26, 2017.

(60) Provisional application No. 62/342,784, filed on May 27, 2016.

(51) Int. Cl.
| | | |
|---|---|---|
| *A61K 48/00* | (2006.01) | |
| *A61P 11/00* | (2006.01) | |
| *A61P 11/06* | (2006.01) | |
| *A61K 9/127* | (2006.01) | |
| *A61K 31/7105* | (2006.01) | |
| *A61K 31/7115* | (2006.01) | |
| *C12N 15/113* | (2010.01) | |
| *A61K 47/69* | (2017.01) | |

(52) U.S. Cl.
CPC ......... *A61K 48/005* (2013.01); *A61K 9/1271* (2013.01); *A61K 31/7105* (2013.01); *A61K 31/7115* (2013.01); *A61K 47/6925* (2017.08); *A61K 48/0041* (2013.01); *A61P 11/00* (2018.01); *A61P 11/06* (2018.01); *C12N 15/113* (2013.01)

(58) Field of Classification Search
None
See application file for complete search history.

(56) References Cited

U.S. PATENT DOCUMENTS

| | | | |
|---|---|---|---|
| 8,450,298 B2 | 5/2013 | Mahon et al. | |
| 9,023,821 B2 | 5/2015 | Marcet et al. | |
| 9,061,059 B2 | 6/2015 | Chakraborty et al. | |
| 11,078,247 B2 | 8/2021 | Fotin-Mleczek et al. | |
| 11,510,997 B2 | 11/2022 | Lockhart et al. | |
| 2014/0010861 A1 | 1/2014 | Bancel et al. | |
| 2015/0126589 A1* | 5/2015 | Geiger | A61P 43/00 514/44 R |
| 2018/0126003 A1 | 5/2018 | Hoerr | |
| 2019/0111074 A1 | 4/2019 | Lockhart et al. | |
| 2019/0117796 A1 | 4/2019 | Lockhart et al. | |
| 2019/0241633 A1* | 8/2019 | Fotin-Mleczek | A61K 31/7088 |
| 2020/0215157 A1* | 7/2020 | Dias | A61K 31/7105 |
| 2021/0162068 A1 | 6/2021 | Lockhart et al. | |

FOREIGN PATENT DOCUMENTS

| | | | |
|---|---|---|---|
| CN | 101104853 A | 1/2008 | |
| CN | 104120133 A | 10/2014 | |
| CN | 104936977 A | 9/2015 | |
| EP | 3463483 A1 | 4/2019 | |
| JP | 2015516143 A | 6/2015 | |
| JP | 2015535430 A | 12/2015 | |
| JP | 2017121243 A | 7/2017 | |
| WO | WO-2006138380 A2 | 12/2006 | |
| WO | WO-2009154790 A2 * | 12/2009 | ........... C12Q 1/6886 |
| WO | WO-2013151665 A2 | 10/2013 | |
| WO | WO-2017205767 A1 | 11/2017 | |
| WO | WO-2019161459 A1 | 8/2019 | |
| WO | WO-2020051220 A1 | 3/2020 | |
| WO | WO-2020051223 A1 | 3/2020 | |
| WO | WO-2020146344 A1 | 7/2020 | |
| WO | WO-2020165352 A1 | 8/2020 | |
| WO | WO-2022198099 A1 | 9/2022 | |
| WO | WO-2022204215 A1 | 9/2022 | |

OTHER PUBLICATIONS

Merveille et al. Nature Genetics 43, 72-78 (Year: 2011).*
Becker-Heck et al. Nature Genetics 43, 79-85 (Year: 2011).*
Akinc, A. et al., A combinatorial library of lipid-like materials for delivery of RNAi therapeutics. Nature Biotechnology 26(5):561-569 (May 2008). Published online Apr. 27, 2008. DOI: 10.1038/nbt1402.
Akinc, A. et al., Development of lipidoid-siRNA formulations for systemic delivery to the liver. Molecular Therapy 17(5):872-879 (2009).
Chhin et al: "Ciliary Beating Recovery in Deficient Human Airway Epithelial Cells after Lentivirus Ex Vivo Gene Therapy", Plos Genetics, vol. 5, No. 3, Mar. 20, 2009 (Mar. 20, 2009), p. e1000422, XP055444805, DOI: 10.1371 / journal.pgen.1000422.
EP17803679.4 Extended European Search Report dated Nov. 19, 2019.

(Continued)

*Primary Examiner* — Brian Whiteman
(74) *Attorney, Agent, or Firm* — Wilson Sonsini Goodrich & Rosati

(57) ABSTRACT

Polynucleotides encoding peptides, proteins, enzymes, and functional fragments thereof are disclosed. The polynucleotides of the disclosure can be effectively delivered to an organ, such as the lung, and expressed within cells of the organ. The polyribonucleotides of the disclosure can be used to treat a disease or condition associated with cilia maintenance and function, impaired function of the axoneme, such as DNAI1 or DNAH5.

20 Claims, 32 Drawing Sheets

Specification includes a Sequence Listing.

(56) References Cited

OTHER PUBLICATIONS

Geremek, M. et al., Ciliary genes are down-regulated in bronchial tissue 49-50of primary ciliary dyskinesia patients, PLOS One, 2014, vol. 9, Issue 2, Artice No. e88216, Internal pp. 1-8.
Guevara, M. L. et al., Advances in lipid nanoparticles for mRNA-based cancer immunotherapy, Frontiers in chemistry, Review article, Oct. 23, 2020, vol. 8, article No. 589959, pp. 1-17.
Guichard, C. et al., 'Axonemal dynein intermediate-chain gene (DNAiI)mutations result in situs Inversus and primary ciliary dyskinesia (kartagenersyndrome)' The American Journal of Human Genetics, 2001, vol. 68, pp. 1030-1035.
Hom et al. A Unified taxonomy for ciliary Dyneins. Cytoskeleton. Oct. 2011; 68:555-65 (Year: 2011).
JP2015516143-A/44400: Modified Polynucleotides for the Production Ofproteins Associated With Human Disease: Genbank Jun. 8, 2015.
Love et al. Lipid-like materials for low-dose, in vivo gene silencing. PNAS 107(5):1864-1869 (Feb. 2, 2010). DOI: https://doi.org/10.1073/pnas.0910603106. Correction for article, PNAS 107(21):9915 (May 25, 2010). DOI: https://doi.org/10.1073/pnas.0910603106.
Ostrowski, L. E. et al., Restoring ciliary function to differentiated 29-44,51-55,57primary ciliary dyskinesia cells with a lentiviral vector, Gene Therapy, 2014, vol. 21, No. 3, pp. 253-261.
PCT/US2017/034723 International Search Report and Written Opinion dated Sep. 8, 2017.
PCT/US2022/021032 International Search Report dated Aug. 11, 2022.
PCT/US2022/021032 Written Opinion of the International Searching Authority dated Aug. 11, 2022.
PCT/US2022/021437 International Search Report dated Aug. 8, 2022.
PCT/US2022/021437 Written Opinion of the International Searching Authority dated Aug. 8, 2022.
Pennarun et al., Loss-of-Function Mutations in a Human Gene Related to Chlamydomonas reinhardtii Dynein IC78 Result in Primary Ciliary Dyskinesia. American Journal of Human Genetics 65: 1508-1519 (Year: 1999).
Pfeifer et al.: Efficient, specific and targeted delivery of genes to the lung. Ther Deliv. 1(1):133-148 doi:10.4155/tde.10.11 (2010).
Primary Ciliary Dyskinesia, National Heart, Lung, and Blood Institute, pp. 1-12, retrieved on-line Jan. 13, 20 from https://www.nhlbi.nih.gov/print/4932 (year:2020).
U.S. Appl. No. 16/192,622 Office Action dated Jan. 29, 2020.
U.S. Appl. No. 16/192,661 Office Action dated Jan. 28, 2020.
U.S. Appl. No. 16/941,028 Notice of Allowance dated Nov. 9, 2022.
U.S. Appl. No. 16/941,028 Office Action dated Jun. 10, 2022.
U.S. Appl. No. 17/668,346 Notice of Allowance dated Aug. 2, 2022.
U.S. Appl. No. 17/668,346 Notice of Allowance dated Jul. 13, 2022.
U.S. Appl. No. 17/668,346 Office Action dated May 2, 2022.
Wolff et al. Direct gene transfer into mouse muscle in vivo. Science 247:1465-1468 (1990).
WXPress Disease-modifying RNA therapies from Recode Therapeutics Target Rare Lung Disease retrieved on line Apr. 25, 2022, from https://wxpress.wuxiapptec.com/disease-modifying-ma-therapies-from-recode-therapeutics-target-rare-lung-diseases, pp. 1-11 (Year: 2020).
Zariwala, M.A., et al: "Primary Ciliary Dyskinesia, Synonym: Immotile Cilia Syndrome", GeneReviews [Internet], Sep. 3, 2015 (Sep. 3, 2015), pp. 1993-2019, XP055638744, Retrieved from the Internet: URL:https://www.ncbi.nlm.nih.gov/books/NBK1122/pdf/Bookshelf NBK1122.pdf.
Zhou et al., "Modular degradable dendrimers enable small RNAs to extend survival in an aggressive liver cancer model," PNAS, 113(3):520-525, 2016.
U.S. Appl. No. 16/941,028 Notice of Allowance dated Feb. 9, 2023.

* cited by examiner

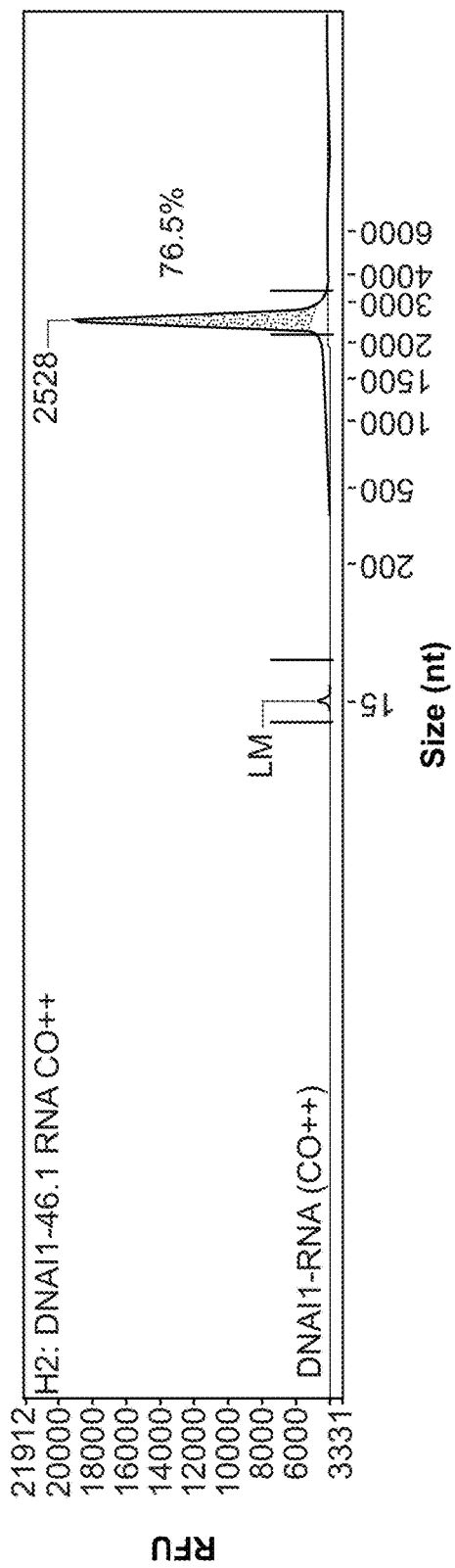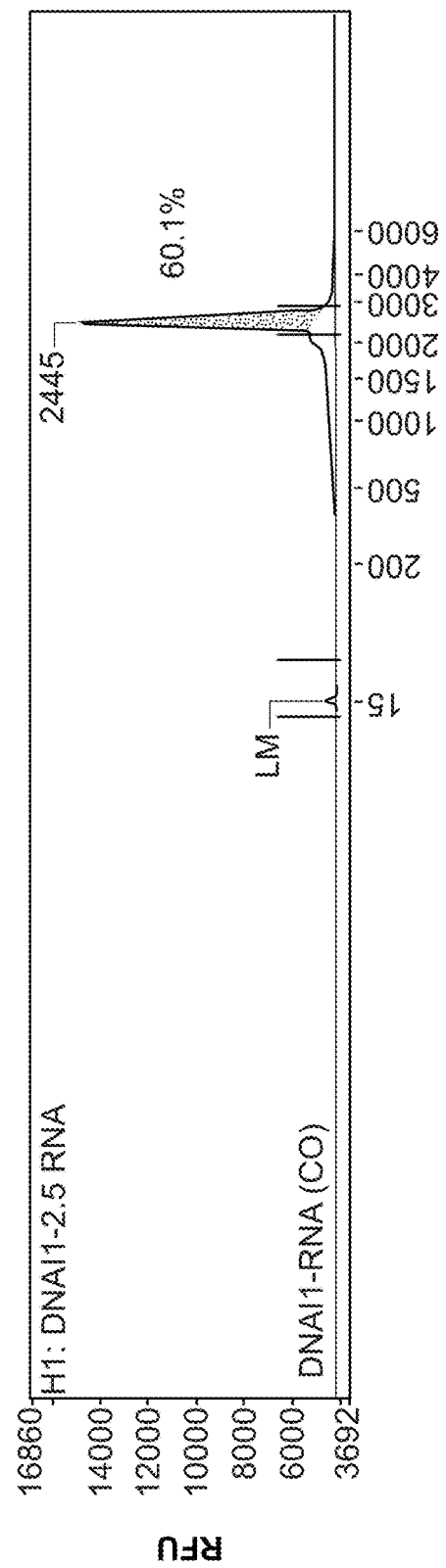
FIGURE 26A
FIGURE 26B

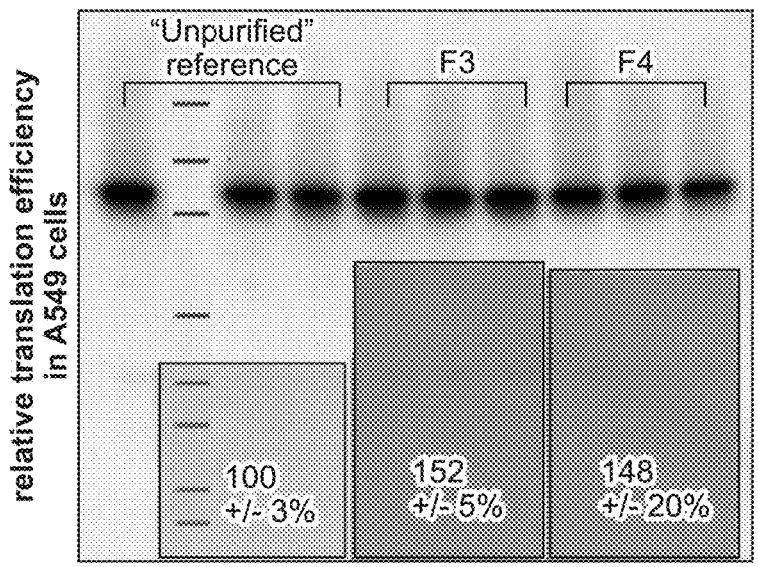
FIGURE 30C
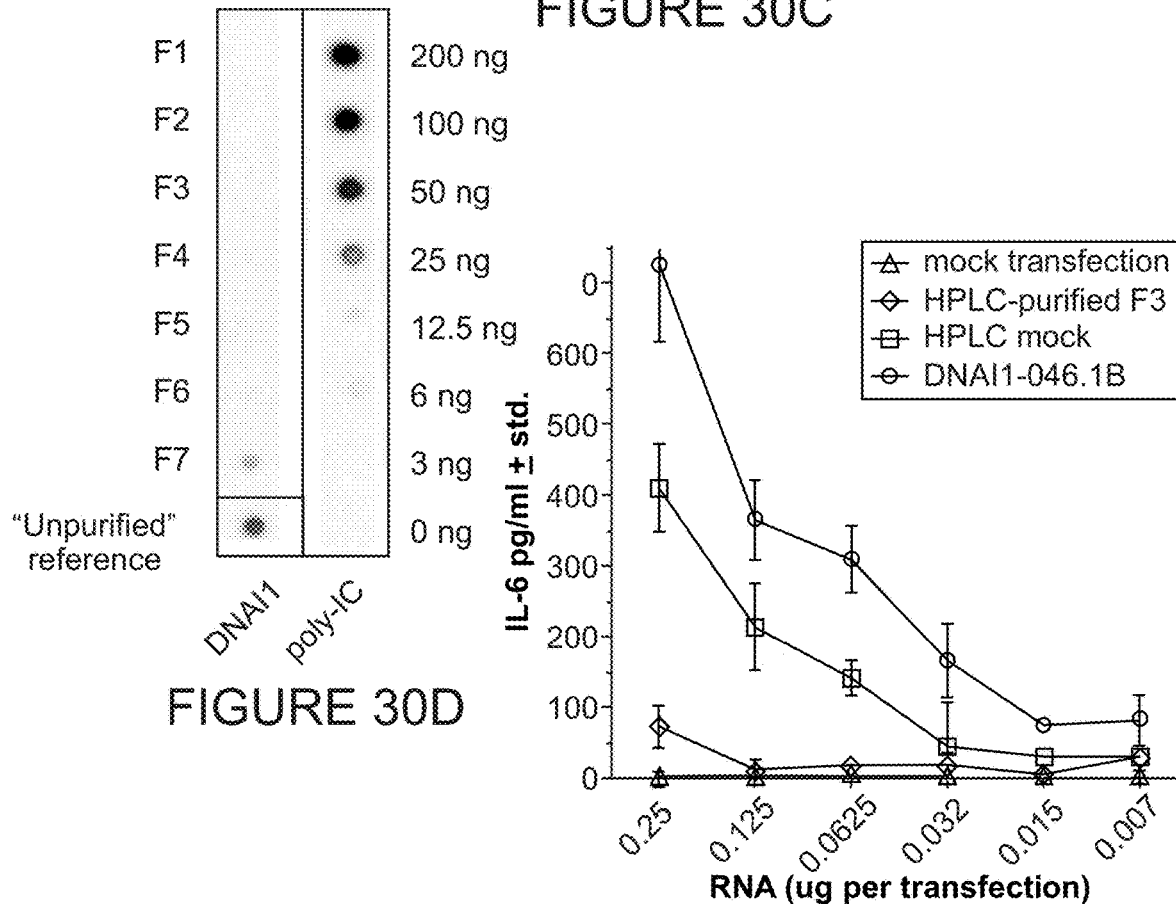
FIGURE 30D
FIGURE 30E

TREATMENT OF PRIMARY CILIARY DYSKINESIA WITH SYNTHETIC MESSENGER RNA

CROSS-REFERENCE

This application is a continuation application of U.S. Non-Provisional patent application Ser. No. 16/941,028, filed Jul. 28, 2020, which is a continuation application of U.S. Non-Provisional patent application Ser. No. 16/192,622, filed Nov. 15, 2018, which is a continuation of International Application No. PCT/US2017/034723, filed May 26, 2017, which claims priority to U.S. Provisional Patent Application Ser. No. 62/342,784, filed on May 27, 2016, all of which are incorporated herein by reference in their entireties for all purposes.

SEQUENCE LISTING

The instant application contains a Sequence Listing which has been submitted electronically in XML format and is hereby incorporated by reference in its entirety. Said XML copy, created on Oct. 19, 2022, is named 58530_708_305_SL.xml and is 62,695 bytes in size.

BACKGROUND

Messenger RNAs (mRNA) are polymers containing a number of linked nucleotides, each composed of a sugar, a phosphate, and a base. Each mRNA polymer stores genetic information along the nucleotide chain. Messenger RNA polymers carry the genetic information from the DNA in the nucleus of the cell to the cytoplasm where proteins are made. Each triplet of nucleotides in the mRNA is called a codon, and each codon specifies the identity of an amino acid in the translated protein.

A cell can also take up and translate an exogenous RNA, but many factors influence efficient uptake and translation. For instance, the immune system recognizes many exogenous RNAs as foreign and triggers a response that is aimed at inactivating the RNAs.

SUMMARY

The present disclosure provides polyribonucleotides, and compositions comprising the same, that can encode a protein of choice. In some cases, the disclosure provides a method for treating a subject having or at risk of having primary ciliary dyskinesia, the method comprising administrating to the subject a composition that comprises a nucleic acid construct that encodes dynein axonemal intermediate chain 1 protein or a variant thereof, which nucleic acid construct includes codons that provide for heterologous or enhanced expression of the dynein axonemal intermediate chain 1 protein or a variant thereof within cells of the subject, thereby treating the subject having or at risk of having primary ciliary dyskinesia. The nucleic acid construct can be, for example a complementary deoxyribonucleic acid DNA template. The nucleic acid construct may encode dynein axonemal intermediate chain 1 protein or a variant thereof at a level that is increased by a factor of at least about 1.5, at least about 5, or another suitable amount as compared to levels within cells exposed to a composition comprising a nucleic acid construct that does not include the codons encoding dynein axonemal intermediate chain 1 protein or a variant thereof. In some instances, the codons of the construct are at least 70% homologous to a mammalian, such as a human, dynein axonemal intermediate chain 1 mRNA.

In some cases, the construct comprises a 5' and/or 3' untranslated region (UTR) flanking the codon sequence which encodes the dynein axonemal intermediate chain 1, wherein the untranslated region(s) enhance(s) the expression of the protein within cells of the subject. The 3' noncoding region may comprise a 3'-cap independent translation enhancer (3'-CITEs). In some instances, the 3' noncoding region may also comprise at least one intermediate sequence region between the codon sequence and either the 3' noncoding region or the 5' noncoding region or a 3'-stem loop region derived from the nucleotide sequence of a histone protein. In some cases, the codon sequence comprises an open reading frame (ORF). The 3' noncoding region flanking the codon sequence (e.g., ORF) may comprise a poly adenosine tail, wherein the number of adenosines in the poly adenosine tail improves the translation efficiency and increases the half-life of the dynein axonemal intermediate chain 1 mRNA. In some cases, the length of the poly adenosine tail is at most 200 adenosines. The poly adenosine tail may comprise a percentage of chemically modified nucleotides. In some instances, fewer than 20% of the nucleotides in the poly adenosine tail are chemically modified. In some instances, fewer than 30% of the nucleotides encoding dynein axonemal intermediate chain 1 in a construct are chemically modified nucleotides. In the instances where the nucleotides comprise a chemically modified nucleotide, the chemically modified nucleotide can be selected from the group consisting of pseudouridine, 1-methylpseudouridine, 2-thiouridine, 5-iodouridine, 5-methyluridine, 5-methylcytidine, and 5-iodocytidine. In some cases, the chemically modified nucleotide is 1-methylpseudouridine. In some cases, the modified nucleotide is pseudouridine. In other cases, the modified nucleotides are a combination of 1-methylpseudouridine and pseudouridine. In addition to the composition comprising a polyribonucleotide for treating a subject having or at risk of having primary ciliary dyskinesia, in some cases, the present disclosure further provides a composition comprising at least one additional nucleic acid construct that encodes a protein selected from the group consisting of: armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin 0 (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GASB), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10).

The disclosure provides a composition comprising a nucleic acid construct encoding dynein axonemal intermediate chain 1, which nucleic acid construct includes codons that provide for heterologous or enhanced expression of the dynein axonemal intermediate chain 1 protein or a variant thereof within cells of a subject having or at risk of having primary ciliary dyskinesia. The compositions described herein may comprise a ratio of moles of amine groups of cationic polymers to moles of phosphate groups of the modified polyribonucleotide of at least about 4. In some cases, the composition is formulated in a nanoparticle or nanocapsule. In other cases, the composition is formulated in a cationic lipid, cationic polymer, or nanoemulsion. The composition may be formulated for administration to a subject. The nucleic acid constructs in the composition may include codons that provide for heterologous or enhanced expression of the dynein axonemal intermediate chain 1 protein or a variant thereof within cells of a subject having or at risk of having primary ciliary dyskinesia. In some cases, fewer than 30% of the ribonucleotides encoding dynein axonemal intermediate chain 1 are chemically modified nucleotides. In some instances, the codons of the construct are at least 70% homologous to a mammalian, such as a human, dynein axonemal intermediate chain 1 mRNA. In some cases, the construct comprises a 5' or 3' noncoding region flanking the codon sequence which encodes the dynein axonemal intermediate chain 1, wherein the noncoding region enhances the expression of the protein within cells the subject. In other cases, the construct comprises a 3' noncoding region flanking the codon sequence which encodes the dynein axonemal intermediate chain 1, wherein the 3' noncoding region comprises a 3'-cap independent translation enhancer (3'-CITEs). The 3' noncoding region may comprise a 3'-stem loop region derived from the nucleotide sequence of a histone protein. The 3' noncoding region may comprise a 3'-triple helical structure derived from the nucleotide sequence of metastasis-associated lung adenocarcinoma transcript 1 (MALAT1). The 3' noncoding region flanking the codon sequence may comprise a poly adenosine tail, wherein the number of adenosines in the poly adenosine tail improves the translation efficiency of the dynein axonemal intermediate chain 1 protein. In some cases, the number of adenosines in the poly adenosine tail improves the half-life of the dynein axonemal intermediate chain 1 protein. In some cases, the length of the poly adenosine tail is at most 200 adenosines. In some instances, a percentage of the poly adenosine tail comprises modified nucleotides. In some instances, fewer than 20% of the adenosines in the poly(A)tail are modified. In some cases, the construct comprises a percentage of chemically modified nucleotides. In some instances, fewer than 30% of the nucleotides encoding dynein axonemal intermediate chain 1 are chemically modified. When chemically modified nucleotides are present, they may be selected from the group consisting of pseudouridine, 1-methylpseudouridine, 5-methoxyuridine, 2-thiouridine, 5-iodouridine, 5-methyluridine, 5-methylcytidine, 2"-amino-2"-deoxycytidine, 2"-fluoro-2"-deoxycytidine, and 5-iodocytidine. In some cases, the chemically modified nucleotide is pseudouridine or 1-methyl pseudouridine. In some instances, the composition further comprises at least one additional nucleic acid construct. The at least one additional nucleic acid construct encodes a protein selected from the group consisting of: armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin 0 (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GASB), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10).

The present disclosure also provides a nucleic acid construct, a vector, or an isolated nucleic acid that is/are formulated for administration to a subject. In some cases, the formulation includes a therapeutically effective amount of the nucleic acid construct encoding dynein axonemal intermediate chain 1. The nucleic acid construct can be a cDNA construct that encodes dynein axonemal intermediate chain 1 protein or a variant thereof, or any one of the aforementioned additional nucleic acid constructs. In some cases, the present disclosure provides a composition comprising a nucleic acid construct encoding dynein axonemal intermediate chain 1, wherein the nucleic acid construct comprises any one of SEQ ID NOs 14-16. In some cases, the present disclosure provides a composition comprising a nucleic acid construct encoding dynein axonemal heavy chain 5, wherein the nucleic acid construct comprises any one of SEQ ID NOs 17-18.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 26A-26B illustrate an overall quality improvement in DNAI1 expressing a polyribonucleotide of SEQ ID NO 15 (B) as compared to a polyribonucleotide of SEQ ID NO 14 (A).

FIGS. 30A-30E illustrate example translation activity and immunogenicity for fractions enriched in full-length, unmodified mRNA transcripts in A549 cells using HPLC-purification.

DETAILED DESCRIPTION

Figure 1:
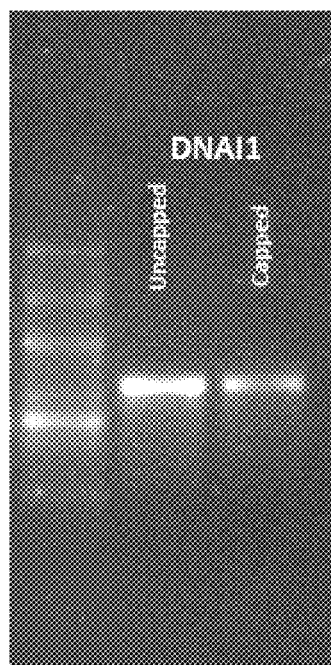
FIG. 1 is an agarose gel illustrating the production of capped and uncapped DNAI1 RNA.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "subject," as used herein generally refers to a human. In some instances, a subject can also be an animal, such as a mouse, a rat, a guinea pig, a dog, a cat, a horse, a rabbit, and various other animals. A subject can be of any age, for example, a subject can be an infant, a toddler, a child, a pre-adolescent, an adolescent, an adult, or an elderly individual.

The term "disease," as used herein, generally refers to an abnormal physiological condition that affects part or all of a subject, such as an illness (e.g., primary ciliary dyskinesia) or another abnormality that causes defects in the action of cilia in, for example, the lining the respiratory tract (lower and upper, sinuses, Eustachian tube, middle ear), in a variety of lung cells, in the fallopian tube, or flagella of sperm cells.

The term "polynucleotide" or "nucleic acid" as used herein refers to a polymeric form of nucleotides of any length, either ribonucleotides or deoxyribonucleotides, that comprise purine and pyrimidine bases, purine and pyrimidine analogues, chemically or biochemically modified, natural or non-natural, or derivatized nucleotide bases. Polynucleotides include sequences of deoxyribonucleic acid (DNA), ribonucleic acid (RNA), or DNA copies of ribonucleic acid (cDNA), all of which can be recombinantly produced, artificially synthesized, or isolated and purified from natural sources. The polynucleotides and nucleic acids may exist as single-stranded or double-stranded. The backbone of the polynucleotide can comprise sugars and phosphate groups, as may typically be found in RNA or DNA, or analogues or substituted sugar or phosphate groups. A polynucleotide may comprise naturally occurring or non-naturally occurring nucleotides, such as methylated nucleotides and nucleotide analogues (or analogs).

The term "polyribonucleotide," as used herein, generally refers to polynucleotide polymers that comprise ribonucleic acids. The term also refers to polynucleotide polymers that comprise chemically modified ribonucleotides. A polyribonucleotide can be formed of D-ribose sugars, which can be found in nature.

The term "polypeptides," as used herein, generally refers to polymer chains comprised of amino acid residue monomers which are joined together through amide bonds (peptide bonds). A polypeptide can be a chain of at least three amino acids, a protein, a recombinant protein, an antigen, an epitope, an enzyme, a receptor, or a structure analogue or combinations thereof. As used herein, the abbreviations for the L-enantiomeric amino acids that form a polypeptide are as follows: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); valine (V, Val). X or Xaa can indicate any amino acid.

The term "engineered," as used herein, generally refers to polynucleotides, vectors, and nucleic acid constructs that have been genetically designed and manipulated to provide a polynucleotide intracellularly. An engineered polynucleotide can be partially or fully synthesized in vitro. An engineered polynucleotide can also be cloned. An engineered polyribonucleotide can contain one or more base or sugar analogues, such as ribonucleotides not naturally-found in messenger RNAs. An engineered polyribonucleotide can contain nucleotide analogues that exist in transfer RNAs (tRNAs), ribosomal RNAs (rRNAs), guide RNAs (gRNAs), small nuclear RNA (snRNA), small nucleolar RNA (snoRNA), SmY RNA, spliced leader RNA (SL RNA), CRISPR RNA, long noncoding RNA (lncRNA), microRNA (miRNA), or another suitable RNA.

Overview

The present disclosure provides compositions and methods for the treatment of conditions associated with cilia maintenance and function, with nucleic acids encoding a protein or protein fragment(s). Numerous eukaryotic cells carry appendages, which are often referred to as cilia or flagella, whose inner core comprises a cytoskeletal structure called the axoneme. The axoneme can function as the skeleton of cellular cytoskeletal structures, both giving support to the structure and, in some instances, causing it to bend. Usually, the internal structure of the axoneme is common to both cilia and flagella. Cilia are often found in the linings of the airway, the reproductive system, and other organs and tissues. Flagella are tail-like structures that, similarly to cilia, can propel cells forward, such as sperm cells.

Without properly functioning cilia in the airway, bacteria can remain in the respiratory tract and cause infection. In the respiratory tract, cilia move back and forth in a coordinated way to move mucus towards the throat. This movement of mucus helps to eliminate fluid, bacteria, and particles from the lungs. Many infants afflicted with cilia and flagella malfunction experience breathing problems at birth, which suggests that cilia play an important role in clearing fetal fluid from the lungs. Beginning in early childhood, subjects afflicted with cilia malfunction can develop frequent respiratory tract infections.

Primary ciliary dyskinesia is a condition characterized by chronic respiratory tract infections, abnormally positioned internal organs, and the inability to have children (infertility). The signs and symptoms of this condition are caused by abnormal cilia and flagella. Subjects afflicted with primary ciliary dyskinesia often have year-round nasal congestion and a chronic cough. Chronic respiratory tract infections can result in a condition called bronchiectasis, which damages the passages, called bronchi, leading from the windpipe to the lungs and can cause life-threatening breathing problems.

In some instances, a nucleic acid construct, vector, or composition of the disclosure comprises one or more nucleotide sequences that encode dynein axonemal intermediate chain 1 protein or a variant thereof, and the sequences provide for heterologous or enhanced expression of the dynein axonemal intermediate chain 1 protein or a variant thereof within cells of a subject. In some instances, the nucleic acid construct, vector, or composition also comprises the genetic code of 5' untranslated regions (UTRs) and 3' UTRs of SEQ ID NOs 1-9, as shown below.

TABLE 1

| UTR | DNA sequence (from 5' to 3') |
| --- | --- |
| α-globin 5' UTR (HBA1) | GGGAGACATAAACCCTGGCGCGCTCGCGGCCCGGCACTCTTCTGGTCCCC ACAGACTCAGAGAGAAGCCACC (SEQ ID NO: 1) |
| α-globin 5' UTR (HBA2) | GGGAGACATAAACCCTGGCGCGCTCGCGGGCCGGCACTCTTCTGGTCCCC ACAGACTCAGAGAGAAGCCACC (SEQ ID NO: 2) |
| α-globin 5' UTR | GGGAGACTCTTCTGGTCCCCACAGACTCAGAGAGAACGCCACC (SEQ ID NO: 3) |
| IRES of EMCV 5'-UTR | GTTATTTTCCACCATATTGCCGTCTTTTGGCAATGTGAGGGCCCGGAAACC TGGCCCTGTCTTCTTGACGAGCATTCCTAGGGGTCTTTCCCCTCTCGCCAA AGGAATGCAAGGTCTGTTGAATGTCGTGAAGGAAGCAGTTCCTCTGGAAG CTTCTTGAAGACAAACAACGTCTGTAGCGACCCTTTGCAGGCAGCGGAAC CCCCCACCTGGCGACAGGTGCCTCTGCGGCCAAAAGCCACGTGTATAAGA TACACCTGCAAAGGCGGCACAACCCCAGTGCCACGTTGTGAGTTGGATAG TTGTGGAAAGAGTCAAATGGCTCTCCTCAAGCGTATTCAACAAGGGGCTG AAGGATGCCCAGAAGGTACCCCATTGTATGGGATCTGATCTGGGGCCTCG GTGCACATGCTTTACGTGTGTTTAGTCGAGGTTAAAAAACGTCTAGGCCC CCCGAACCACGGGGACGTGGTTTTCCTTTGAAAAAACGATGATAATATG GCCACAACC (SEQ ID NO: 4) |

TABLE 1-continued

| UTR | DNA sequence (from 5' to 3') |
|---|---|
| IRES of TEV 5'-UTR | AAATAACAAATCTCAACACAACATATACAAAACAAACGAATCTCAAGCA ATCAAGCATTCTACTTCTATTGCAGCAATTTAAATCATTTCTTTTAAAGCA AAAGCAATTTTCTGAAAATTTTCACCATTTACGAACGATAGCA (SEQ ID NO: 5) |
| ssRNA1 5'UTR | GGGAGACAAGAGAGAAAAGAAGAGCAAGAAGAAATATAAGAGCCACC (SEQ ID NO: 6) |
| SSRNA2 5'UTR | GGGAGACCCAAGCTGGCTAGCGTTTAAACTTAAGCTTGGCAATCCGGTAC TGTTGGTAAAGCCACC (SEQ ID NO: 7) |
| ssRNA 3 + native 5' UTR | GGGAGACCCAAGCTGGCTAGCGTTTAAACTTAAGCTTTCCTTTCCGGGCC GGCTGGGCGCGCCGAAGCGCCTGCGCCTTGGCTGCTGGTCGGTTGCTGGG TAACCGCGTCAGGGAGTTGGATTCTATCCTGCAAGGGCACGGGGACCCAC AACGACGGCTGTCCCTAAAGAACCGTTGCGACTGGTAACTGAAGTGGAA GAGAGTCCAGATTTCTTGTGTGTGGTCAAGGAGACGGACAAACTTTTTGT CTTCAGACGAGGGAGCGTTTTGTAGGCTCTCCAGGGGTTGAG (SEQ ID NO: 8) |
| TMV 3'-UTR | GGATTGTGTCCGTAATCACACGTGGTGCGTACGATAACGCATAGTGTTTT TCCCTCCACTTAAATCGAAGGGTTGTGTCTTGGATCGCGCGGGTCAAATG TATATGGTTCATATACATCCGCAGGCACGTAATAAAGCGAGGGGTTCGAA TCCCCCCGTTACCCCCGGTAGGGGCCCATTGTCTTC (SEQ ID NO: 9) |
| MALAT1 3'-UTR | TCAGTAGGGTCATGAAGGTTTTTCTTTTCCTGAGAAAACAACACGTATTGT TTTCTCAGGTTTTGCTTTTTGGCCTTTTTCTAGCTTAAAAAAAAAAAAAGC AAAATTGTCTTC (SEQ ID NO: 10) |
| NEAT2 3'-UTR | TCAGTAGGGTTGTAAAGGTTTTTCTTTTCCTGAGAAAACAACCTTTTGTTT TCTCAGGTTTTGCTTTTTGGCCTTTCCCTAGCTTTAAAAAAAAAAAGCAA AATTGTCTTC (SEQ ID NO: 11) |
| histone cluster 2, H3c 3'-UTR | GAAGTGGCGGTTCGGCCGGAGGTTCCATCGTATCCAAAAGGCTCTTTTCA GAGCCACCCATTGTCTTC (SEQ ID NO: 12) |
| Native 3' UTR | GGGGCTGGCCTCAGTCTCTGTCCCATCGCTTGAATACAGTACTCCTAGGG CTTGACCCTGGTACCCAGCCCAGCCTTAGCACCCAGCATGTGACCCCACT CCTGATCAGGTCCCAGCATCTTCCCTTCTTGTTCTGTTCCTTAAGGTCCCA GCACCTTACCCCAGGACTTGGTCTTCAACCACCATTACCCCTCTAACTTTG CACAAATAAACCTGTGTAGAAACCCACCCCAAAAAAA (SEQ ID NO: 13) |

Primary Ciliary Dyskinesia, Related Conditions and Treatments Thereof

The methods, constructs, and compositions of this disclosure provide a method to treat primary ciliary dyskinesia (PCD), also known as immotile ciliary syndrome or Kartagener syndrome. PCD is typically considered to be a rare, ciliopathic, autosomal recessive genetic disorder that often causes defects in the action of cilia lining the respiratory tract (lower and upper, sinuses, Eustachian tube, middle ear) and fallopian tube, as well as in the flagella of sperm cells.

Some individuals with primary ciliary dyskinesia have abnormally placed organs within their chest and abdomen. These abnormalities arise early in embryonic development when the differences between the left and right sides of the body are established. About 50 percent of people with primary ciliary dyskinesia have a mirror-image reversal of their internal organs (*situs inversus totalis*). For example, in these individuals the heart is on the right side of the body instead of on the left. When someone afflicted with primary ciliary dyskinesia has *situs inversus totalis*, they are often said to have Kartagener syndrome.

Approximately 12 percent of people with primary ciliary dyskinesia have a condition known as heterotaxy syndrome or *situs ambiguus*, which is characterized by abnormalities of the heart, liver, intestines, or spleen. These organs may be structurally abnormal or improperly positioned. In addition, affected individuals may lack a spleen (asplenia) or have multiple spleens (polysplenia). Heterotaxy syndrome results from problems establishing the left and right sides of the body during embryonic development. The severity of heterotaxy varies widely among affected individuals.

Primary ciliary dyskinesia can also lead to infertility. Vigorous movements of the flagella are can be needed to propel the sperm cells forward to the female egg cell. Because the sperm of subjects afflicted with primary ciliary dyskinesia does not move properly, males with primary ciliary dyskinesia are usually unable to father children. Infertility occurs in some affected females and it is usually associated with abnormal cilia in the fallopian tubes.

Another feature of primary ciliary dyskinesia is recurrent ear infections (otitis media), especially in young children. Otitis media can lead to permanent hearing loss if untreated. The ear infections are likely related to abnormal cilia within the inner ear.

Rarely, individuals with primary ciliary dyskinesia have an accumulation of fluid in the brain (hydrocephalus), likely due to abnormal cilia in the brain.

The polyribonucleotides of the disclosure can be used, for example, to treat a subject having or at risk of having primary ciliary dyskinesia or any other condition associated with a defect or malfunction of a gene whose function is linked to cilia maintenance and function. Non limiting examples of genes that have been associated with primary ciliary dyskinesia include: armadillo repeat containing 4

(ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin 0 (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GASB), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10).

In some cases, the composition comprises a nucleic acid construct encoding dynein axonemal intermediate chain 1 (DNAI1), and upon translation within the cells of a subject the construct yields a polypeptide that treats a subject having or at risk of having primary ciliary dyskinesia. The DNAI1 gene can provide instructions for making a protein that is part of a group (complex) of proteins called dynein. This complex functions within the cilia. Coordinated back and forth movement of cilia can move the cell or the fluid surrounding the cell and dynein produces the force needed for cilia to move. Within the core of cilia (the axoneme), dynein complexes are part of structures known as inner dynein arms (IDAs) and outer dynein arms (ODAs) depending on their location. Coordinated movement of the dynein arms causes the entire axoneme to bend back and forth. IDAs and ODAs have different combinations of protein components (subunits) that are classified by weight as heavy, intermediate, or light chains. The DNAI1 gene provides instructions for making intermediate chain 1, which is found in ODAs. Other subunits can be produced from different genes administered to the subject in the same or in a separate composition. Alternatively, other subunits can be produced by a single nucleic acid construct that encodes a functional component of an inner dynein arm or an outer dynein arm.

At least 21 mutations in the DNAI1 gene have been found to cause primary ciliary dyskinesia, which is a condition characterized by respiratory tract infections, abnormal organ placement, and an inability to have children (infertility). DNAI1 gene mutations result in an absent or abnormal intermediate chain 1. Without a normal version of this subunit, the ODAs cannot form properly and may be shortened or absent. As a result, cilia cannot produce the force needed to bend back and forth. Defective cilia lead to the features of primary ciliary dyskinesia. In some cases, the disclosure provides a nucleic acid that is engineered to replace or to supplement the function of the endogenous DNAI1 protein comprising the IVS1+2_3insT (219+3insT) mutation. In some cases, the disclosure provides a nucleic acid that is engineered to replace or to supplement the function of the endogenous DNAI1 protein comprising the A538T mutation, the second most common.

In some cases, the composition comprises a nucleic acid construct encoding dynein axonemal intermediate chain 2 (DNAI2), and upon translation within the cells of a subject the construct yields a polypeptide that treats a subject having or at risk of having primary ciliary dyskinesia. The DNAI2 gene is part of the dynein complex of respiratory cilia and sperm flagella. Mutations in this gene are associated with primary ciliary dyskinesia type 9, a disorder characterized by abnormalities of motile cilia, respiratory infections leading to chronic inflammation and bronchiectasis, and abnormalities in sperm tails.

In some cases, the composition comprises a nucleic acid construct encoding armadillo repeat containing 4 (ARMC4), and upon translation within the cells of a subject the construct yields a polypeptide that treats a subject having or at risk of having of primary ciliary dyskinesia. The protein encoded by the ARMC4 gene comprises ten Armadillo repeat motifs (ARMs) and one HEAT repeat, and has been shown to localize to the ciliary axonemes and at the ciliary base of respiratory cells. Mutations in the ARMC4 gene can cause partial outer dynein arm (ODA) defects in respiratory cilia.

In some cases, the composition comprises a nucleic acid construct encoding chromosome 21 open reading frame 59 (C21orf59), and upon translation within the cells of a subject the construct yields a polypeptide that treats a subject having or at risk of having of primary ciliary dyskinesia. The protein encoded by the C21orf59 gene can play a critical role in dynein arm assembly and motile cilia function. Mutations in this gene can result in primary ciliary dyskinesia.

In some cases, the composition comprises a nucleic acid construct encoding coiled-coil domain containing 103 (CCDC103), and upon translation within the cells of a subject the construct yields a polypeptide that treats a subject having or at risk of having of primary ciliary dyskinesia. The protein encoded by the CCDC103 gene can function as a dynein-attachment factor required for cilia motility.

In some cases, the composition comprises a nucleic acid construct encoding coiled-coil domain containing 114 (CCDC114), and upon translation within the cells of a subject the construct yields a polypeptide that treats a subject having or at risk of having of primary ciliary dyskinesia. The protein encoded by the CCDC114 gene can function as a component of the outer dynein arm docking complex in cilia cells. Mutations in this gene can cause primary ciliary dyskinesia 20.

In some cases, the composition comprises a nucleic acid construct encoding coiled-coil domain containing 39 (CCDC39), and upon translation within the cells of a subject the construct yields a polypeptide that treats a subject having or at risk of having of primary ciliary dyskinesia. The protein encoded by the CCDC39 gene can function as the assembly of dynein regulatory and inner dynein arm complexes, which regulate ciliary beat. Defects in this gene are a cause of primary ciliary dyskinesia type 14 (CCDC39).

In some cases, the composition comprises a nucleic acid construct encoding coiled-coil domain containing 40 (CCDC40), and upon translation within the cells of a subject the construct yields a polypeptide that treats a subject having or at risk of having of primary ciliary dyskinesia. The protein encoded by the CCDC40 gene can function together with CCDC39 to form a molecular ruler that determines the 96 nanometer (nm) repeat length and arrangements of components in cilia and flagella (by similarity). CCDC40 may not be required for outer dynein arm complexes assembly, but it may be required for axonemal recruitment of CCDC39. In some cases, CCD40 and CCD39 can be produced from different genes administered to the subject in the same or in a separate composition. Alternatively, CCD40 and CCD39 can be produced by a single nucleic acid construct that encodes a functional component of an inner dynein arm or an outer dynein arm. Defects in the CCD40 gene are a cause of primary ciliary dyskinesia type 14 (CILD14).

In some cases, the composition comprises a nucleic acid construct encoding coiled-coil domain containing 65 (CCDC65), and upon translation within the cells of a subject the construct yields a polypeptide that treats a subject having or at risk of having of primary ciliary dyskinesia. The protein encoded by the CCDC65 gene can function as a sperm cell protein. CCDC65 has been shown to be highly expressed in adult testis, spermatocytes and spermatids. The protein plays a critical role in the assembly of the nexin-dynein regulatory complex. Mutations in this gene have been associated with primary ciliary dyskinesia type 27.

In some cases, the composition comprises a nucleic acid construct encoding cyclin 0 (CCNO), and upon translation within the cells of a subject the construct yields a polypeptide that treats a subject having or at risk of having of primary ciliary dyskinesia.

In some cases, the composition comprises a nucleic acid construct encoding dynein (axonemal) assembly factor 1 (DNAAF1), and upon translation within the cells of a subject the construct yields a polypeptide that treats a subject having or at risk of having of primary ciliary dyskinesia. The protein encoded by the DNAAF1 gene is thought to be cilium-specific and it can be required for the stability of the ciliary architecture. Mutations in this gene have been associated with primary ciliary dyskinesia type 13.

In some cases, the composition comprises a nucleic acid construct encoding dynein (axonemal) assembly factor 2 (DNAAF2), and upon translation within the cells of a subject the construct yields a polypeptide that treats a subject having or at risk of having of primary ciliary dyskinesia. The protein encoded by the DNAAF2 gene can be involved in the preassembly of dynein arm complexes which power cilia. Mutations in this gene have been associated with primary ciliary dyskinesia type 10 (CILD10).

In some cases, the composition comprises a nucleic acid construct encoding dynein (axonemal) assembly factor 3 (DNAAF3), and upon translation within the cells of a subject the construct yields a polypeptide that treats a subject having or at risk of having of primary ciliary dyskinesia. The protein encoded by the DNAAF3 gene can be required for the assembly of axonemal inner and outer dynein arms and it can play a role in assembling dynein complexes for transport into cilia. Mutations in this gene have been associated with primary ciliary dyskinesia type 2 (CILD2).

In some cases, the composition comprises a nucleic acid construct encoding dynein (axonemal) assembly factor 5 (DNAAF5), and upon translation within the cells of a subject the construct yields a polypeptide that treats a subject having or at risk of having of primary ciliary dyskinesia. The protein encoded by the DNAAF5 gene is thought to be required for the preassembly or stability of axonemal dynein arms, and is found only in organisms with motile cilia and flagella. Mutations in this gene have been associated with primary ciliary dyskinesia-18.

In some cases, the composition comprises a nucleic acid construct encoding dynein axonemal heavy chain 11 (DNAH11), and upon translation within the cells of a subject the construct yields a polypeptide that treats a subject having or at risk of having of primary ciliary dyskinesia. The protein encoded by the DNAH11 gene can produce a ciliary outer dynein arm protein. DNAH11 is thought to be a microtubule-dependent motor ATPase involved in the movement of respiratory cilia. Mutations in this gene have been associated with primary ciliary dyskinesia type 7 (CILD7) and heterotaxy syndrome.

In some cases, the composition comprises a nucleic acid construct encoding dynein axonemal heavy chain 5 (DNAH5), and upon translation within the cells of a subject the construct yields a polypeptide that treats a subject having or at risk of having primary ciliary dyskinesia. The DNAH5 gene can provide instructions for making a protein that is part of a group (complex) of proteins called dynein. Coordinated back and forth movement of cilia can move the cell or the fluid surrounding the cell. Dynein can produce the force needed for cilia to move. More than 80 mutations of the DNAH5 have been associated with primary ciliary dyskinesia. Mutations in this gene have been associated with primary ciliary dyskinesia and heterotaxy syndrome.

In some cases, the composition comprises a nucleic acid construct encoding dynein axonemal heavy chain 6 (DNAH6), and upon translation within the cells of a subject the construct yields a polypeptide that treats a subject having or at risk of having primary ciliary dyskinesia.

In some cases, the composition comprises a nucleic acid construct encoding dynein axonemal heavy chain 8 (DNAH8), and upon translation within the cells of a subject the construct yields a polypeptide that treats a subject having or at risk of having of primary ciliary dyskinesia. The protein encoded by the DNAH8 gene can function as a force generating protein of respiratory cilia. DNAH8 can produce force towards the minus ends of microtubules. Dynein has ATPase activity; the force-producing power stroke is thought to occur on release of ADP. DNAH8 can be involved in sperm motility and in sperm flagellar assembly. DNAH8 is also known as ATPase and hdhc9.

In some cases, the composition comprises a nucleic acid construct encoding dynein axonemal light chain 1 (DNAL1), and upon translation within the cells of a subject the construct yields a polypeptide that treats a subject having or at risk of having of primary ciliary dyskinesia. The protein encoded by the DNAL1 gene can function as a force generating protein of respiratory cilia. DNAL1 can function as a component of the outer dynein arms complex. This complex acts as the molecular motor that provides the force to move cilia in an ATP-dependent manner. Mutations in this gene have been associated with primary ciliary dyskinesia type 16 (CILD16).

In some cases, the composition comprises a nucleic acid construct encoding dynein regulatory complex subunit 1 (DRC1), and upon translation within the cells of a subject the construct yields a polypeptide that treats a subject having or at risk of having of primary ciliary dyskinesia. The protein encoded by the DRC1 gene can function as a force generating protein of respiratory cilia. DRC1 can encode a central component of the nexin-dynein complex (N-DRC), which regulates the assembly of ciliary dynein. Mutations in this gene have been associated with primary ciliary dyskinesia type 21 (CILD21).

In some cases, the composition comprises a nucleic acid construct encoding dyslexia susceptibility 1 candidate 1 (DYX1C1), and upon translation within the cells of a subject the construct yields a polypeptide that treats a subject having or at risk of having of primary ciliary dyskinesia. The protein encoded by the DYX1C1 gene can function as a force generating protein of respiratory cilia. DYX1C1 can encode a tetratricopeptide repeat domain-containing protein. The encoded protein can interact with estrogen receptors and the heat shock proteins, Hsp70 and Hsp90. Mutations in this gene are also associated with deficits in reading and spelling, and a chromosomal translocation involving this gene is associated with a susceptibility to developmental dyslexia.

In some cases, the composition comprises a nucleic acid construct encoding growth arrest specific 8 (GASB), and upon translation within the cells of a subject the construct yields a polypeptide that treats a subject having or at risk of having of primary ciliary dyskinesia.

In some cases, the composition comprises a nucleic acid construct encoding axonemal central pair apparatus protein (HYDIN), and upon translation within the cells of a subject the construct yields a polypeptide that treats a subject having or at risk of having of primary ciliary dyskinesia. The protein encoded by the HYDIN gene can function in cilia motility. Mutations in this gene have been associated with primary ciliary dyskinesia type 5 (CILD5).

In some cases, the composition comprises a nucleic acid construct encoding leucine rich repeat containing 6 (LRRC6), and upon translation within the cells of a subject the construct yields a polypeptide that treats a subject having or at risk of having of primary ciliary dyskinesia. The protein encoded by the LRRC6 gene contains several leucine-rich repeat domains and appears to be involved in the motility of cilia. Mutations in this gene have been associated with primary ciliary dyskinesia type 19 (CILD19).

In some cases, the composition comprises a nucleic acid construct encoding NME/NM23 family member 8 (NME8), and upon translation within the cells of a subject the construct yields a polypeptide that treats a subject having or at risk of having of primary ciliary dyskinesia. The protein encoded by the NME8 gene can function as a force generating protein of respiratory cilia. The NME8 protein comprises an N-terminal thioredoxin domain and three C-terminal nucleoside diphosphate kinase (NDK) domains. Mutations in this gene have been associated with primary ciliary dyskinesia type 6 (CILD6).

In some cases, the composition comprises a nucleic acid construct encoding oral-facial-digital syndrome 1 (OFD1), and upon translation within the cells of a subject the construct yields a polypeptide that treats a subject having or at risk of having of primary ciliary dyskinesia. The function of the protein produced by the OFD1 gene is not well understood, but it may play a role play a critical role in the early development of many parts of the body, including the brain, face, limbs, and kidneys. About 100 mutations in the OFD1 gene have been found in people with oral-facial-digital syndrome type I, which is the most common form of the disorder. Mutations in this gene have been associated with primary ciliary dyskinesia and Joubert syndrome.

In some cases, the composition comprises a nucleic acid construct encoding retinitis pigmentosa GTPase regulator (RPGR), and upon translation within the cells of a subject the construct yields a polypeptide that treats a subject having or at risk of having of primary ciliary dyskinesia. The protein encoded by the RPGR gene can be important for normal vision and for the function of the cilia. Mutations in this gene have been associated with primary ciliary dyskinesia, X-linked retinitis pigmentosa, progressive vision loss, chronic respiratory and sinus infections, recurrent ear infections (otitis media), and hearing loss.

In some cases, the composition comprises a nucleic acid construct encoding radial spoke head 1 homolog (RSPH1), and upon translation within the cells of a subject the construct yields a polypeptide that treats a subject having or at risk of having of primary ciliary dyskinesia. The protein encoded by the RSPH1 gene may play an important role in male meiosis and in the building of the axonemal central pair and radial spokes. Mutations in this gene have been associated with primary ciliary dyskinesia type 24 (CILD24).

In some cases, the composition comprises a nucleic acid construct encoding radial spoke head 4 homolog A (RSPH4A), and upon translation within the cells of a subject the construct yields a polypeptide that treats a subject having or at risk of having of primary ciliary dyskinesia. The protein encoded by the RSPH4A gene may be a component the radial spoke head. Mutations in this gene have been associated with primary ciliary dyskinesia type 11 (CILD11).

In some cases, the composition comprises a nucleic acid construct encoding radial spoke head 9 homolog (RSPH9), and upon translation within the cells of a subject the construct yields a polypeptide that treats a subject having or at risk of having of primary ciliary dyskinesia. The protein encoded by the RSPH9 gene may be a component the radial spoke head in motile cilia and flagella. Mutations in this gene have been associated with primary ciliary dyskinesia type 12 (CILD12).

In some cases, the composition comprises a nucleic acid construct encoding sperm associated antigen 1 (SPAG1), and upon translation within the cells of a subject the construct yields a polypeptide that treats a subject having or at risk of having of primary ciliary dyskinesia. The protein encoded by the SPAG1 gene may play a role in the cytoplasmic assembly of the ciliary dynein arms. Mutations in this gene have been associated with primary ciliary dyskinesia type 28 (CILD28).

In some cases, the composition comprises a nucleic acid construct encoding zinc finger MYND-type containing 10 (ZMYND10), and upon translation within the cells of a subject the construct yields a polypeptide that treats a subject having or at risk of having of primary ciliary dyskinesia. The protein encoded by the ZMYND10 can function in axonemal assembly of inner and outer dynein arms (IDA and ODA, respectively) for proper axoneme building for cilia motility. Mutations in this gene have been associated with primary ciliary dyskinesia type 22 (CILD22).

The treatment may comprise treating a subject (e.g., a patient with a disease and/or a lab animal with a condition). In some cases, the condition is primary ciliary dyskinesia (PCD) or Kartagener syndrome. In some cases, the condition is broadly associated with defects in one or more proteins that function within cell structures known as cilia. In some cases, the subject is a human. Treatment may be provided to the subject before clinical onset of disease. Treatment may be provided to the subject after clinical onset of disease. Treatment may be provided to the subject on or after 1 minute, 5 minutes, 10 minutes, 30 minutes, 1 hour, 2 hours, 3 hours, 4 hours, 5 hours, 6 hours, 12 hours, 1 day, 1 week, 6 months, 12 months, or 2 years after clinical onset of the disease. Treatment may be provided to the subject for a time period that is greater than or equal to 1 minute, 10 minutes, 30 minutes, 1 hour, 2 hours, 3 hours, 4 hours, 5 hours, 6 hours, 12 hours, 1 day, 1 week, 1 month, 6 months, 12 months, 2 years or more after clinical onset of the disease. Treatment may be provided to the subject for a time period that is less than or equal to 2 years, 12 months, 6 months, 1 month, 1 week, 1 day, 12 hours, 6 hours, 5 hours, 4 hours, 3 hours, 2 hours, 1 hour, 30 minutes, 10 minutes, or 1 minute after clinical onset of the disease. Treatment may also include treating a human in a clinical trial.

Compositions containing the engineered polyribonucleotides described herein can be administered for prophylactic and/or therapeutic treatments. In therapeutic applications, the nucleic acid constructs or vectors can be administered to a subject already suffering from a disease, such as a primary ciliary dyskinesia, in the amount sufficient to provide the amount of the encoded polypeptide that cures or at least improves the symptoms of the disease. Nucleic acid constructs, vectors, engineered polyribonucleotides, or compositions can also be administered to lessen a likelihood of developing, contracting, or worsening a disease. Amounts effective for this use can vary based on the severity and course of the disease or condition, the efficiency of transfection of a nucleic acid construct(s), vector(s), engineered polyribonucleotide(s), or composition(s), the affinity of an encoded polypeptide to a target molecule, previous therapy, the subject's health status, weight, response to the drugs, and the judgment of the treating physician.

In some cases, a polynucleotide of the disclosure can encode a polypeptide that is at least 5%, 10%, 15%, 20%, 25%, 30%, 35%, 40%, 45%, 50%, 55%, 60%, 65%, 70%, 75%, 80%, 85%, 90%, or 95% homologous to a protein associated with primary ciliary dyskinesia, such as armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin 0 (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GASB), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (Chlamydomonas) (RSPH1), radial spoke head 4 homolog A (Chlamydomonas) (RSPH4A), radial spoke head 9 homolog (Chlamydomonas) (RSPH9), sperm associated antigen 1(SPAG1), and zinc finger MYND-type containing 10 (ZMYND10).

Multiple nucleic acid constructs, vectors, engineered polyribonucleotides, or compositions can be administered in any order or simultaneously. The nucleic acid constructs, vectors, engineered polyribonucleotides, or compositions can be packed together or separately, in a single package comprising polyribonucleotides that target the same target molecule or in a plurality of packages. One or all of the nucleic acid constructs, vectors, engineered polyribonucleotides, or compositions can be given in multiple doses. If not simultaneous, the timing between the multiple doses may vary.

The nucleic acid constructs, vectors, engineered polyribonucleotides, or compositions can be administered to a subject as soon as possible after the onset of the symptoms. A nucleic acid construct(s), a vector(s), engineered polyribonucleotide(s), or compositions can be administered as soon as is practical after the onset of a disease or condition is detected or suspected, and for a length of time necessary for the treatment of the disease, such as, for example, for about 1 month, for about 6 months, for about 12 months, for about 18 months, for about 24 months, or any appropriate length of time. The length of treatment can vary for each subject.

Altered Nucleotide Usage in Coding Regions to Increase mRNA Stability for Transcript Therapy Hydrolysis of oligonucleotides suggests that the reactivity of the phosphodiester bond linking two ribonucleotides in single-stranded (ss)RNA depends on the nature of those nucleotides. At pH 8.5, dinucleotide cleavage susceptibility when embedded in ssRNA dodecamers may vary by an order of magnitude. Under near physiological conditions, hydrolysis of RNA usually involves an $S_N2$-type attack by the 2'-oxygen nucleophile on the adjacent phosphorus target center on the opposing side of the 5'-oxyanion leaving group, yielding two RNA fragments with 2',3'-cyclic phosphate and 5'-hydroxyl termini. More reactive scissile phosphodiester bonds may include 5'-UpA-3' ($R_1=U_1$, $R_2=A$) and 5'-CpA-3' ($R_1=C$, $R_2=A$) because the backbone at these steps can most easily adopt the "in-line" conformation that is required for $S_N2$-type nucleophilic attack by the 2'-OH on the adjacent phosphodiester linkage. In addition, interferon-regulated dsRNA-activated antiviral pathways produce 2'-5' oligoadenylates which bind to ankyrin repeats leading to activation of RNase L endoribonuclease. RNase L cleaves ssRNA efficiently at UA and UU dinucleotides. Lastly, U-rich sequences are potent activators of RNA sensors including Toll-like receptor 7 and 8 and RIG-I making global uridine content reduction a potentially attractive approach to reduce immunogenicity of therapeutic mRNAs.

Altered nucleotide usage schemes aiming to reduce the number of more reactive 5'-U(U/A)-3' dinucleotides within codons as well as across codons of modified mRNAs partially alleviate limitations imposed by the inherent chemical instability of RNA. At the same time, lowering the U-content in RNA transcripts renders them less immunogenic. The present disclosure relates to RNA transcripts comprising altered open reading frames (ORF). In particular, a method comprising a substantial reduction of 5'-U(U/A)-3' dinucleotides within protein coding regions leading to stabilized therapeutic mRNAs is proposed.

TABLE 2

| Construct | DNA sequence (from 5' to 3') |
|---|---|
| DNAI1 GeneScript Codon | ATGATCCCAGCAAGCGCCAAGGCACCACACAAGCAGCCCCACAAGCAGA GCATCTCCATCGGCAGGGGCACAAGGAAGAGGGACGAGGATAGCGGAAC CGAAGTGGGAGAGGGAACAGACGAGTGGGCACAGTCCAAGGCAACCGTG CGCCCACCTGACCAGCTGGAGCTGACAGATGCCGAGCTGAAGGAGGAGT TCACCAGGATCCTGACAGCCAACAATCCACACGCCCCCCAGAACATCGTG CGCTACTCTTTCAAGGAGGGCACATATAAGCCAATCGGCTTTGTGAACCA GCTGGCCGTGCACTATACCCAAGTGGGCAATCTGATCCCCAAGGACTCCG ATGAGGGCCGGAGACAGCACTACAGGGACGAGCTGGTGGCAGGATCCCA GGAGTCTGTGAAAGTGATCTCTGAGACCGGCAATCTGGAGGAGGACGAG GAGCCAAAGGAGCTGGAGACCGAGCCAGGAAGCCAGACAGATGTGCCTG |

TABLE 2-continued

| Construct | DNA sequence (from 5' to 3') |
|---|---|
| | CAGCAGGAGCAGCAGAGAAGGTGACCGAGGAGGAGCTGATGACACCTAA<br>GCAGCCAAAGGAGCGGAAGCTGACCAACCAGTTCAATTTTTCCGAGAGA<br>GCCTCTCAGACATACAACAATCCAGTGCGGGACAGAGAGTGCCAGACCG<br>AGCCACCCCCTAGAACCAACTTTTCCGCCACAGCCAATCAGTGGGAGATC<br>TACGATGCCTATGTGGAGGAGCTGGAGAAGCAGGAGAAGACCAAGGAGA<br>AGGAGAAGGCCAAGACACCCGTGGCCAAGAAGTCCGGCAAGATGGCCAT<br>GCGGAAGCTGACCAGCATGGAGTCCCAGACAGACGATCTGATCAAGCTG<br>TCTCAGGCCGCCAAGATCATGGAGAGAATGGTGAACCAGAATACCTATG<br>ACGATATCGCCCAGGACTTCAAGTACTATGACGATGCAGCAGACGAGTAC<br>AGGGATCAAGTGGGCACACTGCTGCCTCTGTGGAAGTTTCAGAACGATAA<br>GGCCAAGAGGCTGAGCGTGACCGCCCTGTGCTGGAATCCAAAGTACAGG<br>GACCTGTTCGCAGTGGGATACGGATCTTATGACTTCATGAAGCAGAGCAG<br>AGGCATGCTGCTGCTGTATTCCCTGAAGAACCCCTCTTTCCCTGAGTACAT<br>GTTTAGCTCCAATTCCGGCGTGATGTGCCTGGACATCCACGTGGATCACC<br>CCTACCTGGTGGCCGTGGGCCACTATGACGGCAACGTGGCCATCTACAAT<br>CTGAAGAAGCCTCACTCTCAGCCCAGCTTCTGTTCTAGCGCCAAGAGCGG<br>CAAGCACTCCGATCCCGTGTGGCAGGTGAAGTGGCAGAAGGACGATATG<br>GACCAGAACCTGAATTTCTTTTCCGTGTCCTCTGATGGCAGGATCGTGTCT<br>TGGACCCTGGTGAAGCGCAAGCTGGTGCACATCGACGTGATCAAGCTGA<br>AGGTGGAGGGCAGCACCACAGAGGTGCCAGAGGGACTGCAGCTGCACCC<br>AGTGGGATGCGGCACAGCCTTCGACTTTCACAAGGAGATCGATTATATGT<br>TCCTGGTGGGCACCGAGGAGGGCAAGATCTACAAGTGTTCTAAGAGCTAT<br>AGCTCCCAGTTTCTGGACACATATGATGCCCACAACATGAGCGTGGATAC<br>CGTGTCCTGGAATCCTTACCACACAAAGGTGTTCATGAGCTGCTCTAGCG<br>ACTGGACCGTGAAGATCTGGGATCACACCATCAAGACACCTATGTTTATC<br>TATGACCTGAACTCCGCCGTGGGCGATGTGGCATGGGCACCATACTCCTC<br>TACAGTGTTCGCAGCAGTGACCACAGACGGCAAGGCACACATCTTTGATC<br>TGGCCATCAACAAGTACGAGGCCATCTGTAATCAGCCCGTGGCCGCCAAG<br>AAGAACAGGCTGACCCACGTGCAGTTCAATCTGATCCACCCTATCATCAT<br>CGTGGGCGACGATCGGGGCCACATCATCTCTCTGAAGCTGAGCCCCAACC<br>TGAGAAAGATGCCTAAGGAGAAGAAGGGACAGGAGGTGCAGAAGGGAC<br>CAGCAGTGGAGATCGCAAAGCTGGACAAGCTGCTGAATCTGGTGCGCGA<br>GGTGAAGATCAAGACCTGA (SEQ ID NO: 14) |
| DNAI1<br>Altered<br>Nucleotide<br>Usage 1 | ATGATCCCAGCAAGCGCCAAGGCACCCACACAAGCAGCCCCACAAGCAGA<br>GCATCAGCATCGGCAGGGGCACAAGGAAGAGGGACGAGGACAGCGGAA<br>CCGAAGTGGGAGAGGGAACAGACGAGTGGGCACAGAGCAAGGCAACCG<br>TGCGCCCACCCGACCAGCTGGAGCTGACAGACGCCGAGCTGAAGGAGGA<br>GTTCACCAGGATCCTGACAGCCAACAACCCACACGCCCCCCAGAACATCG<br>TGCGCTACAGCTTCAAGGAGGGCACATACAAGCCAATCGGCTTCGTGAAC<br>CAGCTGGCCGTGCACTACACCCAAGTGGGCAACCTGATCCCCAAGGACA<br>GCGACGAGGGCCGGAGACAGCACTACAGGGACGAGCTGGTGGCAGGAA<br>GCCAGGAGAGCGTGAAAGTGATCAGCGAGACCGGCAACCTGGAGGAGGA<br>CGAGGAGCCAAAGGAGCGGAAGGACCGAGCCAGGAAGCCAGACAGACGT<br>GCCCGCAGCAGGAGCAGCAGAGAAGGTGACCGAGGAGGAGCTGATGAC<br>ACCCAAGCAGCCAAAGGAGCGGAAGCTGACCAACCAGTTCAACTTCAGC<br>GAGAGAGCCAGCCAGACATACAACAACCCAGTGCGGGACAGAGAGTGCC<br>AGACCGAGCCCACCCCCCAGAACCAACTTCAGCGCCACAGCCAACCAGTG<br>GGAGATCTACGACGCCTACGTGGAGGAGCTGGAGAAGCAGGAGAAGACC<br>AAGGAGAAGGAGAAGGCCAAGACACCCGTGGCCAAGAAGAGCGGCAAG<br>ATGGCCATGCGGAAGCTGACCAGCATGGAGAGCCAGACAGACGACCTGA<br>TCAAGCTGAGCCAGGCCGCCAAGATCATGGAGAGAATGGTGAACCAGAA<br>CACCTACGACGACATCGCCCAGGACTTCAAGTACTACGACGACGCAGCA<br>GACGAGTACAGGGACCAAGTGGGCACACTGCTGCCCCTGTGGAAGTTCC<br>AGAACGACAAGGCCAAGAGGCTGAGCGTGACCGCCCTGTGCTGGAACCC<br>AAAGTACAGGGACCTGTTCGCAGTGGGATACGGAAGCTACGACTTCATG<br>AAGCAGAGCAGAGGCATGCTGCTGCTGTACAGCCTGAAGAACCCCAGCT<br>TCCCCGAGTACATGTTCAGCAGCAACAGCGGCGTGATGTGCCTGGACATC<br>CACGTGGACCACCCCTACCTGGTGGCCGTGGGCCACTACGACGGCAACGT<br>GGCCATCTACAACCTGAAGAAGCCCCACAGCCAGCCCAGCTTCTGCAGCA<br>GCGCCAAGAGCGGCAAGCACAGCGACCCCGTGTGGCAGGTGAAGTGGCA<br>GAAGGACGACATGGACCAGAACCTGAACTTCTTCAGCGTGAGCAGCGAC<br>GGCAGGATCGTGAGCTGGACCCTGGTGAAGCGCAAGCTGGTGCACATCG<br>ACGTGATCAAGCTGAAGGTGGAGGGCAGCACCACAGAGGTGCCAGAGGG<br>ACTGCAGCTGCACCCAGTGGGATGCGGCACAGCCTTCGACTTCCACAAGG<br>AGATCGACTACATGTTCCTGGTGGGCACCGAGGAGGGCAAGATCTACAA<br>GTGCAGCAAGAGCTACAGCAGCCAGTTCCTGGACACATACGACGCCCAC<br>AACATGAGCGTGGACACCGTGAGCTGGAACCCCTACCACACAAAGGTGT<br>TCATGAGCTGCAGCAGCGACTGGACCGTGAAGATCTGGGACCACACCATC<br>AAGACACCCATGTTCATCTACGACCTGAACAGCGCCGTGGGCGACGTGGC<br>ATGGGCACCATACAGCAGCACAGTGTTCGCAGCAGTGACCACAGACGGC<br>AAGGCACACATCTTCGACCTGGCCATCAACAAGTACGAGGCCATCTGCAA<br>CCAGCCCGTGGCCGCCAAGAAGAACAGGCTGACCCACGTGCAGTTCAAC<br>CTGATCCACCCCATCATCATCGTGGGCGACGACCGGGGCCACATCATCAG<br>CCTGAAGCTGAGCCCCAACCTGAGAAAGATGCCCAAGGAGAAGAAGGGA<br>CAGGAGGTGCAGAAGGGACCAGCAGTGGAGATCGCAAAGCTGGACAAGC<br>TGCTGAACCTGGTGCGCGAGGTGAAGATCAAGACCTGA (SEQ ID NO: 15) |

TABLE 2-continued

| Construct | DNA sequence (from 5' to 3') |
|---|---|
| DNAI1 Altered Nucleotide Usage 2 | ATGATCCCAGCAAGCGCCAAGGCACCCACACAAGCAGCCCCACAAGCAGA<br>GCATCTCCATCGGCAGGGGCACAAGGAAGAGGGACGAGGACAGCGGAAC<br>CGAAGTGGGAGAGGGAACAGACGAGTGGGCACAGTCCAAGGCAACCGTG<br>CGCCCACCTGACCAGCTGGAGCTGACAGATGCCGAGCTGAAGGAGGAGT<br>TCACCAGGATCCTGACAGCCAACAATCCACACGCCCCCCAGAACATCGTG<br>CGCTACAGCTTCAAGGAGGGCACATACAAGCCAATCGGCTTCGTGAACCA<br>GCTGGCCGTGCACTACACCCAAGTGGGCAATCTGATCCCCAAGGACTCCG<br>ATGAGGGCCGGAGACAGCACTACAGGGACGAGCTGGTGGCAGGATCCCA<br>GGAGTCTGTGAAAGTGATCTCTGAGACCGGCAATCTGGAGGAGGACGAG<br>GAGCCAAAGGAGCTGGAGACCGAGCCAGGAAGCCAGACAGATGTGCCTG<br>CAGCAGGAGCAGCAGAGAAGGTGACCGAGGAGGAGCTGATGACACCCA<br>AGCAGCCAAAGGAGCGGAAGCTGACCAACCAGTTCAACTTCTCCGAGAG<br>AGCCTCTCAGACATACAACAATCCAGTGCGGGACAGAGAGTGCCAGACC<br>GAGCCACCCCCCAGAACCAACTTCTCCGCCACAGCCAATCAGTGGGAGAT<br>CTACGATGCCTACGTGGAGGAGCTGGAGAAGCAGGAGAAGACCAAGGAG<br>AAGGAGAAGGCCAAGACACCCGTGGCCAAGAAGTCCGGCAAGATGGCCA<br>TGCGGAAGCTGACCAGCATGGAGTCCCAGACAGACGATCTGATCAAGCT<br>GTCTCAGGCCGCCAAGATCATGGAGAGAATGGTGAACCAGAACACCTAC<br>GACGACATCGCCCAGGACTTCAAGTACTACGACGATGCAGCAGACGAGT<br>ACAGGGATCAAGTGGGCACACTGCTGCCTCTGTGGAAGTTCCAGAACGAC<br>AAGGCCAAGAGGCTGAGCGTGACCGCCCTGTGCTGGAATCCAAAGTACA<br>GGGACCTGTTCGCAGTGGGATACGGAAGCTACGACTTCATGAAGCAGAG<br>CAGAGGCATGCTGCTGCTGTACTCCCTGAAGAACCCCAGCTTCCCTGAGT<br>ACATGTTCAGCTCCAACTCCGGCGTGATGTGCCTGGACATCCACGTGGAT<br>CACCCCTACCTGGTGGCCGTGGGCCACTACGACGGCAACGTGGCCATCTA<br>CAATCTGAAGAAGCCTCACTCTCAGCCCAGCTTCTGCAGCAGCGCCAAGA<br>GCGGCAAGCACTCCGATCCCGTGTGGCAGGTGAAGTGGCAGAAGGACGA<br>CATGGACCAGAACCTGAACTTCTTCTCCGTGTCCTCTGATGGCAGGATCG<br>TGAGCTGGACCCTGGTGAAGCGCAAGCTGGTGCACATCGACGTGATCAA<br>GCTGAAGGTGGAGGGCAGCACCACAGAGGTGCCAGAGGGACTGCAGCTG<br>CACCCAGTGGGATGCGGCACAGCCTTCGACTTCCACAAGGAGATCGACTA<br>CATGTTCCTGGTGGGCACCGAGGAGGGCAAGATCTACAAGTGCAGCAAG<br>AGCTACAGCTCCCAGTTCCTGGACACATACGATGCCCACAACATGAGCGT<br>GGACACCGTGTCCTGGAATCCCTACCACACAAAGGTGTTCATGAGCTGCA<br>GCAGCGACTGGACCGTGAAGATCTGGGATCACACCATCAAGACACCCAT<br>GTTCATCTACGACCTGAACTCCGCCGTGGGCGATGTGGCATGGGCACCAT<br>ACTCCAGCACAGTGTTCGCAGCAGTGACCACAGACGGCAAGGCACACAT<br>CTTCGATCTGGCCATCAACAAGTACGAGGCCATCTGCAATCAGCCCGTGG<br>CCGCCAAGAAGAACAGGCTGACCCACGTGCAGTTCAATCTGATCCACCCC<br>ATCATCATCGTGGGCGACGATCGGGGCCACATCATCTCTCTGAAGCTGAG<br>CCCCAACCTGAGAAAGATGCCCAAGGAGAAGAAGGGACAGGAGGTGCA<br>GAAGGGACCAGCAGTGGAGATCGCAAAGCTGGACAAGCTGCTGAATCTG<br>GTGCGCGAGGTGAAGATCAAGACCTGA (SEQ ID NO: 16) |
| DNAH5 Altered Nucleotide Usage 1 | ATGTTCAGAATCGGCAGACGGCAGCTGTGGAAGCACAGCGTGACCGAGA<br>TGCTGACCCAGCGGCTGAAGGGCGAGAAAGAGGCCAAGAGAGCCCTGCT<br>GGACGCCCGGCACAAcTACCTGTTCGCCATCGTGGCCAGCTGCCTGGACC<br>TGAACAAGACCGAGGTGGAAGACGCCATCCTGGAAGGCAACCAGATCGA<br>GCGGATCGACCAGCTGTTCGCCGTGGGCGGACTGCGGCACCTGATGTTCT<br>ACTACCAAGACGTGGAAGAGGCCGAGACAGGCCAGCTGGGAAGCCTGGG<br>CGGAGTGAACCTGGTGAGCGGCAAGATCAAGAAACCCAAGGTGTTCGTG<br>ACCGAGGGCAACGACGTGGCCCTGACAGGCGTGTGCGTGTTCTTCATCAG<br>AACCGACCCCAGCAAGGCCATCACCCCCGACAACATCCACCAGGAAGTG<br>AGCTTCAACATGCTGGACGCCGCCGACGGCGGCCTGCTGAACAGCGTGCG<br>GAGACTGCTGAGCGACATCTTCATCCCCGCCCTGAGAGCCACAAGCCACG<br>GCTGGGGAGAGCTGGAAGGACTGCAGGACGCCGCCAACATCCGGCAGGA<br>ATTCCTGAGCAGCCTGGAAGGATTCGTGAACGTGCTGAGCGGCGCCCAGG<br>AAAAGCCTGAAAGAAAAAGTGAACCTGCGGAAGTGCGACATCCTGGAACT<br>GAAAACCCTGAAAGAGCCCACCGACTACCTGACCCTGGCCAACAACCCC<br>GAGACACTGGGCAAGATCGAGGACTGCATGAAAGTGTGGATCAAGCAGA<br>CCGAACAGGTGCTGGCCGAGAACAACCAGCTGCTGAAAGAAGCCGACGA<br>CGTGGGCCCAAGAGCCGAGCTGGAACACTGGAAGAAGCGGCTGAGCAAG<br>TTCAACTACCTGCTGGAACAGCTGAAGAGCCCCGACGTGAAGGCCGTGCT<br>GGCCGTGCTGGCAGCCGCCAAGAGCAAACTGCTGAAAACCTGGCGCGAG<br>ATGGACATCCGGATCACCGACGCGCCACCAACGAGGCCAAGGACAACGTGA<br>AGTACCTGTACACCCTGGAAAAGTGCTGCGACCCCCTGTACAGCAGCGAC<br>CCCCTGAGCATGATGGACGCCATCCCCACCCTGATCAACGCCATCAAGAT<br>GATCTACAGCATCAGCCACTACTACAACACCAGCGAGAAGATCACCAGC<br>CTGTTCGTGAAAGTGACCAACCAGATCATCAGCGCCTGCAAGGCCTACAT<br>CACCAACAACGGCACCGCCAGCATCTGGAACCAGCCCCAGGACGTGGTG<br>GAAGAGAAGATCCTGAGCGCCATCAAGCTGAAGCAGGAATACCAGCTGT<br>GCTTCCACAAGACCAAGCAGAAGCTGAAACAGAACCCCAACGCCAAGCA<br>GTTCGACTTCAGCGAGATGTACATCTTCGGCAAGTTCGAGACATTCCACC<br>GGCGGCTGGCCAAGATCATCGACATCTTCACCACCCTGAAAACATACAGC<br>GTGCTGCAGGACAGCACCATCGAGGGCCTGGAAGACATGGCCACCAAGT<br>ACCAGGGCATCGTGGCCACCATCAAGAAGAAAGAGTACAACTTCCTGGA<br>CCAGCGCAAGATGGACTTCGACCAGGACTACGAGGAATTCTGCAAGCAG<br>ACAAACGACCTGCACAACGAGCTGCGCAAGTTCATGGACGTGACCTTCGC |

TABLE 2-continued

| Construct | DNA sequence (from 5' to 3') |
|---|---|
| | CAAGATCCAGAACACCAACCAGGCCCTGCGGATGCTGAAGAAGTTCGAG |
| | AGACTGAACATCCCCAACCTGGGCATCGACGACAAGTACCAGCTGATCCT |
| | GGAAAACTACGGCGCCGACATCGACATGATCAGCAAGCTGTACACAAAG |
| | CAGAAGTACGACCCCCCCCTGGCCCGGAACCAGCCCCCCATCGCCGGCAA |
| | AATCCTGTGGGCCAGACAGCTGTTCCACCGGATCCAGCAGCCCATGCAGC |
| | TGTTCCAGCAGCACCCCGCCGTGCTGAGCACAGCCGAGGCCAAACCCATC |
| | ATCCGGAGCTACAACCGGATGGCCAAGGTGCTGCTGGAATTCGAGGTGCT |
| | GTTCCACCGGGCCTGGCTGCGGCAGATCGAAGAGATCCACGTGGGACTG |
| | GAAGCCAGCCTGCTCGTGAAGGCCCCCGGAACCGGCGAGCTGTTCGTGA |
| | ACTTCGACCCCCAGATCCTGATCCTGTTCCGGGAAACCGAGTGCATGGCC |
| | CAGATGGGGCTGGAAGTGAGCCCCCTGGCCACCAGCCTGTTCCAGAAGC |
| | GGGACCGGTACAAGCGGAACTTCAGCAACATGAAGATGATGCTGGCCGA |
| | GTACCAGCGCGTGAAGAGCAAGATCCCCGCCGCCATCGAGCAGCTGATC |
| | GTGCCCCACCTGGCCAAAGTGGACGAGGCCCTGCAGCCAGGACTGGCCG |
| | CCCTGACATGGACCAGCCTGAACATCGAGGCCTACCTGGAAAACACATTC |
| | GCCAAAATCAAGGACCTGGAACTGCTGCTGGACCGCGTGAACGACCTGA |
| | TCGAGTTCCGGATCGACGCCATCCTGGAAGAGATGAGCAGCACCCCCCTG |
| | TGCCAGCTGCCCCAGGAAGAACCCCTGACCTGCGAAGAGTTCCTGCAGAT |
| | GACCAAGGACCTGTGCGTGAACGGCGCCCAGATCCTGCACTTCAAGAGC |
| | AGCCTGGTGGAAGAAGCCGTGAACGAGCTCGTGAACATGCTGCTGGACG |
| | TGGAAGTGCTGAGCGAGGAAGAGAGCGAGAAGATCAGCAACGAGAACA |
| | GCGTGAACTACAAGAACGAGAGCAGCGCCAAGCGGGAAGAGGGCAACTT |
| | CGACACCCTGACCAGCAGCATCAACGCCAGAGCCAACGCCCTGCTGCTGA |
| | CCACCGTGACCCGGAAGAAAAAAGAAACCGAGATGCTGGGCGAAGAGGC |
| | CAGAGAGCTGCTGAGCCACTTCAACCACCAGAACATGGACGCCCTGCTGA |
| | AAGTGACACGGAACACCCTGGAAGCCATCCGGAAGCGGATCCACAGCAG |
| | CCACACCATCAACTTCCGGGACAGCAACAGCGCCAGCAACATGAAGCAG |
| | AACAGCCTGCCCATCTTCCGGGCCAGCGTGACACTGGCCATCCCCAACAT |
| | CGTGATGGCCCCCGCCCTGGAAGACGTGCAGCAGACACTGAACAAGGCC |
| | GTGGAATGCATCATCAGCGTGCCCAAGGGCGTGCGGCAGTGGAGCAGCG |
| | AACTGCTGAGCAAGAAGAAGATCCAGGAACGGAAAATGGCCGCCCTGCA |
| | GAGCAACGAGGACAGCGACAGCGACGTGGAAATGGGCGAGAACGAGCT |
| | GCAGGACACACTGGAAATCGCCAGCGTGAACCTGCCCATCCCCGTGCAG |
| | ACCAAGAACTACTACAAGAACGTGAGCGAAAACAAAGAAATCGTGAAGC |
| | TGGTGAGCGTGCTGAGCACCATCATCAACAGCACCAAGAAAGAAGTGAT |
| | CACCAGCATGGACTGCTTCAAGCGGTACAACCACATCTGGCAGAAGGGC |
| | AAAGAAGAGGCCATCAAGACCTTCATCACCCAGAGCCCCCTGCTGAGCG |
| | AGTTCGAGAGCCAGATCCTGTACTTCCAGAACCTGGAACAGGAAATCAAC |
| | GCCGAGCCCGAGTACGTGTGCGTGGGCAGCATCGCCCTGTACACCGCCGA |
| | CCTGAAGTTCGCCCTGACCGCCGAGACAAAGGCCTGGATGGTCGTGATCG |
| | GCCGGCACTGCAACAAAAAGTACAGAAGCGAGATGGAAAACATCTTCAT |
| | GCTGATCGAGGAATTCAACAAGAAACTGAACCGGCCCATCAAGGACCTG |
| | GACGACATCGAATCGCCATGGCCGCACTGAAAGAGATCAGAGAGGAAC |
| | AGATCAGCATCGACTTCCAAGTGGGCCCCATCGAGGAAAGCTACGCCCTG |
| | CTGAACAGATACGGACTGCTGATCGCCCGGGAAGAGATCGACAAGGTGG |
| | ACACCCTGCACTACGCCTGGGAGAAGCTGCTGGCCAGAGCCGGCGAGGT |
| | GCAGAACAAACTGGTGAGCCTGCAGCCCAGCTTCAAGAAAGAACTGATC |
| | AGCGCCGTGGAAGTGTTCCTGCAGGACTGCCACCAGTTCTACCTGGACTA |
| | CGACCTGAACGGCCCCATGGCCAGCGGCCTGAAACCCCAGGAAGCCAGC |
| | GACCGGCTGATCATGTTCCAGAACCAGTTCGACAACATCTACCGGAAGTA |
| | CATCACCTACACAGGCGGCGAGGAACTGTTCGGCCTGCCCGCCACACAGT |
| | ACCCCCAGCTGCTGGAAATCAAGAAGCAGCTGAACCTGCTGCAGAAGAT |
| | CTACACCCTGTACAACAGCGTGATCGAGACAGTGAACAGCTACTACGACA |
| | TCCTGTGGAGCGAAGTGAACATCGAGAAGATCAACAACGAACTGCTGGA |
| | ATTCCAGAACCGGTGCCGGAAGCTGCCCAGAGCACTGAAGGACTGGCAG |
| | GCCTTCCTGGACCTGAAGAAAATCATCGACGACTTCAGCGAGTGCTGCCC |
| | CCTGCTGGAGTACATGGCCAGCAAGGCCATGATGGAACGGCACTGGGAG |
| | AGAATCACCACACTGACCGGCCACAGCCTGGACGTGGGCAACGAGAGCT |
| | TCAAGCTGCGGAACATCATGGAAGCCCACTGCTGAAGTACAAAGAGGA |
| | AATCGAGGACATCTGCATCAGCGCCGTGAAAGAGCGGGACATCGAGCAG |
| | AAACTGAAACAAGTGATCAACGAGTGGGACAACAAGACCTTCACCTTCG |
| | GCAGCTTCAAGACCAGAGGCGAGCTGCTGCTGCGGGGCGACAGCACCAG |
| | CGAGATCATCGCCAACATGAAGACAGCCTGATGCTGCTGGGCAGCCTGC |
| | TGAGCAACCGGTACAACATGCCCTTCAAGGCCAGATCCAGAAATGGGT |
| | GCAGTACCTGAACAACACCACCGACATCATCGAGAGCTGGATGACCGTG |
| | CAGAACCTGTGGATCTACCTGGAAGCCGTGTTCGTGGGCGGCGACATCGC |
| | CAAGCAGCTGCCCAAAGAGGCCAAGGCGGTTCAGCAACATCGACAAGAGC |
| | TGGGTCAAGATCATGACCAGAGCCCACGAGGTGCCCAGCGTGGTGCAGT |
| | GCTGCGTGGGCGACGAAACACTGGGACAGCTGCTGCCCCACCTGCTGGAC |
| | CAGCTGGAAATCTGCCAGAAGAGCCTGACCGGCTACCTGGAAAAGAAAC |
| | GGCTGTGCTTCCCCCGGTTCTTCTTCGTGAGCGACCCCGCCCTGCTGGAAA |
| | TCCTGGGCCAGGCCAGCGACAGCCACACAATCCAGGCCCACTGCTGAAC |
| | GTGTTCGACAACATCAAGAGCGTGAAGTTCCACGAGAAATCTACGACC |
| | GGATCCTGAGCATCAGCAGCCAGGAAGGCGAGACAATCGAGCTGGACAA |
| | GCCCGTGATGGCCGAGGGAAACGTGGAAGTGTGGCTGAACAGCCTGCTG |
| | GAAGAGAGCCAGAGCAGCCTGCACCTCGTGATCAGACAGGCCGCCGCCA |
| | ACATCCAGGAAACCGGCTTCCAGCTGACCGAGTTCCTGAGCAGCTTCCCA |
| | GCACAAGTGGGACTGCTGGGCATCCAGATGATCTGGACCAGAGACAGCG |

| Construct | DNA sequence (from 5' to 3') |
|---|---|
| | AAGAGGCCCTGAGAAACGCCAAGTTCGACAAGAAAATCATGCAGAAAAC<br>AAACCAGGCATTCCTGGAACTGCTGAACACCCTGATCGACGTGACCACCC<br>GGGACCTGAGCAGCACCGAGAGAGTGAAGTACGAGACACTGATCACCAT<br>CCACGTGCACCAGCGGGACATCTTCGACGACCTGTGCCACATGCACATCA<br>AGAGCCCCATGGACTTCGAGTGGCTGAAGCAGTGCAGGTTCTACTTCAAC<br>GAGGACAGCGACAAGATGATGATCCACATCACCGACGTGGCCTTCATCTA<br>CCAGAACGAGTTCCTGGGCTGCACCGACCGCCTCGTGATCACCCCCCTGA<br>CCGACCGGTGCTACATCACACTGGCCCAGGCACTGGGCATGAGCATGGG<br>AGGCGCACCAGCAGGACCCGCCGGCACAGGCAAGACCGAAACCACCAAG<br>GACATGGGACGCTGCCTGGGCAAATACGTGGTGGTGTTCAACTGCAGCGA<br>CCAGATGGACTTCCGGGGCCTGGGCCGGATCTTCAAGGGCCTGGCACAGA<br>GCGGAAGCTGGGGCTGCTTCGACGAGTTCAACAGAATCGACCTGCCCGTG<br>CTGAGCGTGGCCGCACAGCAGATCAGCATCATCCTGACATGCAAAAAAG<br>AGCACAAGAAGAGCTTCATCTTCACCGACGGCGACAACGTGACCATGAA<br>CCCCGAGTTCGGCCTGTTCCTGACAATGAACCCCGGCTACGCCGGACGGC<br>AGGAACTGCCCGAGAACCTGAAGATCAACTTCCGGAGCGTGGCCATGAT<br>GGTGCCCGACCGGCAGATCATCATCAGAGTGAAACTGGCCAGCTGCGGCT<br>TCATCGACAACGTGGTGCTGGCCCGGAAGTTCTTCACACTGTACAAGCTG<br>TGCGAAGAACAGCTGAGCAAACAGGTGCACTACGACTTCGGCCTGAGGA<br>ACATCCTGAGCGTGCTGAGAACCCTGGGAGCCGCCAAGCGGGCCAACCC<br>CATGGACACCGAGAGCACAATCGTGATGCGGGTGCTGCGGGACATGAAC<br>CTGAGCAAGCTGATCGACGAGGACGAGCCCCTGTTCCTGAGCCTGATCGA<br>GGACCTGTTCCCCAACATCCTGCTGGACAAGGCCGGCTACCCCGAACTGG<br>AAGCCGCCATCAGCAGACAGGTGGAAGAGGCCGGCCTGATCAACCACCC<br>CCCCTGGAAACTGAAAGTGATCCAGCTGTTCGAGACACAGCGCGTGCGGC<br>ACGGCATGATGACACTGGGACCCAGCGGAGCCGGCAAGACCACCTGCAT<br>CCACACACTGATGCGGGCCATGACCGACTGCGGCAAGCCCCACCGCGAG<br>ATGCGGATGAAC |
| | CCCAAGGCCATCACCGCCCCCCAGATGTTCGGCAGACTGGACGTGGCCAC<br>CAACGACTGGACCGACGGCATCTTCAGCACCCTGTGGCGCAAGACCCTGC<br>GGGCCAAGAAGGGCGAGCACATCTGGATCATCCTGGACGGCCCCGTGGA<br>CGCCATCTGGATCGAGAACCTGAACAGCGTGCTGGACGACAACAAGACA<br>CTGACCCTGGCCAACGGCGACCGGATCCCCATGGCCCCCAACTGCAAGAT<br>CATCTTCGAGCCCCACAACATCGACAACGCCAGCCCCGCCACCGTGAGCA<br>GAAACGGCATGGTGTTCATGAGCAGCAGCATCCTGGACTGGAGCCCCATC<br>CTGGAAGGCTTCCTGAAGAAGCGGAGCCCCCAGGAAGCCAGGATCCTGA<br>GACAGCTGTACACCGAGAGCTTCCCCGACCTGTACCGGTTCTGCATCCAG<br>AACCTGGAGTACAAGATGGAAGTGCTGGAAGCCTTCGTGATCACCCAGA<br>GCATCAACATGCTGCAGGGCCTGATCCCCCTGAAAGAACAGGGCGGAGA<br>AGTGAGCCAGGCCCACCTGGGCAGACTGTTCGTGTTCGCCCTGCTGTGGA<br>GCGCCGGCGCCGCCCTGGAACTGGACGGAAGGCGGAGACTGGAACTGTG<br>GCTGCGGAGCAGACCCACCGGCACCCTGGAACTGCCCCCACCAGCCGGA<br>CCCGGCGACACCGCCTTCGACTACTACGTGGCCCCCGACGGCACCTGGAC<br>CCACTGGAACACCCGGACCCAGGAATACCTGTACCCCAGCGACACCACCC<br>CCGAGTACGGCAGCATCCTGGTGCCCAACGTGGACAACGTGCGGACCGA<br>CTTCCTGATCCAGACAATCGCCAAGCAGGGAAAGGCCGTGCTGCTGATCG<br>GCGAGCAGGGCACAGCCAAGACCGTGATCATCAAGGGCTTCATGAGCAA<br>GTACGACCCCGAGTGCCACATGATCAAGAGCTGAACTTCAGCAGCGCCA<br>CCACCCCACTGATGTTCCAGCGGACCATCGAGAGCTACGTGGACAAGCGG<br>ATGGGCACCACCTACGGCCCCCCAGCCGGCAAGAAAATGACCGTGTTCAT<br>CGACGACGTGAACATGCCCATCATCAACGAGTGGGGCGACCAAGTGACC<br>AACGAGATCGTGCGGCAGCTGATGGAACAGAACGGCTTCTACAACCTGG<br>AAAAGCCCGGCGAGTTCACCAGCATCGTGGACATCCAGTTCCTGGCCGCC<br>ATGATCCACCCCGGCGGCGGAAGAAACGACATCCCCCAGCGGCTGAAGC<br>GGCAGTTCAGCATCTTCAACTGCACCCTGCCCAGCGAGGCCAGCGTGGAC<br>AAGATCTTCGGCGTGATCGGCGTGGGCCACTACTGCACCCAGAGAGGCTT<br>CAGCGAGGAAGTGCGGGACAGCGTGACCAAGCTGGTGCCCCTGACAAGA<br>CGGCTGTGGCAGATGACCAAGATCAAGATGCTGCCCACCCCCGCCAAGTT<br>CCACTACGTGTTCAACCTGCGGGACCTGAGCAGAGTGTGGCAGGGAATGC<br>TGAACACCACCAGCGAAGTGATCAAAGAGCCCAACGACCTGCTGAAGCT<br>GTGGAAGCACGAGTGCAAGAGAGTGATCGCCGACCGGTTCACCGTGAGC<br>AGCGACGTGACATGGTTCGACAAGGCCCTGGTGAGCCTGGTGGAAGAGG<br>AATTCGGCGAAGAGAAGAAACTGCTGGTGGACTGCGGCATCGACACCTA<br>CTTCGTGGACTTCCTGCGCGACGCCCCGAAGCCGCCGGCGAGACAAGCG<br>AAGAGGCCGACGCCGAGACACCCAAGATCTACGAGCCCATCGAGAGCTT<br>CAGCCACCTGAAAGAAAGGCTGAACATGTTCCTGCAGCTGTACAACGAG<br>AGCATCGGGGAGCCGGCATGGACATGGTGTTCTTCGCCGACGCCATGGT<br>GCACCTCGTGAAGATCAGCAGAGTGATCCGGACCCCCAGGGCAACGCC<br>CTGCTCGTGGGAGTGGGAGGCAGCGGCAAGCAGAGCCTGACCAGACTGG<br>CCAGCTTCATCGCCGGCTACGTGAGCTTCCAGATCACCCTGACCCGGAGC<br>TACAACACCAGCAACCTGATGAAGACCTGAAGGTGCTGTACCGGACAG<br>CCGGCCAGCAGGGGAAGGGCATCACCTTCATCTTCACCGACAACGAGATC<br>AAGGACGAGAGCTTCCTGGAGTACATGAACAACGTGCTGAGCAGCCGGA<br>AGGTGAGCAACCTGTTCGCCCGGGACGAGATCGACGAGATCAACAGCGA<br>CCTGGCCAGCGTGATGAAGAAGAATTCCCCCGGTGCCTGCCCACAAACG<br>AGAACCTGCACGACTACTTCATGAGCAGAGTGCGGCAGAACCTGCACATC<br>GTGCTGTGCTTCAGCCCCGTGGGCGAGAAGTTCAGAAACCGGGCCCTGAA<br>GTTCCCCGCCCTGATCAGCGGCTGCACCATCGACTGGTTCAGCCGGTGGC |

TABLE 2-continued

| Construct | DNA sequence (from 5' to 3') |
|---|---|
| | CCAAGGACGCCCTGGTGGCCGTGAGCGAGCACTTCCTGACCAGCTACGAC |
| | ATCGACTGCAGCCTGGAAATCAAGAAAGAGGTGGTGCAGTGCATGGGCA |
| | GCTTCCAGGACGGCGTGGCCGAGAAATGCGTGGACTACTTCCAGCGGTTC |
| | CGGCGGAGCACCCACGTGACCCCCAAGAGCTACCTGAGCTTCATCCAGGG |
| | CTACAAGTTCATCTACGGCGAGAAGCACGTGGAAGTGCGCACACTGGCC |
| | AACCGGATGAACACCGGCCTGGAAAAACTGAAAGAGGCCAGCGAGAGCG |
| | TGGCCGCCCTGAGCAAAGAACTGGAAGCCAAAGAAAAAGAACTGCAGGT |
| | GGCCAACGACAAGGCCGACATGGTGCTGAAAGAAGTGACCATGAAGGCC |
| | CAGGCCGCCGAGAAAGTGAAAGCCGAGGTGCAGAAAGTGAAGGACCGG |
| | GCCCAGGCCATCGTGGACAGCATCAGCAAGGACAAGGCCATCGCCGAGG |
| | AAAAGCTGGAAGCAGCCAAGCCCGCCCTGGAAGAGGCAGAAGCCGCCCT |
| | GCAGACCATCCGGCCCAGCGACATCGCCACAGTGCGGACCCTGGGAAGG |
| | CCCCCCCACCTGATCATGCGGATCATGGACTGCGTGCTGCTGCTGTTCCA |
| | GAGAAAGGTGAGCGCCGTGAAGATCGACCTGGAAAAAGCTGCACCATG |
| | CCCAGCTGGCAGGAAAAGCCTGAAGCTGATGACCGCCGGCAACTTCCTGCA |
| | GAACCTGCAGCAGTTCCCCAAGGACACCATCAACGAGGAAGTGATCGAG |
| | TTCCTGAGCCCCTACTTCGAGATGCCCGACTACAACATCGAAACCGCCAA |
| | ACGCGTGTGCGGCAACGTGGCCGGACTGTGCAGCTGGACCAAGGCCATG |
| | GCCAGCTTCTTCAGCATCAACAAAGAGGTGCTGCCCCTGAAGGCCAACCT |
| | GGTGGTGCAGGAAAACCGGCACCTGCTGGCCATGCAGGACCTGCAGAAA |
| | GCCCAGGCCGAGCTGGACGACAAGCAGGCCGAGCTGGACGTGGTGCAGG |
| | CCGAGTACGAGCAGGCCATGACCGAGAAGCAGACCCTGCTGGAAGACGC |
| | AGAGCGGTGCAGACACAAGATGCAGACCGCCAGCACCCTGATCAGCGGA |
| | CTGGCCGGCGAAAAAGAGCGGTGGACCGAGCAGAGCCAGGAATTCGCCG |
| | CCCAGACCAAGCGGCTCGTGGGAGACGTGCTGCTGGCCACCGCCTTCCTG |
| | AGCTACAGCGGCCCCTTCAACCAGGAATTCAGGGACCTGCTGCTGAACGA |
| | CTGGCGGAAAGAGATGAAGGCCAGAAAGATCCCCTTCGGCAAGAACCTG |
| | AACCTGAGCGAGATGCTGATCGACGCCCCCACCATCAGCGAGTGGAACCT |
| | GCAGGGACTGCCCAACGACGACCTGAGCATCCAGAACGGAATCATCGTG |
| | ACCAAAGCCAGCAGATACCCCCTGCTGATCGACCCCCAGACACAGGGCA |
| | AGATCTGGATCAAGAACAAAGAGAGCCGGAACGAGCTGCAGATCACCAG |
| | CCTGAACCACAAGTACTTCCGGAACCACCTGGAAGACAGCCTGAGCCTGG |
| | GCAGGCCACTGCTGATCGAGGACGTGGGCGAGGAACTGGACCCAGCCCT |
| | GGACAACGTGCTGGAACGGAACTTCATCAAGACCGGCAGCACCTTCAAA |
| | GTGAAAGTGGGCGACAAAGAAGTGGACGTGCTGGACGGCTTCCGGCTGT |
| | ACATCACCACCAAGCTGCCCAACCCCGCCTACACCCCCGAGATCAGCGCC |
| | CGGACCAGCATCATCGACTTCACCGTGACAATGAAGGGACTGGAAGACC |
| | AGCTGCTGGACGCGTGATCCTGACAGAGAAGCAGGAACTGGAAAAAGA |
| | ACGGACCCACCTGATGAAGACGTGACCGCCAACAAGCGGCGGATGAAG |
| | GAACTGGAAGACAACCTGCTGTACAGGCTGACCAGCACCCAGGGCACC |
| | TGGTGGAAGACGAGAGCCTGATCGTGGTGCTGAGCAACACCAAGCGGAC |
| | CGCAGAGGAAGTGACCCAGAAGCTGGAAATCAGCGCCGAGACAGAGGTG |
| | CAGATCAACAGCGCCAGAGAAGAGTACCGGCCCGTGGCCACCCGGGGAA |
| | GCATCCTGTACTTCCTGATCACCGAGATGCGGCTCGTGAACGAGATGTAC |
| | CAGACCAGCCTGCGGCAGTTCCTGGGCCTGTTCGACCTGAGCCTGGCCAG |
| | AAGCGTGAAGAGCCCCATCACCAGCAAGAGAATCGCCAACATCATCGAG |
| | CACATGACCTACGAGGTGTACAAATACGCCGCCAGAGGCCTGTACGAGG |
| | AACACAAGTTCCTGTTCACACTGCTGCTGACCCTGAAGATCGACATCCAG |
| | CGGAACAGAGTGAAGCACGAAGAGTTCCTGACACTGATCAAGGGGGGAG |
| | CCAGCCTGGACCTGAAGGCCTGCCCCCCCAAGCCCAGCAAGTGGATCCTG |
| | GACATCACCTGGCTGAACCTGGTGGAACTGAGCAAGCTGAGACAGTTCA |
| | GCGACGTGCTGGACCAGATCAGCCGCAACGAGAAGATGTGGAAGATCTG |
| | GTTCGACAAAGAGAACCCCGAGGAAGAACCCCTGCCCAACGCCTACGAC |
| | AAGAGCCTGGACTGCTTCCGGCGGCTGCTGCTGATCAGAAGCTGGTGCCC |
| | CGACCGGACAATCGCCCAGGCCCGCAAGTACATCGTGGACAGCATGGGA |
| | GAGAAGTACGCCGAGGGCGTGATCCTGGACCTGGAAAAGACCTGGGAGG |
| | AAAGCGACCCCAGAACCCCCCTGATCTGCCTGCTGAGCATGGGCAGCGAC |
| | CCCACCGACAGCATCATCGCCCTGGGCAAGAGACTGAAGATCGAGACAA |
| | GATACGTGAGCATGGGCCAGGGCCAGGAAGTGCACGCCAGAAAGCTGCT |
| | GCAGCAGACCATGGCCAACGGCGGCTGGGCCCTGCTGCAGAACTGCCAC |
| | CTGGGGCTGGACTTCATGGACGAACTGATGGACATCATCATCGAGACAGA |
| | GCTGGTGCACGACGCCTTCAGACTGTGGATGACCACCGAGGCCCACAAGC |
| | AGTTCCCCATCACCCTGCTGCAGATGAGCATCAAGTTCGCCAACGACCCC |
| | CCCCAGGGACTGAGAGCCGGCCTGAAGAGAACCTACAGCGGCGTGAGCC |
| | AGGACCTGCTGGACGTGAGCAGCGGCAGCCAGTGGAAGCCCATGCTGTA |
| | CGCCGTGGCATTCCTGCACAGCACCGTGCAGGAACGGCGGAAGTTCGGC |
| | GCCCTGGGATGAACATCCCCTACGAGTTCAACCAGGCCGACTTCAACGC |
| | CACCGTGCAGTTCATCCAGAACCACCTGGACGACATGGACGTGAAGAAA |
| | GGGGTGAGCTGGACAACATCCGGTACATGATCGGAGAGATCCAGTACG |
| | GCGGCAGAGTGACCGACGACTACGACAAGAGGCTGCTGAACACCTTCGC |
| | CAAAGTGTGGTTCAGCGAGAACATGTTCGGCCCCGACTTCAGCTTCTACC |
| | AGGGCTACAACATCCCCAAGTGCAGCACCGTGGACAACTACCTGCAGTAC |
| | ATCCAGAGCCTGCCCCGCCTACGACAGCCCCGAGGTGTTCGGACTGCACC |
| | CAACGCCGACATCACCTACCAGAGCAAACTGGCCAAGGACGTGCTGGAC |
| | ACCATCCTGGGCATCCAGCCCAAGGACACCAGCGGCGGAGGCGACGAAA |
| | CCCGGGAAGCAGTGGTGGCCAGACTGGCCGACGACATGCTGGAAAAGCT |
| | GCCCCCCGACTACGTGCCCTTCGAAGTGAAAGAACGCCTGCAGAAGATG |
| | GGCCCCTTCCAGCCCATGAACATCTTCCTGAGGCAGGAAATCGACCGGAT |

TABLE 2-continued

| Construct | DNA sequence (from 5' to 3') |
|---|---|
| | GCAGCGGGTGCTGAGCCTCGTGCGGAGCACACTGACCGAGCTGAAACTG
GCCATCGACGGCACCATCATCATGAGCGAGAACCTGCGGGACGCACTGG
ACTGCATGTTCGACGCCAGAATCCCCGCATGGTGGAAAAAGGCCAGCTG
GATCAGCAGCACCCTGGGCTTCTGGTTCACCGAACTGATCGAGAGAAACA
GCCAGTTCACCAGCTGGGTGTTCAACGGCAGACCCCACTGCTTCTGGATG
ACCGGCTTCTTCAACCCACAAGGCTTCCTGACAGCAATGCGCCAGGAAAT
CACCAGAGCCAACAAGGGCTGGGCCCTGGACAACATGGTGCTGTGCAAC
GAAGTGACCAAGTGGATGAAGGACGACATCAGCGCCCCCCCCACAGAGG
GCGTGTACGTGTACGGCCTGTACCTGGAAGGCGCCGGATGGGACAAGAG
AAACATGAAGCTGATCGAGAGCAAGCCCAAGGTGCTGTTCGAGCTGATG
CCCGTGATCAGGATCTACGCCGAGAACAACACCCTGAGGGACCCCCGGTT
CTACAGCTGCCCCATCTACAAGAAACCCGTGCGCACCGACCTGAACTACA
TCGCCGCCGTGGACCTGAGGACAGCCCAGACACCCGAGCACTGGGTGCT
GAGAGGCGTGGCACTGCTGTGCGACGTGAAGTGA (SEQ ID NO: 17) |
| DNAH5 Altered Nucleotide Usage 2 | ATGTTCAGAATCGGCAGACGGCAGCTGTGGAAGCACAGCGTGACCAGAG
TGCTGACCCAGCGGCTGAAGGGCGAGAAAGAGGCCAAGAGAGCCCTGCT
GGACGCCCGGCACAATTACCTGTTTGCCATCGTGGCCAGCTGCCTGGACC
TGAACAAGACCGAGGTGGAAGATGCCATCCTGGAAGGCAACCAGATCGA
GCGGATCGACCAGCTGTTTGCCGTGGGCGGACTGCGGCACCTGATGTTCT
ATTATCAAGACGTGAAGAGGCCGAGACAGGCCAGCTGGGATCTCTGGG
CGGAGTGAATCTGGTGTCCGGCAAGATCAAGAAACCCAAGGTGTTCGTG
ACCGAGGGCAACGACGTGGCCCTGACAGGCGTGTGCGTGTTCTTCATCAG
AACCGACCCCAGCAAGGCCATCACCCCCGACAACATCCACCAGGAAGTG
TCCTTCAACATGCTGGATGCCGCCGATGGCGGCCTGCTGAATTCTGTGCG
GAGACTGCTGAGCGACATCTTCATCCCCGCCCTGAGAGCCACATCTCACG
GCTGGGGAGAGCTGGAAGGACTGCAGGACGCCGCCAATATCCGGCAGGA
ATTTCTGAGCAGCCTGGAAGGATTCGTGAACGTGCTGTCTGGCGCCCAGG
AAAGCCTGAAAGAAAAAGTGAACCTGCGGAAGTGCGATATCCTGGAACT
GAAAACCCTGAAAGAGCCCACCGACTACCTGACCCTGGCCAACAACCCT
GAGACACTGGGCAAGATCGAGGACTGCATGAAAGTGTGGATCAAGCAGA
CCGAACAGGTGCTGGCCGAGAACAACCAGCTGCTGAAAGAAGCCGACGA
CGTGGGCCAAGAGCCGAGCTGGAACACTGGAAGAAGCGGCTGAGCAAG
TTCAACTACCTGCTGGAACAGCTGAAGTCCCCCGACGTGAAGGCCGTGCT
GGCTGTGCTGGCAGCCGCCAAGAGCAAACTGCTGAAAACCTGGCGCGAG
ATGGACATCCGGATCACCGACGCCACCAACGAGGCCAAGGACAACGTGA
AGTACCTGTACACCCTGGAAAAGTGCTGCGACCCCCTGTACAGCAGCGAC
CCTCTGAGCATGATGGACGCCATCCCTACCCTGATCAACGCCATCAAGAT
GATCTACAGCATCAGCCACTACTACAACACCAGCGAGAAGATCACCAGC
CTGTTCGTGAAAGTGACCAATCAGATCATCAGCGCCTGCAAGGCCTACAT
CACCAACAACGGCACCGCCAGCATCTGGAACCAGCCCCAGGATGTGGTG
GAAGAGAAGATCCTGTCTGCCATCAAGCTGAAGCAGGAATACCAGCTGT
GTTTTCACAAGACCAAGCAGAAGCTGAAACAGAACCCCAACGCCAAGCA
GTTCGACTTCAGCGAGATGTATATCTTCGGCAAGTTCGAGACATTCCACC
GGCGGCTGGCCAAGATCATCGACATCTTTACCACCCTGAAAACATACAGC
GTGCTGCAGGACAGCACCATCGAGGGCCTGGAAGATATGGCCACCAAGT
ACCAGGGCATTGTGGCCACCATCAAGAAGAAAGAGTACAACTTCCTGGA
CCAGCGCAAGATGGACTTCGACCAGGACTACGAGGAATTCTGCAAGCAG
ACAAACGACCTGCACAACGAGCTGCGCAAGTTTATGGACGTGACCTTCGC
CAAGATCCAGAACACCAACCAGGCCCTGCGGATGCTGAAGAAGTTTGAG
AGACTGAACATCCCCAACCTGGGCATCGACGATAAGTACCAGCTGATCCT
GGAAAACTACGGCGCCGACATCGACATGATCAGCAAGCTGTACACAAAG
CAGAAGTACGACCCCCCCCTGGCCCGGAATCAGCCTCCTATCGCCGGCAA
AATCCTGTGGGCTAGACAGCTGTTTCACCGGATCCAGCAGCCCATGCAGC
TGTTCCAGCAGCACCCTGCCGTGCTGAGCACAGCCGAGGCCAAACCCATC
ATCCGGTCCTACAACCGGATGGCCAAGGTGCTGCTGGAATTCGAGGTGCT
GTTCCACCGGGCCTGGCTGCGGCAGATCGAAGAGATTCACGTGGGACTGG
AAGCCAGCCTGCTCGTGAAGGCTCCTGGAACCGGCGAGCTGTTTGTGAAC
TTCGACCCCCAGATCCTGATCCTGTTCCGGGAAACCGAGTGCATGGCCCA
GATGGGCTGGAAGTGTCCTCTGGCCACCTCCCTGTTCCAGAAGCGGG
ACCGGTACAAGCGGAACTTCAGCAACATGAAGATGATGCTGGCTGAGTA
CCAGCGCGTGAAGTCCAAGATCCCCGCTGCCATCGAGCAGCTGATCGTGC
CTCACCTGGCCAAAGTGGACGAGGCCCTGCAGCCAGGACTGGCCGCTCTG
ACATGGACCAGCCTGAACATCGAGGCCTATCTGGAAAACACATTCGCCAA
AATCAAGGATCTGGAACTGCTGCTGGACCGCGTGAACGACCTGATCGAGT
TCCGGATCGACGCCATTCTGGAAGAGATGTCCAGCACCCCCCTGTGTCAG
CTGCCCCAGGAAGAACCCCTGACCTGCGAAGAGTTCCTGCAGATGACCAA
GGACCTGTGCGTGAACGGCGCCCAGATTCTGCACTTCAAGTCCAGCCTGG
TGGAAGAAGCCGTGAACGAGCTCGTGAATATGCTGCTGGATGTGGAAGT
GCTGAGCGAGGAAGAGTCCGAGAAGATCTCCAACGAGAACAGCGTGAAC
TACAAGAACGAGTCCAGCGCCAAGCGGGAAGAGGGCAACTTCGACACCC
TGACCAGCTCCATCAATGCCAGAGCCAACGCCCTGCTGCTGACCACCGTG
ACCCGGAAGAAAAAGAACCGAGATGCTGGGCGAAGAGGCTAGAGAG
CTGCTGTCCCACTTCAACCACCAGAACATGGATGCCCTGCTGAAAGTGAC
ACGGAATACCCTGGAAGCCATCCGGAAGCGGATCCACAGCAGCCACACC
ATCAACTTCCGGGACAGCAACAGCGCCAGCAATATGAAGCAGAACAGCC
TGCCCATCTTCCGGGCCTCCGTGACACTGGCCATCCCCAATATCGTGATG
GCCCCTGCTCTGGAAGATGTGCAGCAGACACTGAACAAGGCCGTGGAAT |

TABLE 2-continued

| Construct | DNA sequence (from 5' to 3') |
|---|---|
| | GCATCATCTCCGTGCCCAAGGGCGTGCGGCAGTGGTCTAGCGAACTGCTG |
| | TCCAAGAAGAAGATCCAGGAACGGAAAATGGCCGCCCTGCAGTCTAACG |
| | AGGACAGCGACTCCGACGTGGAAATGGGCGAGAATGAGCTGCAGGATAC |
| | ACTGGAAATCGCCTCTGTGAATCTGCCCATCCCCGTGCAGACCAAGAACT |
| | ACTATAAGAACGTGTCCGAAAACAAAGAAATCGTGAAGCTGGTGTCTGT |
| | GCTGTCCACCATCATCAACAGCACCAAGAAAGAAGTGATCACCTCCATGG |
| | ACTGCTTCAAGCGGTACAACCACATCTGGCAGAAGGGCAAAGAAGAGGC |
| | CATTAAGACCTTCATCACCCAGAGCCCCCTGCTGTCCGAGTTCGAGTCTC |
| | AGATCCTGTACTTCCAGAACCTGGAACAGGAAATCAACGCCGAGCCCGA |
| | GTACGTGTGTGTGGGCTCTATCGCCCTGTATACCGCCGACCTGAAGTTCG |
| | CCCTGACCGCCGAGACAAAGGCCTGGATGGTCGTGATCGGCCGGCACTGC |
| | AACAAAAAGTACAGATCCGAGATGGAAACATCTTTATGCTGATTGAGG |
| | AATTCAACAAGAAACTGAACCGGCCCATTAAGGACCTGGACGACATCAG |
| | AATCGCCATGGCCGCACTGAAAGAGATCAGAGAGGAACAGATCAGCATC |
| | GACTTCCAAGTGGGCCCCATCGAGGAAAGCTACGCTCTGCTGAACAGATA |
| | CGGACTGCTGATCGCCCGGGAAGAGATCGACAAGGTGGACACCCTGCAC |
| | TACGCCTGGGAGAAGCTGCTGGCTAGAGCCGGCGAGGTGCAGAACAAAC |
| | TGGTGTCTCTGCAGCCCAGCTTTAAGAAAGAACTGATCTCCGCCGTGGAA |
| | GTGTTTCTGCAGGACTGCCACCAGTTCTACCTGGACTACGACCTGAACGG |
| | CCCCATGGCCTCTGGCCTGAAACCTCAGGAAGCCTCCGACCGGCTGATTA |
| | TGTTTCAGAACCAGTTCGACAATATCTACCGGAAGTACATCACCTACACA |
| | GGCGGCGAGGAACTGTTCGGCCTGCCTGCCACACAGTACCCCCAGCTGCT |
| | GGAAATCAAGAAGCAGCTGAACCTGCTGCAGAAGATCTACACCCTGTAC |
| | AACTCCGTGATCGAGACAGTGAACAGCTACTACGACATCCTGTGGAGCGA |
| | AGTGAACATTGAGAAGATTAACAATGAACTGCTGGAATTTCAGAACCGGT |
| | GCCGGAAGCTGCCCAGAGCACTGAAGGATTGGCAGGCCTTTCTGGATCTG |
| | AAGAAAATCATCGACGACTTCTCCGAGTGCTGCCCTCTGCTGGAGTACAT |
| | GGCCTCCAAGGCCATGATGGAACGGCACTGGGAGAGAATCACCACACTG |
| | ACCGGCCACAGCCTGGACGTGGGCAACGAGAGCTTCAAGCTGCGGAACA |
| | TCATGGAAGCCCCACTGCTGAAGTACAAAGAGGAAATCGAGGACATCTG |
| | TATCAGCGCCGTGAAAGAGCGGGATATCGAGCAGAAACTGAAACAAGTG |
| | ATCAACGAGTGGGACAACAAGACCTTTACCTTCGGCAGCTTCAAGACCAG |
| | AGGCGAGCTGCTGCTGCGGGGCGATAGCACCTCTGAGATCATTGCCAACA |
| | TGGAAGATAGCCTGATGCTGCTGGGCTCCCTGCTGAGCAACCGGTATAAC |
| | ATGCCCTTCAAGGCTCAGATTCAGAAATGGGTGCAGTACCTGAGCAACTC |
| | CACCGACATCATCGAGTCCTGGATGACCGTGCAGAACCTGTGGATCTACC |
| | TGGAAGCCGTGTTCGTGGGCGGCGACATTGCCAAGCAGCTGCCCAAAGA |
| | GGCTAAGCGGTTCTCCAACATCGACAAGAGCTGGGTCAAGATCATGACCA |
| | GAGCCCACGAGGTGCCCAGCGTGGTGCAGTGCTGTGTGGGCGACGAAAC |
| | ACTGGGACAGCTGCTGCCTCATCTGCTGGACCAGCTGGAAATCTGCCAGA |
| | AGTCCCTGACCGGCTACCTGGAAAAGAAACGGCTGTGTTTCCCCCGGTTC |
| | TTCTTCGTGTCCGACCCCGCCCTGCTGGAAATTCTGGGCCAGGCCAGCGA |
| | CTCACACACAATTCAGGCCCATCTGCTGAATGTGTTCGATAACATCAAGA |
| | GCGTGAAGTTCCACGAGAAAATCTACGACCGGATCCTGAGCATCAGCTCC |
| | CAGGAAGGCGAGACAATCGAGCTGGACAAGCTGTGATGGCCGAGGGAA |
| | ACGTGGAAGTGTGGCTGAACAGCCTGCTGGAAGAGTCCCAGAGCAGCCT |
| | GCACCTCGTGATCAGACAGGCCGCTGCCAACATCCAGGAAACCGGCTTTC |
| | AGCTGACCGAGTTCCTGTCCAGCTTCCCAGCACAAGTGGGACTGCTGGGC |
| | ATCCAGATGATTTGGACCAGAGACTCCGAAGAGGCCCTGAGAAACGCCA |
| | AGTTCGATAAGAAAATTATGCAGAAAACAAATCAGGCATTTCTGGAACTG |
| | CTGAACACCCTGATCGACGTGACCACCCGGGACCTGAGCAGCACCGAGA |
| | GAGTGAAGTACGAGACACTGATCACCATCCACGTGCACCAGCGGGACAT |
| | CTTCGACGACCTGTGCCACATGCACATCAAGTCTCCCATGGATTTCGAGT |
| | GGCTGAAGCAGTGCAGGTTCTACTTCAACGAGGACTCCGACAAGATGATG |
| | ATCCACATCACCGATGTGGCCTTTATCTATCAGAATGAGTTCCTGGGCTGT |
| | ACCGATCGCCTCGTGATTACCCCCCTGACCGACCGGTGTTACATCACACT |
| | GGCCCAGGCACTGGGCATGTCTATGGGAGGCGCACCAGCAGGACCTGCC |
| | GGCACAGGCAAGACCGAAACCACCAAGGACATGGGACGCTGCCTGGGCA |
| | ATACGTGGTGGTGTTCAACTGCAGCGACCAGATGGATTTCCGGGGCCTG |
| | GGCCGGATCTTTAAGGGCCTGGCACAGAGCGGAAGCTGGGGCTGCTTCG |
| | ACGAGTTCAACAGAATCGACCTGCCCGTGCTGTCCGTGGCCGCACAGCAG |
| | ATCTCCATCATCCTGACATGCAAAAAGAGCACAAGAAGTCCTTCATCTT |
| | CACCGACGGCGACAATGTGACCATGAACCCCGAGTTTGGCCTGTTCCTGA |
| | CAATGAACCCTGGCTACGCCGGACGGCAGGAACTGCCCGAGAACCTGAA |
| | GATCAACTTTCGGAGTGTGGCTATGATGGTGCCCGACCGGCAGATCATTA |
| | TCAGAGTGAAACTGGCCTCCTGCGGCTTCATCGACAACGTGGTGCTGGCT |
| | CGGAAGTTCTTCACACTGTACAAGCTGTGCGAAGAACAGCTGAGTAAACA |
| | GGTGCACTACGACTTCGGCCTGAGGAACATCCTGAGCGTGCTGAGAACTC |
| | TGGGAGCCGCTAAGCGGGCCAACCCCATGGATACCGAGAGCACAATCGT |
| | GATGCGGGTGCTGCGGGACATGAACCTGTCCAAGCTGATCGATGAGGAC |
| | GAGCCCCTGTTTCTGTCTCTGATCGAGGATCTGTTTCCCAACATTCTGCTG |
| | GATAAGGCCGGCTACCCCGAACTGGAAGCTGCTATCAGCAGACAGGTGG |
| | AAGAGGCTGGCCTGATCAACCACCCCCCTGGAAACTGAAAGTGATCCA |
| | GCTGTTCGAGACACAGCGCGTGCGGCACGGCATGATGACACTGGGACCT |
| | AGCGGAGCCGGCAAGACCACCTGTATCCACACACTGATGCGGGCCATGA |
| | CCGATTGCGGCAAGCCCCACCGCGAGATGCGGATGAAC |
| | CCCAAGGCCATTACCGCCCCTCAGATGTTCGGCAGACTGGACGTGGCCAC |
| | CAACGACTGGACCGACGGCATCTTCAGCACCCTGTGGCGCAAGACCCTGC |

TABLE 2-continued

| Construct | DNA sequence (from 5' to 3') |
|---|---|
| | GGGCCAAGAAGGGCGAGCACATCTGGATCATCCTGGACGGCCCCGTGGA
CGCCATCTGGATTGAGAACCTGAACAGCGTGCTGGACGACAACAAGACA
CTGACCCTGGCCAACGGCGACCGGATCCCCATGGCCCCCAACTGCAAGAT
CATCTTCGAGCCCCACAACATCGACAACGCCAGCCCTGCCACCGTGTCCA
GAAACGGCATGGTGTTCATGAGCAGCAGCATCCTGGATTGGAGCCCTATC
CTGGAAGGCTTCCTGAAGAAGCGGAGCCCCCAGGAAGCCGAGATCCTGA
GACAGCTGTACACCGAGAGCTTCCCCGACCTGTACCGGTTCTGCATCCAG
AATCTGGAGTACAAGATGGAAGTGCTGGAAGCCTTTGTGATCACCCAGAG
CATCAACATGCTGCAGGGCCTGATCCCCCTGAAAGAACAGGGCGGAGAA
GTGTCCCAGGCCCACCTGGGCAGACTGTTCGTGTTTGCCCTGCTGTGGAG
CGCTGGCGCCGCTCTGGAACTGGATGGAAGGCGGAGACTGGAACTGTGG
CTGCGGAGCAGACCTACCGGCACCCTGGAACTGCCTCCACCAGCTGGACC
TGGCGACACCGCCTTCGATTACTACGTGGCCCCTGACGGCACCTGGACCC
ACTGGAATACCCGGACCCAGGAATACCTGTACCCCAGCGACACCACCCCC
GAGTACGGCTCTATCCTGGTGCCCAACGTGGACAACGTGCGGACCGACTT
CCTGATCCAGACAATCGCCAAGCAGGGAAAGGCCGTGCTGCTGATCGGC
GAGCAGGGCACAGCCAAGACCGTGATCATCAAGGGCTTTATGTCTAAGTA
CGACCCCGAGTGCCACATGATCAAGAGCCTGAACTTCAGCTCCGCCACCA
CCCCACTGATGTTCCAGCGGACCATCGAGAGCTATGTGGACAAGCGGATG
GGCACCACCTACGCCCTCCAGCCGGCAAGAAAATGACCGTGTTCATCGA
CGACGTGAACATGCCCATCATCAACGAGTGGGGCGACCAAGTGACCAAC
GAGATCGTGCGGCAGCTGATGAACAGAACGGCTTCTACAACCTGGAAA
AGCCCGGCGAGTTCACCTCTATCGTGGACATTCCAGTTTCTGGCCGCCATG
ATCCACCCTGGCGGCGAAGAAACGACATCCCCCAGCGGCTGAAGCGGC
AGTTCAGCATCTTCAACTGCACCCTGCCCAGCGAGGCCAGCGTGGACAAG
ATCTTTGGCGTGATCGGCGTGGGCCACTACTGCACCCAGAGAGGCTTCAG
CGAGGAAGTGCGGGACAGCGTGACCAAGCTGGTGCCTCTGACAAGACGG
CTGTGGCAGATGACCAAGATCAAGATGCTGCCCACCCCCGCCAAGTTCCA
CTACGTGTTCAACCTGCGGGACCTGAGCAGAGTGTGGCAGGGAATGCTGA
ACACCACCAGCGAAGTGATCAAAGAGCCCAACGACCTGCTGAAGCTGTG
GAAGCACGAGTGCAAGAGAGTGATCGCCGACCGGTTCACCGTGTCTAGC
GACGTGACATGGTTCGACAAGGCCCTGGTGTCCCTGGTGGAAGAGGAATT
CGGCAAGAGAAGAAACTGCTGGTGGACTGCGGCATCGATACCTACTTC
GTGGACTTCCTGCGCGACGCCCCTGAAGCCGCTGGCGAGACAAGTGAAG
AGGCCGACGCCGAGACACCCAAGATCTACGAGCCCATCGAGTCCTTCAGC
CATCTGAAAGAAAGGCTGAATATGTTCCTGCAGCTGTATAACGAGTCCAT
CCGGGGAGCCGGCATGGATATGGTGTTCTTTGCCGACGCCATGGTGCACC
TCGTGAAGATCAGCAGAGTGATCCGGACCCCCAGGGCAACGCTCTGCTC
GTGGGAGTGGGAGGCTCTGGCAAGCAGAGCCTGACCAGACTGGCCAGCT
TTATCGCCGGCTACGTGTCCTTCCAGATCACCCTGACCCGGTCCTACAACA
CCAGCAACCTGATGGAAGATCTGAAGGTGCTGTACCGGACAGCCGGCCA
GCAGGGGAAGGGCATCACCTTCATCTTCACCGACAATGAGATCAAGGAC
GAGTCTTTCCTGGAGTATATGAACAATGTGCTGAGCAGCGGCGAGGTGTC
CAACCTGTTCGCCCGGGACGAGATCGACGAGATTAACAGCGACCTGGCCT
CCGTGATGAAGAAAGAATTCCCCCGGTGCCTGCCCACAAACGAGAACCT
GCACGACTACTTCATGTCCAGAGTGCGGCAGAATCTGCACATCGTGCTGT
GCTTCAGCCCCGTGGGCGAGAAGTTCAGAAACCGGGCCCTGAAGTTCCCC
GCCCTGATCAGCGGCTGCACCATCGACTGGTTCAGCCGGTGGCCTAAGGA
TGCCCTGGTGGCCGTGTCCGAGCACTTTCTGACCAGCTACGACATCGACT
GCAGCCTGGAAATCAAGAAAGAGGTGGTGCAGTGCATGGCAGCTTCCA
GGACGGCGTGGCCGAGAAATGCGTGGACTACTTCCAGCGGTTCCGGCGG
AGCACCCACGTGACCCCTAAGAGCTACCTGAGCTTCATCCAGGGCTACAA
GTTCATCTACGGCGAGAAGCACGTGGAAGTGCGCACACTGGCCAACCGG
ATGAACACCGGCCTGGAAAAACTGAAAGAGGCCTCCGAGAGCGTGGCCG
CCCTGAGCAAAGAACTGGAAGCCAAAGAAAAAGAACTGCAGGTGGCCAA
CGATAAGGCCGACATGGTGCTGAAAGAAGTGACCATGAAGGCCCAGGCC
GCCGAGAAAGTGAAAGCCGAGGTGCAGAAAGTGAAGGACCGGGCCCAG
GCCATCGTGGACTCCATCAGCAAGGACAAGGCCATTGCCGAGGAAAAGC
TGGAAGCAGCCAAGCCCGCCCTGGAAGAGGCAGAAGCTGCTCTGCAGAC
CATCCGGCCCTCCGATATTGCCACAGTGCGGACCCTGGGAAGGCCCCCTC
ACCTGATCATGCGGATCATGGACTGTGTGCTGCTGTTCCAGAGAAAG
GTGTCCGCCGTGAAGATCGACCTGGAAAAATCCTGCACCATGCCTAGCTG
GCAGGAATCCCTGAAGCTGATGACCGCCGGCAACTTCCTGCAGAACCTGC
AGCAGTTCCCCAAGGACACCATCAATGAGGAAGTGATCGAGTTCCTGAGC
CCCTACTTCGAGATGCCCGACTACAATATCGAAACCGCCAAACGCGTGTG
CGGCAACGTGGCCGGACTGTGCTCTTGGACCAAGGCTATGGCTAGCTTCT
TTAGCATTAACAAAGAGGTGCTGCCTCTGAAGGCCAACCTGGTGGTGCAG
GAAAACCGGCATCTGCTGGCCATGCAGGACCTGCAGAAAGCCCAGGCCG
AGCTGGACGATAAGCAGGCTGAGCTGGATGTGGTGCAGGCCGAGTACGA
GCAGGCCATGACCGAGAAGCAGACCCTGCTGGAAGATGCAGAGCGGTGC
AGACACAAGATGCAGACCGCCAGCACCCTGATCTCTGGACTGGCCGGCG
AAAAAGAGCGGTGGACCGAGCAGTCCCAGGAATTCGCCGCCCAGACCAA
GCGGCTCGTGGGAGATGTGCTGCTGGCCACCGCCTTTCTGAGCTACGACG
GCCCCTTCAATCAGGAATTCAGGGACCTGCTGCTGAACGACTGGCGGAAA
GAGATGAAGGCCAGAAAGATCCCCTTCGGCAAGAATCTGAACCTGAGCG
AGATGCTGATCGACGCCCCCACCATCTCCGAGTGGAATCTGCAGGGACTG
CCCAACGATGACCTGTCCATCCAGAACGGAATCATCGTGACCAAAGCCTC
CAGATACCCCCTGCTGATTGACCCCCAGACACAGGGCAAGATTTGGATCA |

TABLE 2-continued

| Construct | DNA sequence (from 5' to 3') |
|---|---|
| | AGAACAAAGAGAGCCGGAACGAGCTGCAGATCACCAGCCTGAACCACAA
GTACTTCCGGAACCACCTGGAAGATAGCCTGAGCCTGGGCAGGCCACTGC
TGATCGAGGATGTGGGCGAGGAACTGGACCCAGCCCTGGATAACGTGCT
GGAACGGAACTTCATCAAGACCGGCTCCACCTTCAAAGTGAAAGTGGGC
GACAAAGAAGTGGACGTGCTGGATGGCTTCCGGCTGTACATCACCACCAA
GCTGCCTAACCCCGCCTACACCCCTGAGATCAGCGCCCGGACCAGCATCA
TCGACTTCACCGTGACAATGAAGGGACTGGAAGATCAGCTGCTGGGACG
CGTGATCCTGACAGAGAAGCAGGAACTGGAAAAAGAACGGACCCATCTG
ATGGAAGATGTGACCGCCAACAAGCGGCGGATGAAGGAACTGGAAGATA
ACCTGCTGTACAGGCTGACCAGCACCCAGGGCAGTCTGGTGGAAGATGA
GAGCCTGATCGTGGTGCTGTCCAACACCAAGCGGACCGCAGAGGAAGTG
ACCCAGAAGCTGGAAATCAGCGCCGAGACAGAGGTGCAGATCAACAGCG
CCAGAGAAGAGTACCGGCCTGTGGCCACCCGGGGATCCATCCTGTACTTT
CTGATCACCGAGATGCGGCTCGTGAACGAGATGTACCAGACCAGCCTGCG
GCAGTTCCTGGGCCTGTTCGATCTGTCCCTGGCCAGAAGCGTGAAGTCCC
CCATCACCAGCAAGAGAATCGCCAACATCATCGAGCACATGACCTACGA
GGTGTACAAATACGCCGCCAGAGGCCTGTACGAGGAACACAAGTTTCTGT
TCACACTGCTGCTGACCCTGAAGATCGATATCCAGCGGAACAGAGTGAAG
CACGAAGAGTTTCTGACACTGATCAAGGGGGGAGCCTCCCTGGACCTGAA
GGCCTGTCCTCCCAAGCCCAGCAAGTGGATCCTGGACATCACCTGGCTGA
ATCTGGTGGAACTGAGCAAGCTGAGACAGTTCTCCGATGTGCTGGACCAG
ATCAGCCGCAACGAGAAGATGTGGAAGATTTGGTTTGACAAAGAGAACC
CCGAGGAAGAACCCTGCCTAACGCCTACGATAAGAGCCTGGACTGCTTC
CGGCGGCTGCTGCTGATTAGAAGCTGGTGTCCCGACCGGACAATCGCCCA
GGCCCGCAAGTACATCGTGGATAGCATGGGAGAGAAGTACGCCGAGGGC
GTGATCCTGGACCTGGAAAAGACCTGGGAGGAAAGCGACCCCAGAACCC
CCCTGATCTGCCTGCTGAGCATGGGCTCCGACCCCACCGACAGCATTATC
GCCCTGGGCAAGAGACTGAAGATTGAGACAAGATACGTGTCCATGGGCC
AGGGCCAGGAAGTGCACGCTAGAAAGCTGCTGCAGCAGACTATGGCCAA
TGGCGGCTGGGCCCTGCTGCAGAATTGTCACCTGGGGCTGGACTTCATGG
ACGAACTGATGGACATCATCATTGAGACAGAGCTGGTGCACGACGCCTTC
AGACTGTGGATGACCACCGAGGCCCATAAGCAGTTTCCCATTACCCTGCT
GCAGATGAGCATCAAGTTCGCCAACGACCCCCCTCAGGGACTGAGAGCC
GGCCTGAAGAGAACCTACTCCGGCGTGTCACAGGATCTGCTGGACGTGTC
CTCTGGCAGCCAGTGGAAGCCTATGCTGTACGCCGTGGCATTCCTGCACA
GCACCGTGCAGGAACGGCGGAAGTTTGGCGCCCTGGGATGGAACATCCC
CTACGAGTTTAACCAGGCCGACTTCAACGCCACTGTGCAGTTTATCCAGA
ACCATCTGGACGACATGGACGTGAAGAAAGGGGTGTCCTGGACAACCAT
CCGGTACATGATCGGAGAGATCCAGTACGGCGGCAGAGTGACCGACGAC
TACGACAAGAGGCTGCTGAATACCTTCGCCAAAGTGTGGTTCTCCGAGAA
CATGTTTGGCCCCGACTTCAGCTTTTACCAGGGCTATAACATCCCCAAGTG
CTCCACCGTGGATAACTACCTGCAGTACATCCAGAGCCTGCCCGCCTACG
ACAGCCCTGAGGTGTTCGGACTGCACCCCAACGCCGATATCACCTACCAG
AGCAAACTGGCCAAGGATGTGCTGGATACCATCCTGGGCATCCAGCCCAA
GGATACCAGTGGCGGAGGCGACGAAACCCGGGAAGCAGTGGTGGCTAGA
CTGGCCGACGACATGCTGGAAAAGCTGCCCCCCGACTACGTGCCCTTTGA
AGTGAAAGAACGCCTGCAGAAGATGGGCCCCTTCCAGCCTATGAACATCT
TCCTGAGGCAGGAAATCGACCGGATGCAGCGGGTGCTGTCTCTCGTGCGG
AGCACACTGACCGAGCTGAAACTGGCTATCGACGGCACCATCATCATGAG
CGAGAATCTGCGGGATGCACTGGACTGCATGTTCGACGCCAGAATCCCCG
CATGGTGGAAAAGGCCAGCTGGATCAGCTCTACCCTGGGCTTCTGGTTC
ACCGAACTGATCGAGAGAAACAGCCAGTTTACCAGCTGGGTGTTCAACG
GCAGACCTCACTGCTTCTGGATGACCGGCTTCTTCAATCCACAAGGCTTTC
TGACAGCAATGCGCCAGGAAATCACCAGAGCCAACAAGGGCTGGGCTCT
GGACAATATGGTGCTGTGTAACGAAGTGACTAAGTGGATGAAGGACGAC
ATCAGCGCCCCTCCCACCAGAGGGCGTGTACGTGTACGGCCTGTACCTGGA
AGGCGCCGGATGGGACAAGAGAAACATGAAGCTGATCGAGAGCAAGCCC
AAGGTGCTGTTCGAGCTGATGCCCGTGATCAGGATCTATGCCGAGAACAA
CACCCTGAGGGACCCCCGGTTCTACAGCTGCCCCATCTACAAGAAACCCG
TGCGCACCGACCTGAACTATATCGCCGCCGTGGACCTGAGGACAGCCCAG
ACACCTGAGCATTGGGTGCTGAGAGGCGTGGCACTGCTGTGCGACGTGAA
GTGA (SEQ ID NO: 18) |

Nucleic Acid Constructs, Vectors, and Engineered Polyribonucleotides

The present disclosure provides nucleic acid molecules, such as polynucleotides, which encode one or more polypeptides of interest. The term nucleic acid includes any compound and/or substance that comprise a polymer of nucleotides. Nucleotide polymers that contain greater than 50% of ribose bases or ribonucleotide analogues are referred to as polyribonucleotides. Nucleotide polymers may use altered nucleotide usage that encode a protein or functional fragment thereof, such as DNAI1 or DNAH5. The sequence of the engineered polynucleotides can be derived from, for example, DNA, RNA, mRNA transcripts, genomic DNA, mitochondrial DNA, mitochondrial RNA, or another suitable nucleic acid that comprises the genetic information of a gene of interest. The nucleic acid constructs, vectors, engineered polyribonucleotides, or compositions can be derived from nucleic acids carrying mutated genes and polymorphisms.

In addition to the four canonical ribonucleotides, namely, adenosine, guanosine, cytidine and uridine, several cellular RNAs also contain a number of structurally diverse ribonucleotides. About a hundred structurally different nucleotides or nucleotide analogues have been identified in transfer RNAs (tRNAs), ribosomal RNAs (rRNAs), messenger RNAs (mRNAs) and small nuclear RNAs (snRNAs). In tRNAs, some nucleotides can be important determinants of the specificity and efficiency of aminoacylation and codon recognition. Such structurally diverse ribonucleotides can be a modified ribonucleotide or a nucleotide analogue. In some cases, a polynucleotide of the disclosure is engineered to comprise a ribonucleotide analogue.

In some cases, a nucleic acid construct, a vector, or a polynucleotide is engineered to contain the four classical ribonucleotides and can be modified post-transcriptionally, after being administered to a subject. For instance, in some cases the disclosure provides a composition, vector, or a nucleic acid construct comprising a nucleic acid construct encoding dynein axonemal intermediate chain 1, wherein fewer than 30% of the nucleic acids encoding dynein axonemal intermediate chain 1 are nucleotide analogues. In other cases, fewer than 27.5%, fewer than 25%, fewer than 22.5%, fewer than 20%, fewer than 17.5%, fewer than 15%, fewer than 12.5%, fewer than 10%, fewer than 7.5%, fewer than 5%, or fewer than 2.5% of the nucleotides encoding dynein axonemal intermediate chain 1 are nucleotide analogues.

Exemplary nucleic acids that can form a polynucleotide of the disclosure include, but are not limited to, ribonucleic acids (RNAs), deoxyribonucleic acids (DNAs), or hybrids thereof. Exemplary modified nucleotides that can form at least a fraction of a polynucleotide of the disclosure include, but are not limited to, pseudouridine ($\Psi$) and 1-methylpseudouridine ($m^1\Psi$).

A chemical modification can be located on one or more nucleoside(s) or the backbone of the nucleic acid molecule. They can be located on both a nucleoside and a backbone linkage. A modification can be engineered into a polynucleotide in vitro. Modified ribonucleotides and nucleic acid analogues can also be introduced post-transcriptionally by covalent modification of the classical ribonucleotides.

A nucleic acid construct, a vector, or an engineered polyribonucleotide of the disclosure can comprise purine and pyrimidine analogues. In some cases, a polyribonucleotide of the disclosure comprises a modified pyrimidine, such as a modified uridine. In some cases a uridine analogue is selected from pseudouridine (W), 1-methylpseudouridine ($m^1\Psi$), 2-thiouridine ($s^2U$), 5-methyluridine ($m^5U$), 5-methoxyuridine ($mo^5U$), 4-thiouridine ($s^4U$), 5-bromouridine ($Br^5U$), 2'O-methyluridine (U2'm), 2'-amino-2'-deoxyuridine (U2'NH$_2$), 2'-azido-2'-deoxyuridine (U2'N$_3$), and 2'-fluoro-2'-deoxyuridine (U2'F).

In some instances, the nucleic acid construct(s), vector(s), engineered polyribonucleotide(s), or composition(s) encodes dynein axonemal intermediate chain 1 protein or a variant thereof at a level that is increased by a factor of at least about 1.5 as compared to levels within cells exposed to a composition comprising a nucleic acid construct that does not include the codons encoding dynein axonemal intermediate chain 1 protein or a variant thereof. In some cases, the factor is at least about 1.1, at least about 1.2, at least about 1.3, at least about 1.4, at least about 1.5, at least about 2, at least about 3, at least about 4, at least about 5, at least about 10, at least about 20, at least about 30, at least about 40, at least about 50, at least about 60, at least about 70, at least about 80, at least about 90, or at least about 100.

A polyribonucleotide can have the same or a mixture of different nucleotide analogues or modified nucleotides. The nucleotide analogues or modified nucleotides can have structural changes that are naturally or not naturally occurring in messenger RNA. A mixture of various analogues or modified nucleotides can be used. For example one or more analogues within a polynucleotide can have natural modifications, while another part has modifications that are not naturally found in mRNA. Additionally, some analogues or modified ribonucleotides can have a base modification, while other modified ribonucleotides have a sugar modification. In the same way, it is possible that all modifications are base modifications or all modifications are sugar modifications or any suitable mixture thereof.

A nucleotide analogue or modified nucleotide can be selected from the group comprising pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, 4-methoxy-2-thio-pseudouridine, 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, 4-methoxy-1-methyl-pseudoisocytidine, 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, 2-methoxy-adenine, inosine, 1-methylinosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

In some cases, at least about 5% of the nucleic acid construct(s), a vector(s), engineered polyribonucleotide(s), or compositions includes non-naturally occurring (e.g., modified, analogues, or engineered) uridine, adenosine, guanine, or cytosine, such as the nucleotides described herein. In some cases, 100% of the modified nucleotides in the composition are either 1-methylpseudouridine or pseudouridine. In some cases, at least about 10%, 15%, 20%, 25%, 30%, 35%, 40%, 45%, 50%, 55%, 60%, 65%, 70%, 75%, 80%, 85%, 90%, 95% of the nucleic acid construct(s), a vector(s), engineered polyribonucleotide(s), or compositions includes non-naturally occurring uracil, adenine, guanine, or cytosine. In some cases, at most about 99%, 95%, 90%, 85%, 80%, 75%, 70%, 65%, 60%, 55%, 50%, 45%, 40%, 35%, 30%, 25%, 20%, 15%, 10%, 5%, 1%, of the nucleic acid construct(s), a vector(s), engineered polyribonucleotide(s), or compositions includes non-naturally occurring uracil, adenine, guanine, or cytosine.

A nucleic acid construct(s), a vector(s), or an engineered polyribonucleotide(s) of the disclosure can comprise one or more promoter sequences and any associated regulatory sequences. A promoter sequence and/or an associated regulatory sequence can comprise any number of modified or unmodified nucleotides, and any number of nucleic acid analogues. Promoter sequences and/or any associated regulatory sequences can comprise, for example, at least 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 11 bases or base pairs, 12 bases or base pairs, 13 bases or base pairs, 14 bases or base pairs, 15 bases or base pairs, 16 bases or base pairs, 17 bases or base pairs, 18 bases or base pairs, 19 bases or base pairs, 20 bases or base pairs, 21 bases or base pairs, 22 bases or base pairs, 23 bases or base pairs, 24 bases or base pairs, 25 bases or base pairs, 26 bases or base pairs, 27 bases or base pairs, 28 bases or base pairs, 29 bases or base pairs, 30 bases or base pairs, 35 bases or base pairs, 40 bases or base pairs, 50 bases or base pairs, 75 bases or base pairs, 100 bases or base pairs, 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, at least 10000 bases or base pairs or more. A promoter sequence and/or an associated regulatory sequence can comprise any number of modified or unmodified nucleotides, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 75 bases or base pairs, 50 bases or base pairs, 40 bases or base pairs, 35 bases or base pairs, 30 bases or base pairs, 29 bases or base pairs, 28 bases or base pairs, 27 bases or base pairs, 26 bases or base pairs, 25 bases or base pairs, 24 bases or base pairs, 23 bases or base pairs, 22 bases or base pairs, 21 bases or base pairs, 20 bases or base pairs, 19 bases or base pairs, 18 bases or base pairs, 17 bases or base pairs, 16 bases or base pairs, 15 bases or base pairs, 14 bases or base pairs, 13 bases or base pairs, 12 bases or base pairs, 11 bases or base pairs, 10 bases or base pairs, 9 bases or base pairs, 8 bases or base pairs, 7 bases or base pairs, 6 bases or base pairs, 5 bases or base pairs, 4 bases or base pairs, 3 bases or base pairs or 2 bases or base pairs.

In some cases, less than all of the nucleotides in the promoter sequence or associated regulatory region are nucleotide analogues or modified nucleotides. For instance, in some cases, less than or equal to 99%, 95%, 90%, 85%, 80%, 75%, 70%, 65%, 60%, 55%, 50%, 45%, 40%, 35%, 30%, 25%, 20%, 15%, 10%, or 5% of the nucleotides in a promoter or associated regulatory region. In some cases, all of the nucleotides in a promoter or associated regulatory region are nucleic acid analogues or modified nucleotides.

A nucleic acid construct(s), a vector(s), an engineered polyribonucleotide(s), or compositions of the disclosure can comprise an engineered 5' cap structure, or a 5'-cap can be added to a polyribonucleotide intracellularly. The 5'cap structure of an mRNA can be involved in binding to the mRNA Cap Binding Protein (CBP), which is responsible for mRNA stability in the cell and translation competency through the association of CBP with poly(A) binding protein to form the mature pseudo-circular mRNA species. The 5'cap structure can also be involved in nuclear export, increases in mRNA stability, and in assisting the removal of 5' proximal introns during mRNA splicing.

A nucleic acid construct(s), a vector(s), or an engineered polyribonucleotide(s) can be 5"-end capped generating a 5"-GpppN-3"-triphosphate linkage between a terminal guanosine cap residue and the 5'-terminal transcribed sense nucleotide of the mRNA molecule. The cap-structure can comprise a modified or unmodified 7-methylguanosine linked to the first nucleotide via a 5"-5" triphosphate bridge. This 5'-guanylate cap can then be methylated to generate an N7-methyl-guanylate residue (Cap-0 structure). The ribose sugars of the terminal and/or anteterminal transcribed nucleotides of the 5'end of the mRNA may optionally also be 2"-O-methylated (Cap-1 structure). 5'-decapping through hydrolysis and cleavage of the guanylate cap structure may target a nucleic acid molecule, such as an mRNA molecule, for degradation.

In some cases, a cap can comprise further modifications, including the methylation of the 2' hydroxy-groups of the first 2 ribose sugars of the 5' end of the mRNA. For instance, an eukaryotic cap-1 has a methylated 2'-hydroxy group on the first ribose sugar, while a cap-2 has methylated 2'-hydroxy groups on the first two ribose sugars. The 5' cap can be chemically similar to the 3' end of an RNA molecule (the 5' carbon of the cap ribose is bonded, and the free 3'-hydroxyls on both 5'- and 3'-ends of the capped transcripts. Such double modification can provide significant resistance to 5' exonucleases. Non-limiting examples of 5' cap structures that can be used with an engineered polyribonucleotide include, but are not limited to, $m^7G(5')ppp(5')N$(Cap-0), $m^7G(5')ppp(5')N1mpNp$ (Cap-1), and $m^7G(5')\text{-}ppp(5')N1mpN2mp$ (Cap-2).

Modifications to the modified mRNA of the present disclosure may generate a non-hydrolyzable cap structure preventing decapping and thus increasing mRNA half-life while facilitating efficient translation. Because cap structure hydrolysis requires cleavage of 5'-ppp-5'triphosphate linkages, modified nucleotides may be used during the capping reaction. For example, a Vaccinia Capping Enzyme from New England Biolabs (Ipswich, Mass.) may be used with guanosine α-thiophosphate nucleotides according to the manufacturer's instructions to create a phosphorothioate linkage in the 5'-ppp-5' cap. Additional modified guanosine nucleotides may be used such as α-methyl-phosphonate and seleno-phosphate nucleotides. Additional modifications include, but are not limited to, 2'-O-methylation of the ribose sugars of 5'-terminal and/or 5'-anteterminal nucleotides of the mRNA on the 2'-hydroxyl group of the sugar ring. Multiple distinct 5'-cap structures can be used to generate the 5'-cap of a polyribonucleotide.

The modified mRNA may be capped post-transcriptionally. According to the present disclosure, 5' terminal caps may include endogenous caps or cap analogues. According to the present disclosure, a 5' terminal cap may comprise a guanine analogue. Useful guanine analogues include, but are not limited to, inosine, N1-methyl-guanosine, 2'fluoroguanosine, 7-deaza-guanosine, 8-oxo-guanosine, 2-amino-guanosine, LNA-guanosine, and 2-azido-guanosine.

Further, a nucleic acid construct(s), a vector(s), or an engineered polyribonucleotide(s) can contain one or more internal ribosome entry site(s) (IRES). IRES sequences can initiate protein synthesis in absence of the 5' cap structure. An IRES sequence can also be the sole ribosome binding site, or it can serve as one of multiple ribosome binding sites of an mRNA. Engineered polyribonucleotides containing more than one functional ribosome binding site can encode several peptides or polypeptides that are translated by the ribosomes ("polycistronic or multicistronic polynucleotides"). An engineered polynucleotide described here can comprise at least 1 IRES sequence, two IRES sequences, three IRES sequences, four IRES sequences, five IRES sequences, six IRES sequences, seven IRES sequences, eight IRES sequences, nine IRES sequences, ten IRES sequences, or another suitable number are present in an engineered polyribonucleotide. Examples of IRES sequences that can be used according to the present disclosure include without limitation, those from tobacco etch virus (TEV), picornaviruses (e.g., FMDV), pest viruses (CFFV), polio viruses (PV), encephalomyocarditis viruses (EMCV), foot-and-mouth disease viruses (FMDV), hepatitis C viruses (HCV), classical swine fever viruses (CSFV), murine leukemia virus (MLV), simian immune deficiency viruses (SIV) or cricket paralysis viruses (CrPV). An IRES sequence can be derived, for example, from commercially available vectors such as the IRES sequences available from Clontech™, GeneCopoeia™, or Sigma-Aldrich™. IRES sequences can be, for example, at least 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, or 10000 bases or base pairs. IRES sequences can at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, 100 bases or base pairs, 50 bases or base pairs, or 10 bases or base pairs.

A nucleic acid construct(s), a vector(s), or an engineered polyribonucleotide(s) of the disclosure can comprise one or more untranslated regions. An untranslated region can comprise any number of modified or unmodified nucleotides. Untranslated regions (UTRs) of a gene are transcribed but not translated into a polypeptide. In some cases, an untranslated sequence can increase the stability of the nucleic acid molecule and the efficiency of translation. The regulatory features of a UTR can be incorporated into the modified mRNA molecules of the present disclosure, for instance, to increase the stability of the molecule. The specific features can also be incorporated to ensure controlled down-regulation of the transcript in case they are misdirected to undesired organs sites. Some 5' UTRs play roles in translation initiation. A 5' UTR can comprise a Kozak sequence which is involved in the process by which the ribosome initiates translation of many genes. Kozak sequences can have the consensus GCC(R)CCAUGG (SEQ ID NO: 19), where R is a purine (adenine or guanine) that is located three bases upstream of the start codon (AUG). 5' UTRs may form secondary structures which are involved in binding of translation elongation factor. In some cases, one can increase the stability and protein production of the engineered polynucleotide molecules of the disclosure, by engineering the features typically found in abundantly expressed genes of specific target organs. For example, introduction of 5'UTR of liver-expressed mRNA, such as albumin, serum amyloid A, Apolipoprotein A/B/E, transferrin, alpha fetoprotein, erythropoietin, or Factor VIII, can be used to increase expression of an engineered polynucleotide in a liver. Likewise, use of 5' UTR from muscle proteins (MyoD, Myosin, Myoglobin, Myogenin, Herculin), for endothelial cells (Tie-1, CD36), for myeloid cells (C/EBP, AML1, G-CSF, GM-CSF, CD11b, MSR, Fr-1, i-NOS), for leukocytes (CD45, CD18), for adipose tissue (CD36, GLUT4, ACRP30, adiponectin) and for lung epithelial cells (SP-A/B/C/D) can be used to increase expression of an engineered polynucleotide in a desired cell or tissue.

Other non-UTR sequences can be incorporated into the 5' (or 3' UTR) UTRs of the polyribonucleotides of the present disclosure. The 5' and/or 3' UTRs can provide stability and/or translation efficiency of polyribonucleotides. For example, introns or portions of intron sequences can be incorporated into the flanking regions of an engineered polyribonucleotide. Incorporation of intronic sequences can also increase the rate of translation of the polyribonucleotide.

3' UTRs may have stretches of Adenosines and Uridines embedded therein. These AU rich signatures are particularly prevalent in genes with high rates of turnover. Based on their sequence features and functional properties, the AU rich elements (AREs) can be separated into classes: Class I AREs contain several dispersed copies of an AUUUA motif within U-rich regions. C-Myc and MyoD contain class I AREs. Class II AREs possess two or more overlapping UUAUUUA (U/A)(U/A) nonamers. Molecules containing this type of AREs include GM-CSF and TNF-α. Class III ARES are less well defined. These U rich regions do not contain an AUUUA motif c-Jun and Myogenin are two well-studied examples of this class. Proteins binding to the AREs may destabilize the messenger, whereas members of the ELAV family, such as HuR, may increase the stability of mRNA. HuR may bind to AREs of all the three classes. Engineering the HuR specific binding sites into the 3' UTR of nucleic acid molecules can lead to HuR binding and thus, stabilization of the message in vivo.

Engineering of 3' UTR AU rich elements (AREs) can be used to modulate the stability of an engineered polyribonucleotide. One or more copies of an ARE can be engineered into a polyribonucleotide to modulate the stability of a polyribonucleotide. AREs can be identified, removed or mutated to increase the intracellular stability and thus increase translation and production of the resultant protein. Transfection experiments can be conducted in relevant cell lines, using engineered polyribonucleotides and protein production can be assayed at various time points post-transfection. For example, cells can be transfected with different ARE-engineering molecules and by using an ELISA kit to the relevant protein and assaying protein produced at 6 hours, 12 hours, 24 hours, 48 hours, and 7 days post-transfection.

An untranslated region can comprise any number of nucleotides. An untranslated region can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. An untranslated region can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length.

An engineered polyribonucleotide of the disclosure can comprise one or more introns. An intron can comprise any number of modified or unmodified nucleotides. An intron can comprise, for example, at least 1 base or base pair, 50 bases or base pairs, 100 bases or base pairs, 150 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, or 5000 bases or base pairs. In some cases, an intron can comprise, for example, at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs.

In some cases, a percentage of the nucleotides in an intron are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in an intron are modified. In some cases, all of the nucleotides in an intron are modified.

An engineered polyribonucleotide of the disclosure can comprise a polyA sequence. A polyA sequence (e.g., polyA tail) can comprise any number of nucleotides. A polyA sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. In some examples, a polyA sequence is at least about 100, 110, 120, 130, 140, 150, 160, 170, 180, 190, or 200 nucleotides in length. A polyA sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or 10000 bases or base pairs in length. A polyA sequence can comprise a length of at most 100 bases or base pairs, 90 bases or base pairs, 80 bases or base pairs, 70 bases or base pairs, 60 bases or base pairs, 50 bases or base pairs, 40 bases or base pairs, 30 bases or base pairs, 20 bases or base pairs, 10 bases or base pairs, or 5 bases or base pairs.

In some cases, a percentage of the nucleotides in a poly-A sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a poly-A sequence are modified. In some cases, all of the nucleotides in a poly-A are modified.

A linker sequence can comprise any number of nucleotides. A linker can be attached to the modified nucleobase at an N-3 or C-5 position. The linker attached to the nucleobase can be diethylene glycol, dipropylene glycol, triethylene glycol, tripropylene glycol, tetraethylene glycol, tetraethylene glycol, divalent alkyl, alkenyl, alkynyl moiety, ester, amide, or an ether moiety. A linker sequence can comprise a length of about 1 to about 10 bases or base pairs, about 10 to about 20 bases or base pairs, about 20 to about 50 bases or base pairs, about 50 to about 100 bases or base pairs, about 100 to about 500 bases or base pairs, about 500 to about 1000 bases or base pairs, about 1000 to about 2000 bases or base pairs, about 2000 to about 3000 bases or base pairs, about 3000 to about 4000 bases or base pairs, about 4000 to about 5000 bases or base pairs, about 5000 to about 6000 bases or base pairs, about 6000 to about 7000 bases or base pairs, about 7000 to about 8000 bases or base pairs, about 8000 to about 9000 bases or base pairs, or about 9000 to about 10000 bases or base pairs in length. A linker sequence can comprise a length of for example, at least 1 base or base pair, 2 bases or base pairs, 3 bases or base pairs, 4 bases or base pairs, 5 bases or base pairs, 6 bases or base pairs, 7 bases or base pairs, 8 bases or base pairs, 9 bases or base pairs, 10 bases or base pairs, 20 bases or base pairs, 30 bases or base pairs, 40 bases or base pairs, 50 bases or base pairs, 60 bases or base pairs, 70 bases or base pairs, 80 bases or base pairs, 90 bases or base pairs, 100 bases or base pairs, 200 bases or base pairs, 300 bases or base pairs, 400 bases or base pairs, 500 bases or base pairs, 600 bases or base pairs, 700 bases or base pairs, 800 bases or base pairs, 900 bases or base pairs, 1000 bases or base pairs, 2000 bases or base pairs, 3000 bases or base pairs, 4000 bases or base pairs, 5000 bases or base pairs, 6000 bases or base pairs, 7000 bases or base pairs, 8000 bases or base pairs, 9000 bases or base pairs, or at least 10000 bases or base pairs in length. A linker at most 10000 bases or base pairs, 5000 bases or base pairs, 4000 bases or base pairs, 3000 bases or base pairs, 2000 bases or base pairs, 1000 bases or base pairs, 900 bases or base pairs, 800 bases or base pairs, 700 bases or base pairs, 600 bases or base pairs, 500 bases or base pairs, 400 bases or base pairs, 300 bases or base pairs, 200 bases or base pairs, or 100 bases or base pairs in length.

In some cases, a percentage of the nucleotides in a linker sequence are modified. For instance, in some cases, fewer than 99%, 95%, 90%, 85%, 80%, 75%, 70%, 65%, 60%, 55%, 50%, 45%, 40%, 35%, 30%, 25%, 20%, 15%, 10%, 5% or 1% of the nucleotides in a linker sequence are modified. In some cases, all of the nucleotides in a linker sequence are modified.

In some cases, a nucleic acid construct(s), a vector(s), or an engineered polyribonucleotide(s) can include at least one stop codon before the 3'untranslated region (UTR). In some cases, a nucleic acid construct(s), a vector(s), or an engineered polyribonucleotide(s) includes multiple stop codons. The stop codon can be selected from TGA, TAA and TAG. The stop codon may be modified or unmodified. In some cases, the nucleic acid construct(s), vector(s), or engineered polyribonucleotide(s) includes the stop codon TGA and one additional stop codon. In some cases, the nucleic acid construct(s), vector(s), or engineered polyribonucleotide(s) includes the addition of the TAA stop codon.

Encoded Polypeptides

In some cases, the disclosure provides a method for treating a subject having or at risk of having primary ciliary dyskinesia, the method comprising administrating to the subject a composition that comprises a nucleic acid construct that encodes dynein axonemal intermediate chain 1 protein (DNAI1), armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10), or a variant of any of the aforementioned, which nucleic acid construct includes codons that provide for heterologous or enhanced expression of said protein(s) or a variant thereof within cells of the subject, thereby treating the subject having or at risk of having primary ciliary dyskinesia.

The encoded polypeptides are polymer chains comprised of amino acid residue monomers which are joined together through amide bonds (peptide bonds). The amino acids may be of the L-optical isomer, the D-optical isomer or a combination thereof. A polypeptide can be a chain of at least three amino acids, peptide-mimetics, a protein, a recombinant protein, an antibody (monoclonal or polyclonal), an antigen, an epitope, an enzyme, a receptor, a vitamin, or a structure analogue or combinations thereof. A polyribonucleotide that is translated within a subject's body can generate an ample supply of specific peptides or proteins within a cell, a tissue, or across many cells and tissues of a subject. In some cases, a polyribonucleotide can be translated in vivo within the cytosol of a specific target cell(s) type or target tissue. In some cases, a polyribonucleotide can be translated in vivo to provide a protein whose gene has been associated with primary ciliary dyskinesia, a functional fragment thereof, or a protein that is at least 70% homologous to a human DNAI1 or a human DNAH5 protein. In some cases, a polyribonucleotide can be translated in vivo in various non-target cell types or target tissue(s). Non-limiting examples of cells that be target or non-target cells include: a) skin cells, e.g.: keratinocytes, melanocytes, urothelial cells; b) neural cells, e.g.: neurons, Schwann cells, oligodentrocytes, astrocytes; c) liver cells, e.g.: hepatocytes; d) intestinal cells, e.g.: goblet cell, enterocytes; e) blood cells; e.g.: lymphoid or myeloid cells; and f) germ cells; e.g.: sperm and eggs. Non-limiting examples of tissues include connective tissue, muscle tissue, nervous tissue, or epithelial tissue. In some cases, a target cell or a target tissue is a cancerous cell, tissue, or organ.

A polynucleotide sequence can be derived from one or more species. For example, a polynucleotide sequence can be derived from a human (*Homo sapiens*), a mouse (e.g., *Mus musculus*), a rat (e.g., *Rattus norvegicus* or *Rattus rattus*), a microorganism (e.g., *Chlamydomonas* genus), or any other suitable creature. A polynucleotide sequence can be a chimeric combination of the sequence of one or more species.

In some cases, the endogenous translational machinery can add a post-translational modification to the encoded peptide. A post-translational modification can involve the addition of hydrophobic groups that can target the polypeptide for membrane localization, the addition of cofactors for increased enzymatic activity, or the addition of smaller chemical groups. The encoded polypeptide can also be post-translationally modified to receive the addition of other peptides or protein moieties. For instance, ubiquitination can lead to the covalent linkage of ubiquitin to the encoded polypeptide, SUMOylation can lead to the covalent linkage of SUMO (Small Ubiquitin-related MOdifier) to the encoded polypeptide, ISGylation can lead to the covalent linkage of ISG15 (Interferon-Stimulate Gene 15).

In some cases, the encoded polypeptide can be post-translationally modified to undergo other types of structural changes. For instance, the encoded polypeptide can be proteolytically cleaved, and one or more proteolytic fragments can modulate the activity of an intracellular pathway. The encoded polypeptide can be folded intracellularly. In some cases, the encoded polypeptide is folded in the presence of co-factors and molecular chaperones. A folded polypeptide can have a secondary structure and a tertiary structure. A folded polypeptide can associate with other folded peptides to form a quaternary structure. A folded-peptide can form a functional multi-subunit complex, such as an antibody molecule, which has a tetrameric quaternary structure. Various polypeptides that form classes or isotypes of antibodies can be expressed from a polyribonucleotide.

The encoded polypeptide can be post-translationally modified to change the chemical nature of the encoded amino acids. For instance, the encoded polypeptide can undergo post-translational citrullination or deimination, the conversion of arginine to citrulline. The encoded polypeptide can undergo post-translation deamidation; the conversion of glutamine to glutamic acid or asparagine to aspartic acid. The encoded polypeptide can undergo elimination, the conversion of an alkene by beta-elimination of phosphothreonine and phosphoserine, or dehydration of threonine and serine, as well as by decarboxylation of cysteine. The encoded peptide can also undergo carbamylation, the conversion of lysine to homocitrulline. An encoded peptide can also undergo racemization, for example, racemization of proline by prolyl isomerase or racemization of serine by protein-serine epimerase. In some cases, an encoded peptide can undergo serine, threonine, and tyrosine phosphorylation.

The activity of a plurality of biomolecules can be modulated by a molecule encoded by a polyribonucleotide. Non-limiting examples of molecules whose activities can be modulated by an encoded polynucleotide include: amino acids, peptides, peptide-mimetics, proteins, recombinant proteins antibodies (monoclonal or polyclonal), antibody fragments, antigens, epitopes, carbohydrates, lipids, fatty acids, enzymes, natural products, nucleic acids (including DNA, RNA, nucleosides, nucleotides, structure analogues or combinations thereof), nutrients, receptors, and vitamins.

Non-limiting examples of nucleotide sequences that can be a part of a polynucleotide of the disclosure are disclosed in TABLE 3.

TABLE 3

| Name | Sequence |
|---|---|
| dynein axonemal intermediate chain 1 (DNAI1) | SEQ ID NOs: 14-16 |
| dynein axonemal heavy chain 5 (DNAH5) | SEQ ID NOs: 17-18 |

A polypeptide sequence can be engineered to have a desired altered codon usage, such as the altered codon usage of SEQ ID NOs 15-16 or the altered codon usage of SEQ ID NOs 17-18. Computer software can be used, for example, to generate the codon usage of SEQ ID NO 14. A polypeptide sequence can share a % homology to an amino acid sequence of an endogenous polypeptide. A polypeptide sequence can share at most 10% homology, at most 20% homology, at most 30% homology, at most 40% homology, at most 50% homology, at most 60% homology, at most 70% homology, at most 80% homology, at most 90% homology, or at most 99% homology with an amino acid sequence of an endogenous polypeptide. Various methods and software programs can be used to determine the homology between two or more peptides, such as NCBI BLAST, Clustal W, MAFFT, Clustal Omega, AlignMe, Praline, or another suitable method or algorithm.

Immunogenicity

Many pharmaceutical agents, including compositions comprising molecules of various sizes (polynucleotides, proteins, or enzymes) can trigger an immune response when administered to a subject. In many cases, the immune system recognizes the composition as a foreign body and neutralizes its pharmaceutical action. A polyribonucleotide and a composition of the present disclosure can have low immunogenicity or be non-immunogenic, thereby triggering a small response by the immune system, or not triggering any immune response at all.

The immunogenicity can also be determined by measurement of, for example, the TNF-α and IL-8 levels and the binding capacity to TLR-3, TLR-7, TLR-8 and helicase RIG-1. In order thereby to establish whether a polyribonucleotide has a desired low immunogenicity, the quantity of one or more of the factors can be measured after administration of the polyribonucleotide to a subject. The immunogenicity of a polypeptide can be determined in relation to an increase in the number of white blood cells upon administration of the polypeptide to the subject. In some cases, upon administration of the composition to the subject, the subject exhibits an increase in the number of white blood cells that is less than 90%, less than 80%, less than 70%, less than 60%, less than 50%, less than 40%, less than 30%, less than 20%, or less than 10%. A polyribonucleotide of the disclosure can trigger minimum or insignificant inflammatory or immunological reactions.

For the determination of the immunogenicity of a polyribonucleotide, various methods can be used. A very suitable method is the determination of inflammatory markers in cells or a simple white cell blood count, as a reaction to the administration of the polyribonucleotide. Such a method is described in the examples. Cytokines which are associated with inflammation, such as, for example TNF-α, IFN-α, IFN-β, IP-10, IL-8, IL-6, and/or IL-12, can be measured. The expression of dendritic cell activation markers can also be used for the estimation of immunogenicity. A further indication of an immunological reaction can be the detection of binding to the Toll-like receptors TLR-3, TLR-7 and TLR-8 and to helicase RIG-1.

The immunogenicity of a polyribonucleotide can be determined as an overall increase in the level of inflammatory marker or white blood cell count as compared to a level prior to the administration of the polyribonucleotide. For instance, an engineered polyribonucleotide that is unmodified or modified can be administered to cells, or to a subject, and the secretion of inflammatory markers in a defined time interval as a reaction to the administration of the polyribonucleotide can be measured.

Compositions

In some cases, the disclosure provides a composition comprising a nucleic acid construct encoding dynein axonemal intermediate chain 1, wherein the nucleic acid construct comprises a complementary deoxyribonucleic acid encoding dynein axonemal intermediate chain 1, which composition is formulated for administration to a subject. In some cases, the disclosure provides a composition comprising a nucleic acid construct encoding dynein axonemal intermediate chain 1, which nucleic acid construct includes codons that provide for heterologous or enhanced expression of the dynein axonemal intermediate chain 1 protein or a variant thereof within cells of a subject having or at risk of having primary ciliary dyskinesia. In some cases, the disclosure provides a composition comprising a nucleic acid construct encoding dynein axonemal intermediate chain 1, wherein fewer than 30% of the nucleic acids encoding dynein axonemal intermediate chain 1 are nucleic acid analogues, such as pseudouridine or 1-methyl pseudouridine. In some cases, the coding sequence of these constructs is engineered to have an altered nucleotide usage in the protein coding regions to increase its stability.

In some cases, the codons of the construct are at least 70% homologous to a mammalian or to a human dynein axonemal intermediate chain 1 protein. The construct may also comprise a 3' or 5' noncoding region flanking the codon sequence which encodes a protein of interest, such as dynein axonemal intermediate chain 1, wherein the noncoding region enhances the expression of the protein within cells the subject. The 3' noncoding region flanking the codon can comprise a 3'-cap independent translation enhancer ($3^1$-CITEs) or a 3'-stem loop region derived from the nucleotide sequence of a histone protein or a 3'-triple helical structure derived from the nucleotide sequence of metastasis-associated lung adenocarcinoma transcript 1 (MALAT1). The 3' noncoding region flanking the codon can comprise a poly adenosine tail, wherein the number of adenosines in the poly adenosine tail improves the translation efficiency or the half-life of the protein of interest, such as dynein axonemal intermediate chain 1 protein. In some cases, the length of the poly adenosine tail is at most 200 adenosines. In some cases, a percentage of the poly adenosine tail comprises nucleic acid analogues. Fewer than 50%, 40%, 30%, 20%, 10%, or 5% of the nucleic acids in the poly adenosine tail can be nucleic acid analogues.

When the composition comprises a percentage of nucleotide analogues the nucleotide analogues can be selected from the group consisting of pseudouridine, 1-methylpseudouridine, 2-thiouridine, 5-methyluridine, 5-methoxyuridine, 5-methylcytidine, 2"-amino-2"-deoxycytidine, 2'-fluoro-2'-deoxycytidine, and. In some cases, the nucleic acid analogue is pseudouridine or 1-methylpseudouridine. In some cases, the nucleic acid analogue is 5-methoxyuridine.

In some cases, the composition comprises a nucleic acid encoding dynein axonemal intermediate chain 1 and/or nucleic acid analogues. Optionally, the composition can further comprise at least one additional nucleic acid construct. The at least one additional nucleic acid construct may encode a protein selected from the group consisting of: armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10).

The compositions may comprise engineered polyribonucleotides, vectors, or nucleic acid constructs. "Naked" polynucleotide compositions can be successfully administered to a subject, and uptaken by a subject's cell, without the aid of carriers, stabilizers, diluents, dispersing agents, suspending agents, thickening agents, and/or excipients (Wolff et al. 1990, Science, 247, 1465-1468). However, in many instances, encapsulation of polynucleotides with formulations that can increase the endocytotic uptake can increase the effectiveness of a composition of the disclosure. To overcome this challenge, in some cases, the composition comprises a nucleic acid construct, a vector, or an isolated nucleic acid encoding dynein axonemal intermediate chain 1, wherein the nucleic acid construct comprises a complementary deoxyribonucleic acid encoding dynein axonemal intermediate chain 1, which composition is formulated for administration to a subject.

Another technical challenge underlying the delivery of polyribonucleotides to multicellular organisms is to identify a composition that provides a high efficiency delivery of polyribonucleotides that are translated within a cell or a tissue of a subject. It has been recognized that administration of naked nucleic acids may be highly inefficient and may not provide a suitable approach for administration of a polynucleotide to a multicellular organism.

To solve this challenge, a composition comprising an engineered polyribonucleotide can be encapsulated or formulated with a pharmaceutical carrier. The formulation may be, but is not limited to, nanoparticles, poly(lactic-co-glycolic acid) (PLGA) microspheres, lipidoids, lipoplex, liposome, polymers, carbohydrates (including simple sugars), cationic lipids, fibrin gel, fibrin hydrogel, fibrin glue, fibrin sealant, fibrinogen, thrombin, rapidly eliminated lipid nanoparticles (reLNPs) and combinations thereof. A composition comprising an engineered polyribonucleotide disclosed herein can comprise from about 1% to about 99% weight by volume of a carrier system. The amount of carrier present in a carrier system is based upon several different factors or choices made by the formulator, for example, the final concentration of the polyribonucleotide and the amount of solubilizing agent. Various carriers have been shown useful in delivery of different classes of therapeutic agents. Among these carriers, biodegradable nanoparticles formulated from biocompatible polymers poly(D,L-lactide-co-glycolide) (PLGA) and polylactide (PLA) have shown the potential for sustained intracellular delivery of different therapeutic agents.

The loading weight percent of the engineered polynucleotide in a composition may be at least 0.05%, 0.1%, 0.2%, 0.3%, 0.4%, 0.5%, 1%, 2%, 4%, 5%, 6%, 7%, 8%, 9%, or 10%. The encapsulation efficiency of the modified mRNA in the PLGA microsphere may be at least 50%, at least 70%, at least 90%, at least 95%, at least 96%, at least 97%, at least 98%, or at least 99%.

The present disclosure describes nanoparticles, oligomers, polymers or lipidoids comprising oligo(alkylene amines) containing alternating, non-identical alkylene amine units which are useful for delivering a polynucleotide, in some cases an engineered polyribonucleotides, into a cell or into a tissue. A composition disclosed herein can be stable for at least about 1 minute, 5 minutes, 10 minutes, 30 minutes, 1 hour, 2 hours, 3 hours, 4 hours, 5 hours, 6 hours, 12 hours, 1 day, 2 days, 3 days, 4 days, 5 days, 6 days, 7 days, 8 days, 9 days, 10 days, 2 weeks, 4 weeks, 6 weeks, 8 weeks, 10 weeks, 12 weeks, 3 months, 4 months, 5 months, 6 months, 7 months, 8 months, 9 months, 10 months, 11 months, or one year. A formulation disclosed herein can be stable, for example, at a temperature of at least about 0° C., 5° C., 10° C., 15° C., 20° C., 25° C., 30° C., 35° C., 40° C., 45° C., 50° C., 60° C., 70° C., or 80° C. A composition of the disclosure can have a desired density. The density of a composition can improve a property of the composition, such as the rheology of the composition.

Nanoparticles

The present disclosure also provides nanoparticle based formulations of nucleic acid constructs, engineered polyribonucleotides, or vectors that are able to translocate following administration to a subject. In some instances, the administration is pulmonary and the engineered polyribonucleotides can move intact either actively or passively from the site of administration to the systemic blood supply and subsequently to be deposited in different cells or tissues, such as, e.g., the breast. This translocation of the nanoparticle comprising an engineered polyribonucleotide encoding a therapeutic protein, such as, e.g., dynein axonemal intermediate chain 1 (DNAI1), armadillo repeat containing 4 (ARMC4), chromosome 21 open reading frame 59 (C21orf59), coiled-coil domain containing 103 (CCDC103), coiled-coil domain containing 114 (CCDC114), coiled-coil domain containing 39 (CCDC39), coiled-coil domain containing 40 (CCDC40), coiled-coil domain containing 65 (CCDC65), cyclin 0 (CCNO), dynein (axonemal) assembly factor 1 (DNAAF1), dynein (axonemal) assembly factor 2 (DNAAF2), dynein (axonemal) assembly factor 3 (DNAAF3), dynein (axonemal) assembly factor 5 (DNAAF5), dynein axonemal heavy chain 11 (DNAH11), dynein axonemal heavy chain 5 (DNAH5), dynein axonemal heavy chain 6 (DNAH6),dynein axonemal heavy chain 8 (DNAH8), dynein axonemal intermediate chain 2 (DNAI2), dynein axonemal light chain 1 (DNAL1), dynein regulatory complex subunit 1 (DRC1), dyslexia susceptibility 1 candidate 1 (DYX1C1), growth arrest specific 8 (GASB), axonemal central pair apparatus protein (HYDIN), leucine rich repeat containing 6 (LRRC6), NME/NM23 family member 8 (NME8), oral-facial-digital syndrome 1 (OFD1), retinitis pigmentosa GTPase regulator (RPGR), radial spoke head 1 homolog (*Chlamydomonas*) (RSPH1), radial spoke head 4 homolog A (*Chlamydomonas*) (RSPH4A), radial spoke head 9 homolog (*Chlamydomonas*) (RSPH9), sperm associated antigen 1(SPAG1), and zinc finger MYND-type containing 10 (ZMYND10) or a functional fragment thereof, constitutes non-invasive systemic delivery of an active pharmaceutical ingredient beyond the lung to result in the production of a functional protein to systemically accessible non-lung cells or tissues.

A nanoparticle can be a particle of particle size from about 10 nanometers (nm) to 5000 nm, 10 nm to 1000 nm, or 60 nm to 500 nm, or 70 nm to 300 nm. In some examples, a nanoparticle has a particle size from about 60 nm to 225 nm. The nanoparticle can include an encapsulating agent (e.g., coating) that encapsulates one or more polyribonucleotides, which may be engineered polyribonucleotides. The nanoparticle can include engineered and/or naturally occurring polyribonucleotides. The encapsulating agent can be a polymeric material, such as PEI or PEG.

A lipidoid or lipid nanoparticle which may be used as a delivery agent may include a lipid which may be selected from the group consisting of C12-200, MD1, 98N12-5, DLin-DMA, DLin-K-DMA, DLin-KC2-DMA, DLin-MC3-DMA, PLGA, PEG, PEG-DMG, PEGylated lipids and analogues thereof. A suitable nanoparticle can comprise one or more lipids in various ratios. For example, a composition of the disclosure can comprise a 40:30:25:5 ratio of C12-200:DOPE:Cholesterol:DMG-PEG2000 or a 40:20:35:5 ratio of HGT5001:DOPE:Cholesterol:DMG-PEG2000. A nanoparticle can include at least 1, 2, 3, 4, 5, 6, 7, 8, 9, 10 lipids or another suitable number of lipids. A nanoparticle can be formed of any suitable ratio of lipids selected from the group consisting of C12-200, MD1, 98N12-5, DLin-DMA, DLin-K-DMA, DLin-KC2-DMA, DLin-MC3-DMA, PLGA, PEG, PEG-DMG.

The mean size of the nanoparticle formulation may comprise the modified mRNA between 60 nanometers (nm) and 225 nm. The polydispersity index PDI of the nanoparticle formulation comprising the modified mRNA can be between 0.03 and 0.15. The zeta potential of the nanoparticle formulation may be from −10 to +10 at a pH of 7.4. The formulations of modified mRNA may comprise a fusogenic lipid, cholesterol and a PEG lipid. The formulation may have a molar ratio 50:10:38.5:1.5-3.0 (cationic lipid:fusogenic lipid: cholesterol: polyethylene glycol (PEG) lipid). The PEG lipid may be selected from, but is not limited to PEG-c-DOMG, PEG-DMG. The fusogenic lipid may be DSPC. A lipid nanoparticle of the present disclosure can be formulated in a sealant such as, but not limited to, a fibrin sealant.

Oligo(Alkylene Amine Groups)

It has also been recognized that although encapsulation of polynucleotides with some formulations can increase the endocytotic uptake of a composition, the polynucleotide that is taken up by a cell may not be effectively translated within the cell. Some formulations may be effectively used for plasmid DNA and/or siRNA delivery, while not practical for use in the delivery of polyribonucleotides. The present disclosure provides formulations that can be employed for effective delivery and translation of polyribonucleotide compositions to a subject.

A composition of the disclosure can be designed to provide a polyribonucleotide that is effectively translated within a cell. A composition of the disclosure can comprise an arrangement of alkylene amine units of alternating length in groups of three or more units and containing an ethyleneamine unit in compositions for transfecting a cell with any polynucleotide, such as an engineered polyribonucleotide. A composition of the disclosure can provide a more efficacious delivery of a polyribonucleotide to a cell than analogous arrangements of alkylene amine units of non-alternating length.

Oligomers, polymers or lipidoids can be provided which share a common structural entity which is illustrated in formula (I):

(I)

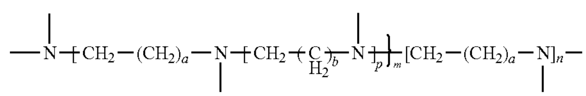

A composition of the disclosure can comprise an oligo (alkylene amine) that is selected from:

a) an oligomer or polymer comprising a plurality of groups of formula (II) as a side chain and/or as a terminal group:

(II)

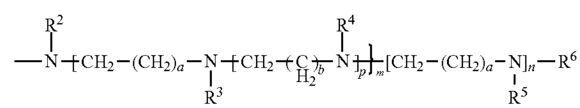

wherein the variables a, b, p, m, n, and $R^2$ to $R^6$ are defined as follows, independently for each group of formula (II) in a plurality of such groups:

a is 1 and b is an integer of 2 to 4; or a is an integer of 2 to 4 and b is 1, p is 1 or 2, m is 1 or 2; n is 0 or 1 and m+n is 2; and $R^2$ to $R^5$ are, independently of each other, selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; and a poly(ethylene glycol) chain;

$R^6$ is selected from hydrogen; a group —$CH_2$—CH(OH)—$R^7$, —CH($R^7$)—$CH_2$—OH, —$CH_2$—$CH_2$—(C═O)—O—$R^7$, —$CH_2$—$CH_2$—(C═O)—NH—$R^7$, or —$CH_2$—$R^7$ wherein $R^7$ is selected from C3-C18 alkyl or C3-C18 alkenyl having one C—C double bond; a protecting group for an amino group; —C(NH)—NH; a poly(ethylene glycol) chain; and a receptor ligand, and wherein one or more of the nitrogen atoms indicated in formula (II) may be protonated to provide a cationic group of formula (II).

b) an oligomer or polymer comprising a plurality of groups of formula (III) as repeating units:

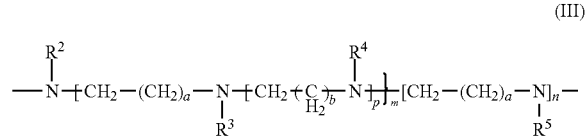

(III)

wherein the variables a, b, p, m, n, and $R^2$ to $R^5$ are defined as follows, independently for each group of formula (III) in a plurality of such groups:
a is 1 and b is an integer of 2 to 4; or a is an integer of 2 to 4 and b is 1,
p is 1 or 2,
m is 1 or 2; n is 0 or 1 and m+n is 2; and
$R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$, —$CH_2$—$R^7$ or —$CH_2$— wherein $R^7$ is selected from C3-C18 alkyl or C3-C18 alkenyl having one C=C double bond; a protecting group for an amino group; and a poly(ethylene glycol) chain;
and wherein one or more of the nitrogen atoms indicated in formula (III) may be protonated to provide a cationic group of formula (III).

c) a lipidoid having the structure of formula (IV):

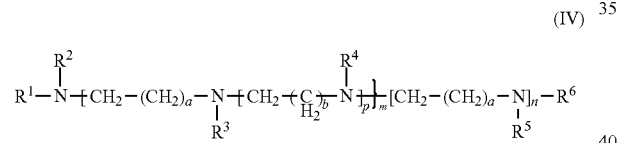

(IV)

wherein the variables a, b, p, m, n, and $R^2$ to $R^6$ are defined as follows:
a is 1 and b is an integer of 2 to 4; or a is an integer of 2 to 4 and b is 1,
p is 1 or 2,
m is 1 or 2; n is 0 or 1 and m+n is 2; and
$R^2$ to $R^6$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$, or —$CH_2$—$R^7$ wherein $R^7$ is selected from C3-C18 alkyl or C3-C18 alkenyl having one C=C double bond; a protecting group for an amino group; and a poly(ethylene glycol) chain; and a receptor ligand; provided that at least two residues among $R^1$ to $R^6$ are a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$, or —$CH_2$—$R^7$ wherein $R^7$ is selected from C3-C18 alkyl or C3-C18 alkenyl having one C=C double bond;
and wherein one or more of the nitrogen atoms indicated in formula (IV) may be protonated to provide a cationic group of formula (IV).

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

The oligo(alkylene amine) structures of formulae (II), (III) and (IV) are characterized in that they can combine shorter (also referred to for illustration as "S") ethylene amine units (i.e., a or b is 1) with longer (also referred to for illustration as "L") alkylene amine units (i.e., the other one of a or b is an integer of 2 to 4) in an alternating manner. Such an arrangement of the protonatable units can provide advantages in terms of the suitability of the resulting group to provide a vehicle for delivering polyribonucleotides into a cell.

A composition of the disclosure can comprise a plurality of oligo(alkylene amine) groups of formula (II) as a side chain or as a terminal group:

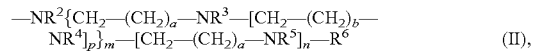

(II), wherein the variables a, b, p, m, n, and $R^2$ to $R^6$ are defined as follows, independently for each group of formula (II) in a plurality of such groups:
a is 1 and b is an integer of 2 to 4; or a is an integer of 2 to 4 and b is 1,
p is 1 or 2,
m is 1 or 2; n is 0 or 1 and m+n is 2; and
$R^2$ to $R^5$ are, independently of each other, selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$, or —$CH_2$—$R^7$ wherein $R^7$ is selected from C3-C18 alkyl or C3-C18 alkenyl having one C=C double bond; a protecting group for an amino group; —C(NH)—$NH_2$—; and a poly(ethylene glycol) chain;
$R^6$ is selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$, or —$CH_2$—$R^7$ wherein $R^7$ is selected from C3-C16 alkyl or C3-C16 alkenyl having one C=C double bond; a protecting group for an amino group; —C(NH)—NH; a poly(ethylene glycol) chain; and a receptor ligand.

In some cases, $R^2$ to $R^5$ are hydrogen and $R^6$ is selected from hydrogen, a protecting group for an amino group; —C(NH)—$NH_2$ and a poly(ethylene glycol) chain. In some cases, $R^2$ to $R^6$ are hydrogen. In some cases, $R^7$ is selected from C8-C18 alkyl or C8-C18 alkenyl having one C=C double bond, or from C8-C12 alkyl or C8-C12 alkenyl having one C=C double bond, or from C10-C12 alkyl or C10-C12 alkenyl having one C=C double bond. A composition of the disclosure can comprise one, or multiple alkylene groups of formulas (II)-(IV).

In some cases, the oligomers or polymers which can be used in the compositions in accordance with the present disclosure comprise a plurality of oligo (alkylene amine) groups of formula (III) as repeating units:

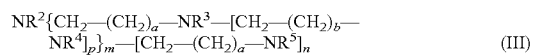

(III)

wherein the variables a, b, p, m, n, and $R^2$ to $R^5$ are defined as follows, independently for each group of formula (III) in a plurality of such groups:
a is 1 and b is an integer of 2 to 4; or a is an integer of 2 to 4 and b is 1, p is 1 or 2, m is 1 or 2; n is 0 or 1 and m+n is 2; and $R^2$ to $R^5$ are, independently of each other, selected from hydrogen; a group —$CH_2$—$CH(OH)$—$R^7$, —$CH(R^7)$—$CH_2$—OH, —$CH_2$—$CH_2$—(C=O)—O—$R^7$, —$CH_2$—$CH_2$—(C=O)—NH—$R^7$, —$CH_2$—$R^7$ or —$CH_2$— wherein $R^7$ is selected from C3-C18 alkyl or C3-C18 alkenyl having one C—C double bond; a protecting group for an amino group; —C(NH)—$NH_2$; a poly(ethylene glycol) chain; and endosomal escape effector and a receptor ligand. In some cases, $R^2$ to $R^5$ are hydrogen. In some cases, $R^7$ is selected from C8-C18 alkyl or C8-C18 alkenyl having one C—C. $R^7$ may be selected from C8-C12 alkyl or C8-C12 alkenyl having one C—C. As an alternative, $R^7$ may be selected from C10-C12 alkyl or C10-C12 alkenyl having one C—C.

One or more of the nitrogen atoms indicated in formula (III) may be protonated to provide a cationic group of formula (III).

Optionally, the oligomers or polymers which comprise a plurality of groups of formula (III) as repeating units can comprise, in addition, one or more oligo(alkylene amine) group(s) of formula (II) as a side chain and/or as a terminal group.

In a plurality of groups of formula (III) as repeating units, two, three or more of the groups of formula (III) can be contained in the oligomers or polymers. Generally, substances comprising 2 to 9 repeating units are referred to herein as oligomers, those comprising 10 and more repeating units as polymers. Thus, in the polymers containing a plurality of groups of formula (III) as repeating units, 10 or more groups of formula (III) may be present. It will be understood that the groups of formula (III) can have the same structure within a polymer or oligomer, or can have two or more different structures within the scope of formula (III). In some cases, the oligomers or polymers containing a plurality of groups of formula (III) as repeating units can be provided in the form of a library of sequence defined polymers which are prepared from different groups of formula (III) in a controlled, stepwise polymerization.

In line with formulae (II) and (III) above, an alkylene amine unit may be repeated once in an alternating chain such that oligo(alkylene amine) moieties of the type -S-L-L-S- or LS SL may result, wherein S represents a shorter ethylene amine unit, and L represents a longer alkylene amine unit. In some cases, groups of formula (II) and (III) are those wherein no repetition occurs, i.e., wherein p is 1, such that the shorter or longer units do not appear in pairs. The group of formula (II) can be an oligo(alkylene amine) group of formula (IIa) and the group of formula (III) can be an oligo(alkylene amine) group of (IIIa):

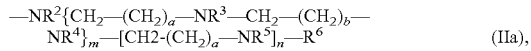

(IIa), wherein a, b, m, n, and $R^2$ to $R^6$ are defined as in formula (II), and wherein one or more of the nitrogen atoms indicated in formula (IIa) may be protonated to provide a cationic oligomer or polymer structure;

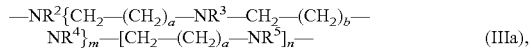

(IIIa), wherein a, b, m, n, and $R^2$ to $R^5$ are defined as in formula (III), and wherein one or more of the nitrogen atoms indicated in formula (IIa) can be protonated to provide a cationic oligomer or polymer structure.

Moreover, in some cases, the oligo(alkylene amine) group of formulae (II) and (III) can have an n of 1. In some cases, m is 1 and n is 1. In some cases, the group of formula (II) is an oligo(alkylene amine) group of formula (IIb), and the group of formula (III) is an oligo(alkylene amine) group of formula (IIIb):

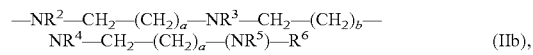

(IIb), wherein a, b, and $R^2$ to $R^6$ are defined as in formula (II), and wherein one or more of the nitrogen atoms indicated in formula (IIb) can be protonated to provide a cationic oligomer or polymer structure;

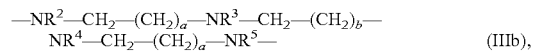

(IIIb), wherein a, b, and $R^2$ to $R^5$ are defined as in formula (III) and wherein one or more of the nitrogen atoms indicated in formula (IIIb) can be protonated to provide a cationic oligomer or polymer structure.

With respect to the length of the alkylene amine units in the oligo(alkylene amine) groups of formula (II), (IIa), (IIb) and (III), (IIIa), (IIIb), one of the alternating units can be an ethylene amine unit (i.e., either a or b is 1). The other alternating unit can be a propylene amine unit, a butylene amine unit or a pentylene amine unit (i.e., the other one of a or b can be an integer from 2 to 4. In some cases, the other of a or b can be 2 or 3, and in some cases, a is 1 and b is 2, or a is 2 and b is 1. In some cases, an oligo(alkylene amine) group of formula (IIc) is employed instead of or in addition to group (II), and/or an oligo(alkylene amine) group of formula (IIIc) is employed instead of or in addition to group (III). The formulae of group (IIc) and group (IIIc) are as follows:

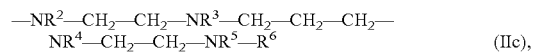

(IIc), wherein $R^2$ to $R^6$ are as defined in formula (II), and wherein $R^2$ to $R^6$ are hydrogen, and wherein one or more of the nitrogen atoms indicated in formula (IIc) can be protonated to provide a cationic oligomer or polymer structure;

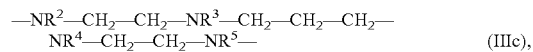

(IIIc), wherein $R^2$ to $R^5$ are as defined in formula (III), and wherein one or more of the nitrogen atoms indicated in formula (IIIc) can be protonated to provide a cationic oligomer or polymer structure.

In some cases, the groups $R^2$ to $R^6$ in formula (II), (IIa), (IIb) and (IIc) or the groups $R^2$ to $R^5$ in formula (III), (IIIa), (IIIb) and (IIIc) can be protecting group for an amino group. Non-limiting examples of protecting groups include t-butoxycarbonyl (Boc), 9-fluorenylmethoxycarbonyl (Fmoc), or carbobenzyloxy (Cbz).

In some cases, the groups $R^1$ to $R^6$ in formula (II), (IIa), (IIb) and (IIIc) or the groups $R^2$ to $R^5$ in formula (III), (IIIa), (IIIb) and (IIIc) are a receptor ligand, such as the receptor ligands described in Philipp and Wagner in "Gene and Cell Therapy—Therapeutic Mechanisms and Strategy", 3rd Edition, Chapter 15, CRC Press, Taylor & Francis Group LLC, Boca Raton 2009. Examples of receptor ligands that target the lung tissue are described in Pfeifer et al. 2010, Ther. Deliv. 1 (1): 133-48. Receptor ligands can include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that may bind to cell surface molecules (e.g., cell surface receptors), etc.

As far as any of the groups $R^1$ to $R^6$ in formula (II), (IIa), (IIb) and (IIc) or the groups $R^2$ to $R^5$ in formula (III), (IIIa), (IIIb) and (IIIc) are a poly(ethylene glycol) chain, the molecular weight of the poly(ethylene glycol) chain can be from about 100 g/mol to 20,000 g/mol, from about 1,000 g/mol to 10,000 g/mol or from about 1,000 g/mol to 5,000 g/mol.

In some cases, group (II) can be an oligo(alkylene amine) group of formula (IId):

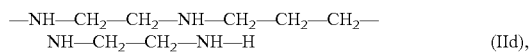

wherein one or more of the nitrogen atoms indicated in formula (IId) may be protonated to provide a cationic polymer or dendrimer structure. In some cases, group (III) is an oligo(alkylene amine) group of formula (IIId):

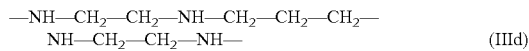

wherein one or more of the nitrogen atoms indicated in formula (IIId) may be protonated to provide a cationic polymer or dendrimer structure.

Lipidoids

An engineered polyribonucleotide can be encapsulated in a lipidoid formulation. A lipidoid formulation can be any material that has characteristics of a lipid, such as fats, waxes, sterols, fat-soluble vitamins (such as vitamins A, D, E, and K), monoglycerides, diglycerides, triglycerides, phospholipids, and others. For example, a lipid or lipidoid formulation can include lipids such as cholesterol, DOPE, DOPC or DSPC which are referred to as helper lipids in the scientific literature, and/or PEGylated lipids or any other lipid useful for preparing lipoplexes. The formulation comprising the engineered polyribonucleotide may be a nanoparticle which may comprise at least one lipid. A lipidoid formulation can be a lipid nanoparticle. The lipid may be selected from, but is not limited to, DOPE, DOPC, DSPC, cholesterol, DLin-DMA, DLin-K-DMA, 98N12-5, C12-200, DLin-MC3-DMA, DLin-KC2-DMA, DODMA, PLGA, PEG, PEG-DMG and PEGylated lipids. In another aspect, the lipid may be a cationic lipid such as, but not limited to, DLin-DMA, DLin-D-DMA, DLin-MC3-DMA, DLin-KC2-DMA and DODMA.

The composition containing a lipidoid may be about 40-60% lipidoid, about 40-60% cholesterol, and about 5-20% PEG-lipid (in percent by weight, based on the total weight of the composition). The composition containing a lipidoid may be about 50-60% lipidoid, about 40-50% cholesterol, and about 5-10% PEG-lipid. The composition containing a lipidoid may be about 50-75% lipidoid, about 20-40% cholesterol, and about 1-10% PEG-lipid. The composition containing a lipidoid may be about 60-70% lipidoid, about 25-35% cholesterol, and about 5-10% PEG-lipid. The composition may be provided with techniques described in, for example, Akinc et al, 2007, Nat Biotech, 26, 561-569; Akinc et al, 2009, Mol Ther, 17, 872-9; Love et al, 2010, PNAS, 107, 1864-9; U.S. Pat. No. 8,450,298, O2006/138380). RNA/lipidoid complexes may form particles that are useful in the delivery of RNA, such as single-stranded RNAs or mRNAs, into cells.

A composition of the disclosure cab be an engineered polyribonucleotide encapsulated by a lipidoid of formula (IV)

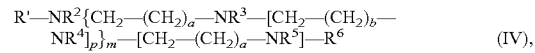

wherein the variables a, b, p, m, n and R1 to R6 are defined as follows:
a is 1 and b is an integer of 2 to 4; or a is an integer of 2 to 4 and b is 1,
p is 1 or 2,
m is 1 or 2; n is 0 or 1 and m+n is 2; and
$R^1$ to $R^6$ are independently of each other selected from hydrogen; a group —$CH_2$—CH(OH)—$R^7$, —CH($R^7$)—$CH_2$—OH, —$CH_2$—$CH_2$—(C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond; a protecting group for an amino group; —C(NH)—$NH_2$; a poly(ethylene glycol) chain; and a receptor ligand; provided that at least two residues among $R^1$ to $R^6$ are a group —$CH_2$—CH(OH)—CH($R^7$)—$CH_2$—OH, —$CH_2$—$CH_2$— (C=O)—O—$R^7$, —$CH_2$—$CH_2$—(C=O)—NH—$R^7$ or —$CH_2$—$R^7$ wherein $R^7$ is selected from C3-C18 alkyl or C3-C18 alkenyl having one C—C double bond.

In some cases, $R^1$ to $R^6$ are independently selected from hydrogen; a group —$CH_2$—C(OH)H—$R^7$ or —CH($R^7$)—$CH_2$—OH, wherein $R^7$ is selected from C3-C18 alkyl or C3-C18 alkenyl having one C—C double bond; a protecting group for an amino group; and a poly(ethylene glycol) chain; provided that at least two residues among $R^1$ to $R^6$ are a group —$CH_2$—C(OH)H—$R^7$ or —CH($R^7$)—$CH_2$—OH, wherein $R^7$ is selected from C3-C18 alkyl or C3-C18 alkenyl having one C—C double bond. In some cases, $R^1$ to $R^6$ are independently selected from hydrogen; and a group —$CH_2$—CH(OH)—$R^7$ or —CH($R^7$)—$CH_2$—OH wherein $R^7$ is selected from C3-C16 alkyl or C3-C16 alkenyl having one C—C double bond; provided that at least two residues among $R^1$ to $R^6$ are a group —$CH_2$—CH(OH)—$R^7$ or —CH($R^7$)—$CH_2$—OH, wherein $R^7$ is selected from C3-C18 alkyl or C3-C18 alkenyl having one C—C double bond. In some cases, $R^1$ and $R^6$ are independently selected from hydrogen; and a group —$CH_2$—CH(OH)—$R^7$ or —CH($R^7$)—$CH_2$—OH wherein $R^7$ is selected from C3-C18 alkyl or C3-C18 alkenyl having one C—C double bond; and $R^2$ to $R^5$ are all a group —$CH_2$—CH(OH)—$R^7$ or —CH($R^7$)—$CH_2$—OH wherein $R^7$ is selected from C3-C18 alkyl or C3-C18 alkenyl having one C—C double bond. In some cases, $R^7$ is selected from C8-C16 alkyl or C8-C18 alkenyl having one C—C double bond, or from C8-C12 alkyl or C8-C12 alkenyl having one C—C double bond, or from C10-C12 alkyl or C10-C12 alkenyl having one C—C double bond.

One or more of the nitrogen atoms indicated in formula (IV) may be protonated to provide a cationic lipidoid of formula (IV).

In line with formula (IV) above, an alkylene amine unit may be repeated once in an alternating chain such that oligo(alkylene amine) moieties of the type -S-L-L-S- or LS SL may result, wherein S represents a shorter ethylene amine unit, and L represents a longer alkylene amine unit. In some cases, a lipidoid of formula (IV) is one wherein no repetition occurs, i.e., wherein p is 1, such that the shorter or longer units do not appear in pairs. The lipidoid of formula (IV) can be a lipidoid of (IVa):

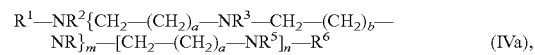

wherein a, b, m, n, and $R^1$ to $R^6$ are defined as in formula (IV) and wherein one or more of the nitrogen atoms indicated in formula (IVa) may be protonated to provide a cationic lipidoid;

In some cases, the lipidoid is a lipidoid of formula (IV). In some cases 'n' is 1 in a lipidoid of formula (IV). In some cases, 'm' is 1 and n is 1 in a lipidoid of formula (IV). In some cases, the lipidoid of formula (IV) is a lipidoid of formula (IVb):

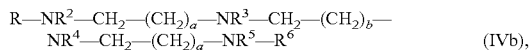
$$R-NR^2-CH_2-(CH_2)_a-NR^3-CH_2-(CH_2)_b-NR^4-CH_2-(CH_2)_a-NR^5-R^6 \quad (IVb),$$

wherein a, b, and $R^1$ to $R^6$ are defined as in formula (IV) wherein one or more of the nitrogen atoms indicated in formula (IVb) may be protonated to provide a cationic lipidoid.

As regards the length of the alkylene amine units in the lipidoid of formula (IV), (IVa) and (IVb), it will be understood that one of the alternating units needs to be an ethylene amine unit (i.e., either a or b is 1). The other alternating unit can be a propylene amine unit, a butylene amine unit, a pentylene amine unit, or another suitable unit (i.e., the other one of a or b is an integer of 2 to 4). In some cases, a lipidoid of formula (IV) is a lipidoid of formula (IVc):

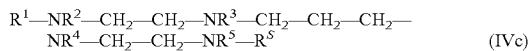
$$R^1-NR^2-CH_2-CH_2-NR^3-CH_2-CH_2-CH_2-NR^4-CH_2-CH_2-NR^5-R^5 \quad (IVc)$$

wherein $R^1$ to $R^6$ are as defined in formula (IV) and wherein one or more of the nitrogen atoms indicated in formula (IVc) can be protonated to provide a cationic lipidoid;

In some cases, the groups $R^1$ to $R^6$ in formula (IV), (IVa), (IVb) and (IVc) are a protecting group for an amino group. Non-limiting examples of protecting groups include t-butoxycarbonyl (Boc), 9-fluorenylmethoxycarbonyl (Fmoc), or carbobenzyloxy (Cbz).

As far as the groups $R^1$ to $R^6$ in formula (IV), (IVa), (IVb) and (IVc) are a receptor ligand, such as the receptor ligands described in Philipp and Wagner in "Gene and Cell Therapy—Therapeutic Mechanisms and Strategy", 3rd Edition, Chapter 15, CRC Press, Taylor & Francis Group LLC, Boca Raton 2009. Examples of receptor ligands that target the lung tissue are described in Pfeifer et al. 2010, Ther. Deliv. 1 (1): 133-48. Receptor ligands can include synthetic cyclic or linear peptides such as derived from screening peptide libraries for binding to a particular cell surface structure or particular cell type, cyclic or linear RGD peptides, synthetic or natural carbohydrates such as sialic acid, galactose or mannose or synthetic ligands derived from reacting a carbohydrate for example with a peptide, antibodies specifically recognizing cell surface structures, folic acid, epidermal growth factor and peptides derived thereof, transferrin, anti-transferrin receptor antibodies, nanobodies and antibody fragments, approved drugs that may bind to cell surface molecules (e.g., cell surface receptors), etc.

As far as the groups $R^1$ to $R^6$ in formula (IV), (IVa), (IVb) and (IVc) are a poly(ethylene glycol) chain, the molecular weight of the poly(ethylene glycol) chain can be from about 100 g/mol to 20,000 g/mol, from about 1,000 g/mol to 10,000 g/mol or from about 1,000 g/mol to 5,000 g/mol. In some cases, a molecular weight of the PEG chain can provide a composition with a desired density.

Multiple lipidoid molecules can be associated with an engineered polyribonucleotide. For example, a composition can comprise 1 engineered polyribonucleotide to 100 lipidoid molecules, 1 engineered polyribonucleotide to 1,000 lipidoid molecules, 10 engineered polyribonucleotide to 1,000 lipidoid molecules, or 100 engineered polyribonucleotide to 10,000 lipidoid molecules. The complex of engineered polyribonucleotide and lipidoid can form a particle. The diameter of the particles may range, e.g., from 10 nanometers to 1,200 nanometers. In some cases the diameter of the particles ranges from 10 nanometers to 500 nanometers. In some cases, the diameters of the particles are from 20 nanometers to 150 nanometers.

Administration to a Subject

Further described herein are methods for the administration of a polynucleotide (e.g., polyribonucleotide, nucleic acid construct, or vector) to a subject. The polyribonucleotide can be provided to the subject via a delivery agent, such as a particle or capsule with an encapsulating agent that encapsulates the polyribonucleotide. The delivery agent can be a therapeutic agent. The subject can be a human, such as a human afflicted with a disease or condition (e.g., primary ciliary dyskinesia (PCD), Kartagener Syndrome or cancer). The delivery agent can be administered to the subject (e.g., self-administration or administration by a third party, such as a healthcare provider) at a given dosage, and the dosage can be increased with time, decreased with time, or kept constant. The dosage can be changed based on a progression or regression of a disease in the subject, such as a rare disease or a cancer.

A polyribonucleotide of the disclosure can be formulated with one or more pharmaceutically acceptable carrier(s) to be administered to a subject. In some cases, the polyribonucleotide can be formulated for targeted delivery to a target cell or cell population. In some cases, the polyribonucleotide can be formulated for untargeted delivery to a cell or cell population. The encoded polypeptide product of the polyribonucleotide is then transcribed and it accumulates within the recipient cell.

A composition can be a combination of any engineered polyribonucleotide described herein with other chemical components, such as carriers, stabilizers, diluents, dispersing agents, suspending agents, thickening agents, and/or excipients. The composition facilitates administration of the compound to an organism. Pharmaceutical compositions can be administered in therapeutically-effective amounts as pharmaceutical compositions by various forms and routes including, for example, intravenous, subcutaneous, intramuscular, oral, rectal, aerosol, parenteral, ophthalmic, pulmonary, transdermal, vaginal, otic, nasal, and topical administration.

A composition can be administered in a local or systemic manner, for example, via injection of the compound directly into an organ, optionally in a depot or sustained release formulation. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For administration by inhalation, the active compounds can be in a form as an aerosol, a mist, a vapor, a spray, or a powder. Pharmaceutical compositions are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compounds and a suitable powder base such as lactose or starch.

The eye comprises several structurally and functionally distinct vascular beds that supply ocular components critical to the maintenance of vision. These beds include the retinal and choroidal vasculatures, which supply the inner and outer portions of the retina, respectively, and the limbal vasculature located at the periphery of the cornea.

A pharmaceutical composition comprising an engineered polyribonucleotide can be administered to the eye via any suitable form or route including, for example, topical, oral, systemic, intravitreal, intracameral, subconjunctival, sub-tenon, retrobulbar, intraocular, posterior juxtascleral, periocular, subretinal, and suprachoroidal administration. The compositions can be administered by injecting the formulation in any part of the eye including anterior chamber, posterior chamber, vitreous chamber (intravitreal), retina proper, and/or subretinal space. The compositions can also be delivered via a non-invasive method. Non-invasive modes of administering the formulation can include using a needleless injection device. Multiple administration routes can be employed for efficient delivery of the pharmaceutical compositions.

An engineered polynucleotide of the disclosure can be delivered to any suitable ocular cell including for example, endothelial cells such as vascular endothelial cells, cells of the retina such as retinal pigment epithelium (RPE), corneal cells, fibroblasts, astrocytes, glial cells, pericytes, iris epithelial cells, cells of neural origin, ciliary epithelial cells, mueller cells, muscle cells surrounding and attached to the eye such as cells of the lateral rectus muscle, orbital fat cells, cells of the sclera and episclera, cells of the trabecular meshwork, and connective tissue cells.

A composition that is disclosed herein, upon administration to a subject, can have a transfection efficiency of at least about 80%, 90%, or 95% by the cell of the subject. In some cases, the transfection efficiency of an encapsulated composition, upon administration to a subject, is at least about 50%, 60%, 70%, 80%, 90%, 95%, 100%, 110%, 120%, 130%, 140%, 150%, 160%, 170%, 180%, 190%, 200%, 225%, 250%, 275%, 300%, 325%, 350%, 375%, 400%, 450%, or 500% relative to an unencapsulated polyribonucleotide. In some situations, transfection efficiency of a composition comprising a modified polyribonucleotide (in some cases also comprising an unmodified polyribonucleotide), upon administration to a subject, is at least about 50%, 60%, 70%, 80%, 90%, 95%, 100%, 110%, 120%, 130%, 140%, 150%, 160%, 170%, 180%, 190%, 200%, 225%, 250%, 275%, 300%, 325%, 350%, 375%, 400%, 450%, or 500% relative to composition solely containing an unmodified polyribonucleotide. The transfection efficiency of a composition can be increased by addition of a carrier, such as a cell penetrating peptide or a cationic coating to the outer layer of the composition. The transfection efficiency of a composition can be modulated by the density of a composition.

Methods for the preparation of compositions comprising the engineered polyribonucleotides described herein include formulating the compounds with one or more inert, pharmaceutically-acceptable excipients or carriers to form a solid, semi-solid, or liquid composition. Solid compositions include, for example, powders, tablets, dispersible granules, capsules, cachets, and suppositories. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of pharmaceutically-acceptable excipients can be found, for example, in *Remington: The Science and Practice of Pharmacy*, Nineteenth Ed (Easton, Pa.: Mack Publishing Company, 1995); Hoover, John E., *Remington's Pharmaceutical Sciences*, Mack Publishing Co., Easton, Pa. 1975; Liberman, H. A. and Lachman, L., Eds., *Pharmaceutical Dosage Forms*, Marcel Decker, New York, N.Y., 1980; and *Pharmaceutical Dosage Forms* and Drug Delivery Systems, Seventh Ed. (Lippincott Williams & Wilkins 1999), each of which is incorporated by reference in its entirety.

A composition comprising a polynucleotide (e.g., polyribonucleotide) can be provided in various dosages. A dose of a polynucleotide, or a polyribonucleotide, can be from about 1 µg to about 1000 µg, about 1 µg to about 500 µg, about 1 µg to about 1000 µg, about 10 µg to about 500 µg, about 20 µg to about 500 µg, about 25 µg to about 500 µg, about 30 µg to about 500 µg, about 40 µg to about 500 µg, about 50 µg to about 500 µg, about 10 µg to about 250 µg, about 20 µg to about 250 µg, about 30 µg to about 250 µg, about 40 µg to about 250 µg, about 50 µg to about 250 µg, about 1 µg to about 200 µg, about 10 µg to about 200 µg, about 20 µg to about 200 µg, about 30 µg to about 200 µg, about 40 µg to about 200 µg, about 50 µg to about 200 µg, about 25 µg to about 50 µg, about 25 µg to about 100 µg, about 25 µg to about 150 µg, about 25 µg to about 200 µg, about 25 µg to about 250 µg, about 25 µg to about 300 µg, about 25 µg to about 350 µg, about 25 µg to about 400 µg, about 25 µg to about 450 µg, about 25 µg to about 500 µg, about 50 µg to about 750 µg, or about 25 µg to about 1000 µg of the engineered polyribonucleotide. In some cases, a dose of a polynucleotide is about 1 mg to about 100 mg, about 1 mg to about 50 mg, about 10 mg to about 50 mg, about 20 mg to about 50 mg, about 25 mg to about 50 mg, about 30 mg to about 50 mg, about 40 mg to about 50 mg, about 50 mg to about 100 mg, about 1 mg to about 25 mg, about 2 mg to about 25 mg, about 3 mg to about 25 mg, about 4 mg to about 25 mg, about 5 mg to about 25 mg, about 1 mg to about 20 mg, about 2 mg to about 20 mg, about 3 mg to about 20 mg, about 4 mg to about 20 mg, or about 5 mg to about 20 mg of an engineered polyribonucleotide.

The percentage of a polyribonucleotide in a formulation (e.g., within an encapsulated agent) can be greater than or equal to 0.25% polyribonucleotide, 0.5% polyribonucleotide, 0.75% polyribonucleotide, 1% polyribonucleotide, 1.25% polyribonucleotide, 1.5% polyribonucleotide, 1.75% polyribonucleotide, 2% polyribonucleotide, 2.25% polyribonucleotide, 2.5% polyribonucleotide, 2.75% polyribonucleotide, 3% polyribonucleotide, 3.25% polyribonucleotide, 3.5% polyribonucleotide, 3.75% polyribonucleotide, 4% polyribonucleotide, 4.25% polyribonucleotide, 4.5% polyribonucleotide, 4.75% polyribonucleotide, 5% polyribonucleotide, 5.25% polyribonucleotide, 5.5% polyribonucleotide, 5.75% polyribonucleotide, 6% polyribonucleotide, 6.25% polyribonucleotide, 6.5% polyribonucleotide, 6.75% polyribonucleotide, 7% polyribonucleotide, 7.25% polyribonucleotide, 7.5% polyribonucleotide, 7.75% polyribonucleotide, 8% polyribonucleotide, 8.25% polyribonucleotide, 8.5% polyribonucleotide, 8.75% polyribonucleotide, 9% polyribonucleotide, 9.25% polyribonucleotide, 9.5% polyribonucleotide, 9.75% polyribonucleotide, 10% polyribonucleotide, 10.25% polyribonucleotide, 10.5% polyribonucleotide, 10.75% polyribonucleotide, 11% polyribonucleotide, 11.25% polyribonucleotide, 11.5% polyribonucleotide, 11.75% polyribonucleotide, 12% polyribonucleotide, 12.25% polyribonucleotide, 12.5% polyribonucleotide, 12.75% polyribonucleotide, 13% polyribonucleotide, 13.25% polyribonucleotide, 13.5% polyribonucleotide, 13.75% polyribonucleotide, 14% polyribonucleotide, 14.25% polyribonucleotide, 14.5% polyribonucleotide, 14.75% polyribonucleotide, 15% polyribonucleotide, 15.25% polyribonucleotide, 15.5% polyribonucleotide, 15.75% polyribonucleotide, 16% polyribonucleotide, 16.25% polyribonucleotide, 16.5% polyribonucleotide, 16.75% polyribonucleotide, 17% polyribonucleotide, 17.25% polyribonucleotide, 17.5% polyribonucleotide, 17.75% polyribonucleotide, 18% polyribonucleotide, 18.25% polyribonucleotide, 18.5% polyribonucleotide, 18.75% polyribonucleotide, 19% polyribonucleotide, 19.25% polyribonucleotide, 19.5% polyribonucleotide, 19.75% polyribonucleotide, 20% polyribonucleotide, 20.5% polyribonucleotide, 21% polyribonucleotide, 21.5% polyribonucleotide, 22% polyribonucleotide, 22.5% polyribonucleotide, 23% polyribonucleotide, 23.5% polyribonucleotide, 24% polyribonucleotide, 24.5% polyribonucleotide, or 25% polyribonucleotide by weight. Alternatively, the percentage of the polyribonucleotide in the formulation (e.g., within an encapsulated agent) can be less than about 25% polyribonucleotide, 24.5% polyribonucleotide, 24% polyribonucleotide, 23.5% polyribonucleotide, 23% polyribonucleotide, 22.5% polyribonucleotide, 22% polyribonucleotide, 21.5% polyribonucleotide, 21% polyribonucleotide, 20.5% polyribonucleotide, 20% polyribonucleotide, 19.5% polyribonucleotide, 19% polyribonucleotide, 18.5% polyribonucleotide, 18% polyribonucleotide, 17.5% polyribonucleotide, 17% polyribonucleotide, 16.5% polyribonucleotide, 16% polyribonucleotide, 15.5% polyribonucleotide, 15% polyribonucleotide, 14.5% polyribonucleotide, 14% polyribonucleotide, 13.5% polyribonucleotide, 13% polyribonucleotide, 12.5% polyribonucleotide, 12% polyribonucleotide, 11.5% polyribonucleotide, 11% polyribonucleotide, 10.5% polyribonucleotide, 10% polyribonucleotide, 9.5% polyribonucleotide, 9% polyribonucleotide, 8.5% polyribonucleotide, 8% polyribonucleotide, 7.5% polyribonucleotide, 7% polyribonucleotide, 6.5% polyribonucleotide, 6% polyribonucleotide, 5.5% polyribonucleotide, 5% polyribonucleotide, 4.5% polyribonucleotide, 4% polyribonucleotide, 3.5% polyribonucleotide, 3% polyribonucleotide, 2.5% polyribonucleotide, 2% polyribonucleotide, 1.5% polyribonucleotide, 1% polyribonucleotide, 0.5% polyribonucleotide, or 0.1% polyribonucleotide.

In some cases, an encapsulated composition of the disclosure can produce a plasma, serum or blood concentration of the polyribonucleotide, pharmaceutical carrier, encapsulating agent, or polymeric material (e.g.: polyethylene glycol or polyethylenimine) in a subject within about 1 second to about 30 minutes, about 1 second to 20 minutes, about 1 second to 10 minutes, about 1 second to 5 minutes, about 1 second to 2 minutes, about 1 second to 1 minute, about 1 second to about 30 seconds, about 30 seconds to 30 minutes, about 30 seconds to 20 minutes, about 30 seconds to 10 minutes, about 30 seconds to 5 minutes, about 30 seconds to 2 minutes, about 30 seconds to about 1 minute, about 1 minute to about 30 minutes, about 1 minute to about 25 minutes, about 1 minute to about 20 minutes, about 1 minute to about 15 minutes, about 1 minute to about 10 minutes, about 5 minutes to about 30 minutes, about 5 minutes to about 25 minutes, about 5 minutes to about 20 minutes, about 5 minutes to about 15 minutes, about 5 minutes to about 10 minutes, about 10 minutes to about 30 minutes, about 10 minutes to about 25 minutes, about 10 minutes to about 20 minutes, or about 10 minutes to about 15 minutes of use of the device. The plasma, serum or blood concentration of the polyribonucleotide, pharmaceutical carrier, encapsulating agent, or polymeric material (e.g.: polyethylene glycol or polyethylenimine) concentration can be a peak concentration or an average concentration.

EXAMPLES

Example 1: Production of DNAI1 RNA Comprising

This experiment demonstrates the production of a DNAI1 complementary deoxyribonucleic acid construct.

Methods: DNAI1 was synthesized at GenScript. pUC57/DNAI1 was digested with HindIII and EcoRI HF restriction enzymes. Moreover, a digested pVAX120 vector and DNAI1 cDNA were gel purified and ligated (the ORF for DNAI1 is codon optimized). Standard in vitro translation procedure was used for RNA production utilizing unmodified nucleotides. Capping reaction was carried out using Vaccinia Virus capping system and cap 2'-O-methyl transferase. FIG. 1 is an agarose gel illustrating the production of capped and uncapped DNAI1 RNA. Note that in this experiment, the DNAI1 cDNA was ligated into pVAX120 to provide a construct that comprises a poly(A) tail.

Example 2: Expression of DNAI Ribonucleic Acid in Mammalian Cells

Figure 2:
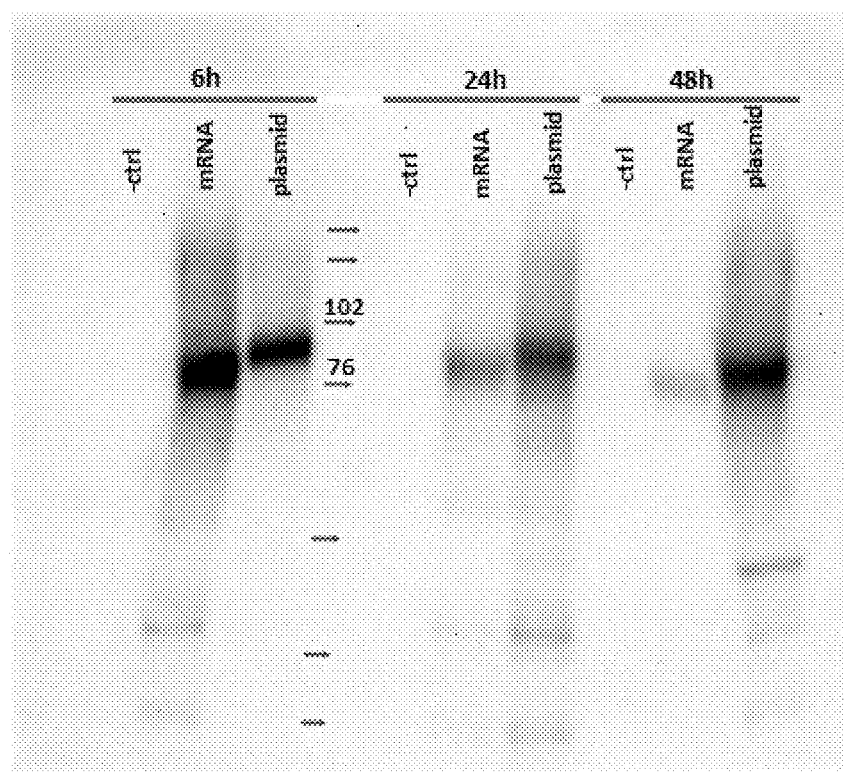
FIG. 2 is a western blot illustrating the translations of DNAI1 mRNA in HEK-293 cells at 6 hours, 24 hours, and 48 hours post-transfection.

This experiment demonstrates the expression (translation) of DNAI1 in HEK-293 cells. FIG. 2 is a western blot illustrating the translations of DNAI1 mRNA in 293 cells at 6 hours, 24 hours, and 48 hours post-transfection. For this experiment, 5×10$^5$ 293 cells/well in a 6 well plate were transfected with 2.5 µg of DNAI1 RNA using 3.75 µl messenger max transfection reagent. 6, 24, and 48 hours post transfection, cells were scraped from the wells, pelleted, and the pellet was lysed in RIPA buffer. The blot was probed with anti-DNAI1 ab166912 from Abcam. A C-terminal FLAG tagged DNAI1 plasmid DNA was transfected as a control, and the difference in MW between the plasmid and mRNA is likely due to the FLAG tag in the pENTRY vector.

Example 3: Formulation of a Composition Comprising an Engineered Polyribonucleotide for the Treatment of Human Subjects Afflicted with Primary Ciliary Dyskinesia Compositions are formulated as follows:

A nucleic acid construct encoding the DNAI1 gene sequence, NCBI Reference Sequence: NM_012144, is prepared as described in Example 1. Branched polyethylenimine is purchased from Sigma Aldrich™. Linear in vivo jetPEI® (polyethylenimine) is purchased from Polyplus Transfection® (Illkirch, France) and used without further purification. Following the manufacturer protocol, jetPEI is diluted in 5% glucose (final concentration) using the sterile 10% glucose solution provided by the manufacturer and HPLC-grade water purchased from Sigma-Aldrich (St. Louis, Mo.). After diluting the nucleic acid construct in 5% glucose (final concentration), the RNA and jetPEI solutions are combined/mixed at a ratio of 1:1 with a final N/P ratio of 8. The mRNA is then administered by intranasal instillation. Alternatively, the nucleic acid construct could also be formulated for administration by nebulizing or sniffing with a lipoplex formulation.

Example 4: Effects of Posttranscriptional Polyadenylation Reaction Times on RNA Quality The effect of the post-transcriptional polyadenylation reaction times on RNA quality was tested. Post in vitro transcription (IVT) poly-adenylation reaction times are typically 60-90 minutes long and usually provide polyA lengths that are at most about ~200 As. Because mRNA is susceptible to hydrolysis, it often degrades over time during the posttranscriptional poly-adenylation reaction. To maintain an optimal length for the DNAI1 poly A tail and to maximize RNA quality, a nucleic acid construct that encodes dynein axonemal intermediate chain 1 protein or a variant thereof with a poly A tail already included in the template was constructed.

A summary of the nucleic acid constructs encoding the DNAI1 gene sequence both with and without a poly-A sequence that were used to generate DNAI1 mRNAs are shown below:

TABLE 4

| Nucleic acid constructs encoding the DNAI1 gene sequence | Vector | Enzyme for Linearization | Codon-optimized | Nucleotide composition | Poly(A) post-IVT |
|---|---|---|---|---|---|
| DNAI1 | pCMV6Entry | Pme I | No | unmodified | yes |
| DNAI1 (SEQ ID NO: 14) | pVAX | NotI | Yes, GenScript | unmodified | No, Poly(A) sequence in template |

Figure 3:
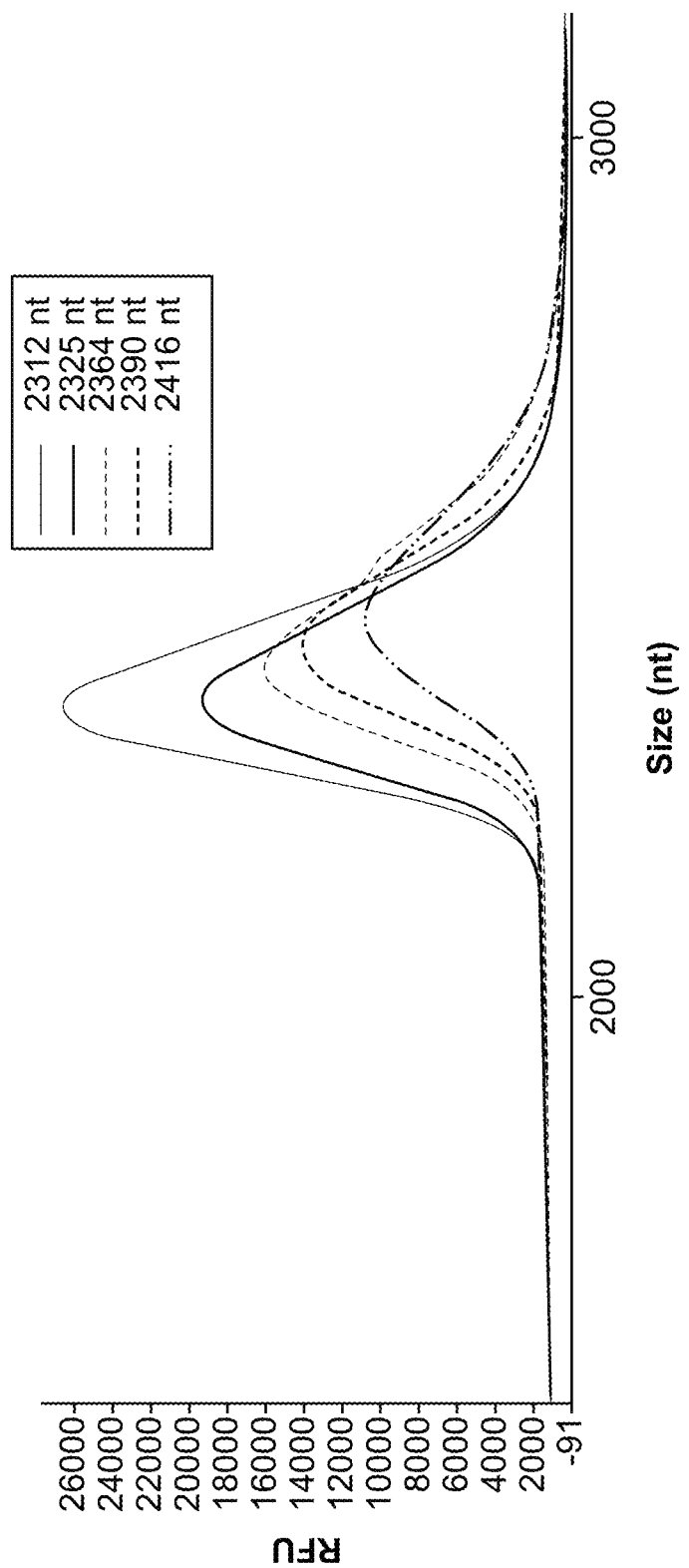
FIG. 3 illustrates fragment analyzer data of a posttranscriptionally poly-adenylated RNA transcript encoding dynein axonemal intermediate chain 1 (DNAI1).
Figure 4:
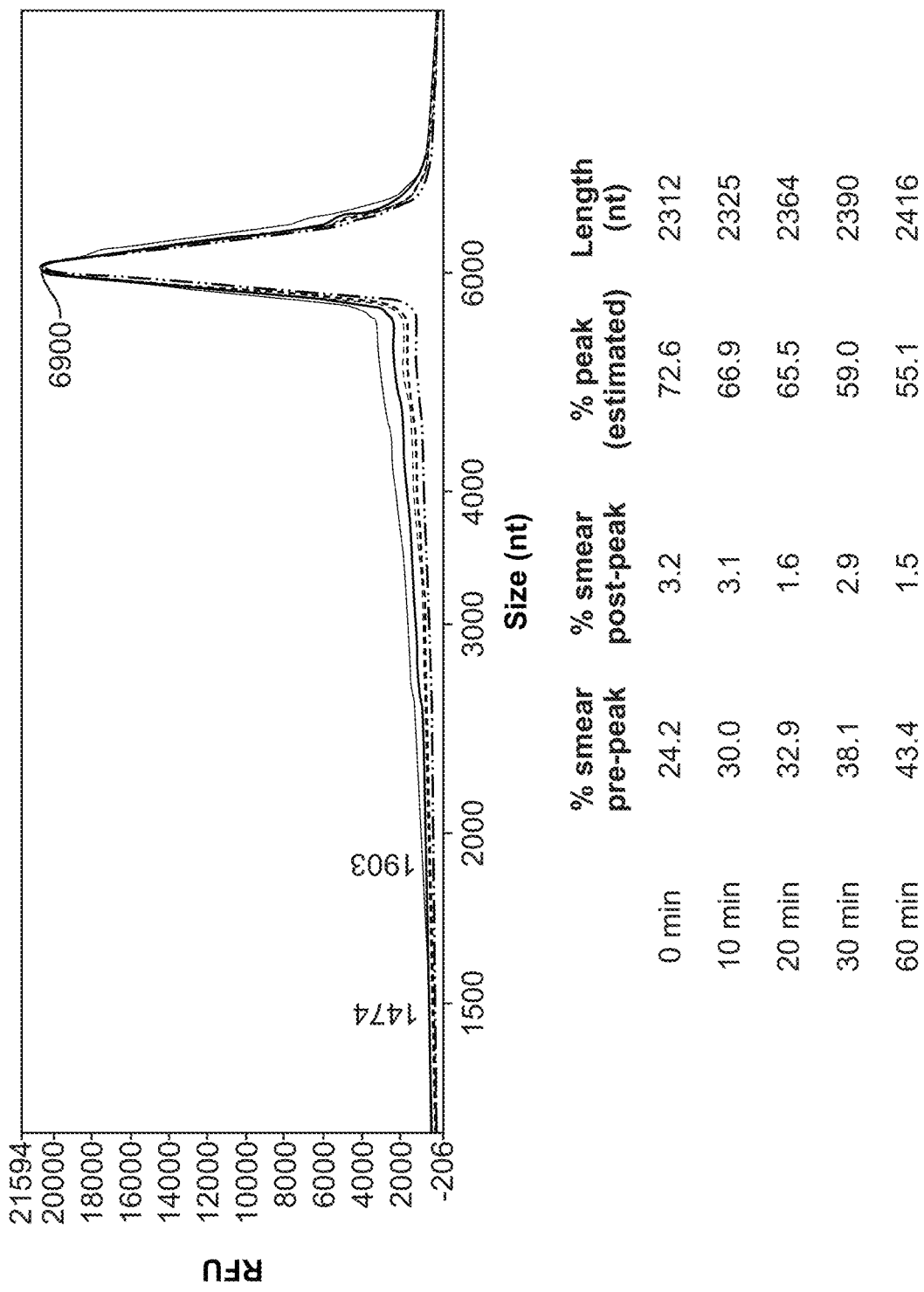
FIG. 4 illustrates fragment analyzer data of a posttranscriptionally poly-adenylated RNA transcript encoding dynein axonemal intermediate chain 1 (DNAI1).
Figure 5:
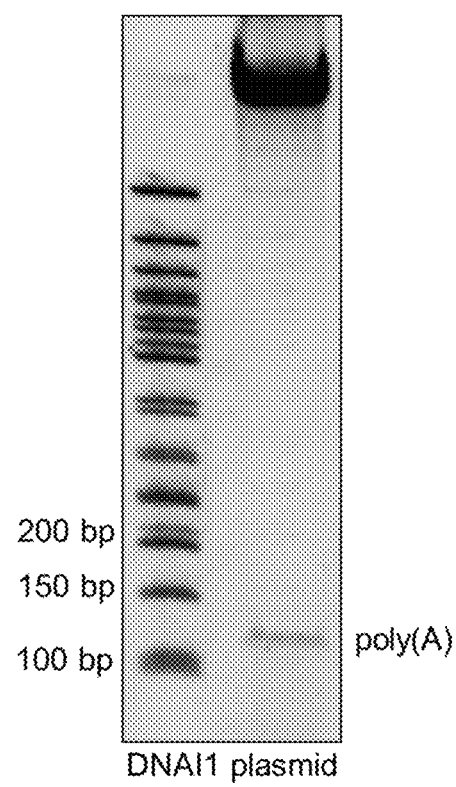
FIG. 5 illustrates PAGE data of the size of poly adenylated tail of the plasmid encoding dynein axonemal intermediate chain 1 (DNAI1).

FIG. 3 illustrates fragment analyzer data to determine the length of DNAI1 mRNAs produced from the DNAI1-pCMV6Entry plasmid that were post-transcriptionally poly-adenylated with reaction times from 0 to 60 min. This demonstrates increasing transcripts lengths with longer polyadenylation reaction times. FIG. 4 illustrates fragment analyzer data to examine the quality of these DNAI1 mRNAs that were post-transcriptionally poly adenylated with reaction times from 0 to 60 min. These results indicate that the RNA undergoes degradation as the poly-adenylation reaction proceeds as demonstrated by the reduction in % peak and increase in pre-peak smear % with longer reaction times. FIG. 5 illustrates the length of the poly-A sequence in the DNAI1-pVAX plasmid template as determined by 8% PAGE.

Example 5: RNA Production and Quality Control In Vitro

The following experiment was conducted to compare the effect of incorporating specific chemically-modified nucleotides, in varying ratios, on translation efficiency in different cell types and immunogenicity.

The experiments involved: 1) in vitro transcription of nucleic acid constructs; 2) in vitro capping of the nucleic acid constructs; 3) analysis of the integrity of the transcribed RNAs; 4) immuno-Dot-Blot Assay for dsRNAs; and 5) analysis of the nucleotide composition of the transcribed RNAs. General protocols for in vitro transcription (IVT) and capping of the RNAs were followed with a few modifications. IVT reactions for nucleic acid constructs encoding the DNAI1 gene were performed at 37° C. lasted for 6 h in the presence of 20 mM $MgCl_2$ and 7.5 mM of each ribonucleotide.

TABLE 5 illustrates various specific chemically-modified nucleotides that were transcribed in vitro from a nucleic acid construct that encodes dynein axonemal intermediate chain 1.

TABLE 5

| | Sample | Modified nucleotide composition of in vitro transcription reaction | 5' Cap | Vector backbone | 5' UTR | 3' UTR |
|---|---|---|---|---|---|---|
| 2 | DNAI1-RNA-002.2a (SEQ ID NO: 14) | Unmodified | Yes | pVAX | vector | vector |
| 3 | DNAI1-RNA-003.2a (SEQ ID NO: 14) | 50% Ψ | Yes | pVAX | vector | vector |
| 4 | DNAI1-RNA-004.2a (SEQ ID NO: 14) | 100% Ψ | Yes | pVAX | vector | vector |
| 5 | DNAI1-RNA-037.1a (SEQ ID NO: 14) | 100% m1Ψ | Yes | pVAX | vector | vector |

Results:
UV Measurements

TABLE 6

| | Sample | Modified nucleotide composition of in vitro transcription reaction | mg/mL | 260/280 |
|---|---|---|---|---|
| 2 | DNAI1-RNA-002.2a | unmodified | 0.944 | 2.22 |
| 3 | DNAI1-RNA-003.2a | 50% Ψ | 0.971 | 2.16 |
| 4 | DNAI1-RNA-004.2a | 100% Ψ | 0.940 | 2.13 |
| 5 | DNAI1-RNA-037.1a | 100% m1Ψ | 1.092 | 1.94 |

Template Poly(A) Length—Fragment Analyzer

Analysis of poly(A) tail length of the DNAI1 nucleic acid construct (SEQ ID NO: 5) used as a template for in vitro transcription indicated that the number of A residues was maintained in comparison to the original cloning vector (pVAX-A120). The initial vector contained 120 adenosine nucleotides, while a band between 100 and 150 bp was detected on this nucleic acid construct (FIG. 5). Templates were digested with Eco RI and Not I to remove the poly(A) fragment: 12 non-poly(A) nucleotides are expected to be part of the fragment. G*AATTCtgcag—poly(A)—GC*GGCCGC=12 nt plus the poly(A) in the EcoRI/NotI generated fragment.

RNA Smear Analysis—Fragment Analyzer

For all transcripts generated for DNAI1 a peak around 2,000 nt was detected. Evaluation of the in vitro generated transcript on a Fragment Analyzer indicated that capped transcripts maintained good integrity: limited detection of smear content (an indicator of RNA degradation and/or hydrolysis) was observed in repeated experiments. Briefly, 2 µL of 200 ng/µL samples were analyzed on a Fragment Analyzer (DNF-471 Standard Sensitivity RNA Analysis Kit (15nt Lower Marker). Data analysis was conducted using PROSize 2.0 software. The sizing accuracy is approximately within ±5%; the sizing precision is approximately within 5%

Figure 6:
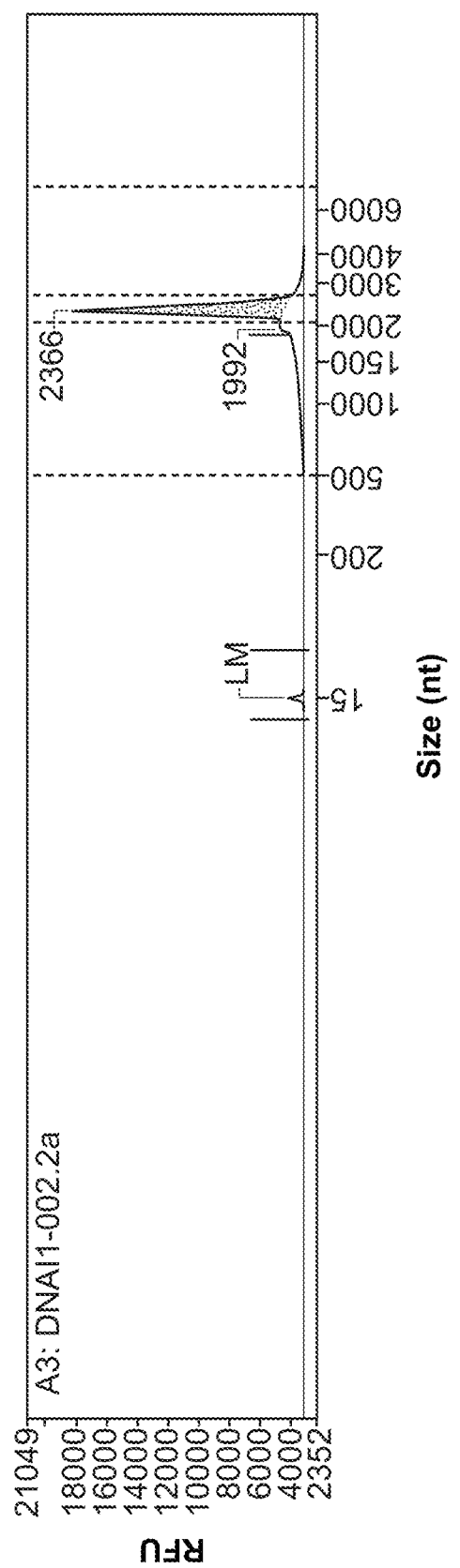
FIG. 6 illustrates the fragment analyzer data of an in vitro transcribed DNAI1 mRNA comprising the unmodified nucleotides.
Figure 7:
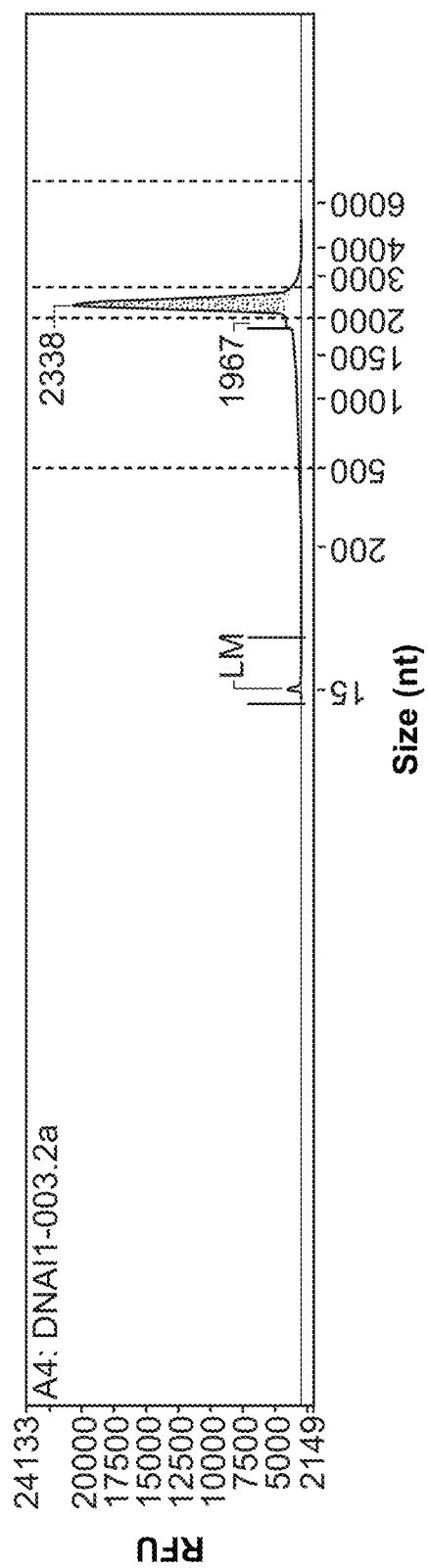
FIG. 7 illustrates fragment analyzer data of an in vitro transcribed DNAI1 mRNA comprising 50% pseudouridine (Ψ).
Figure 8:
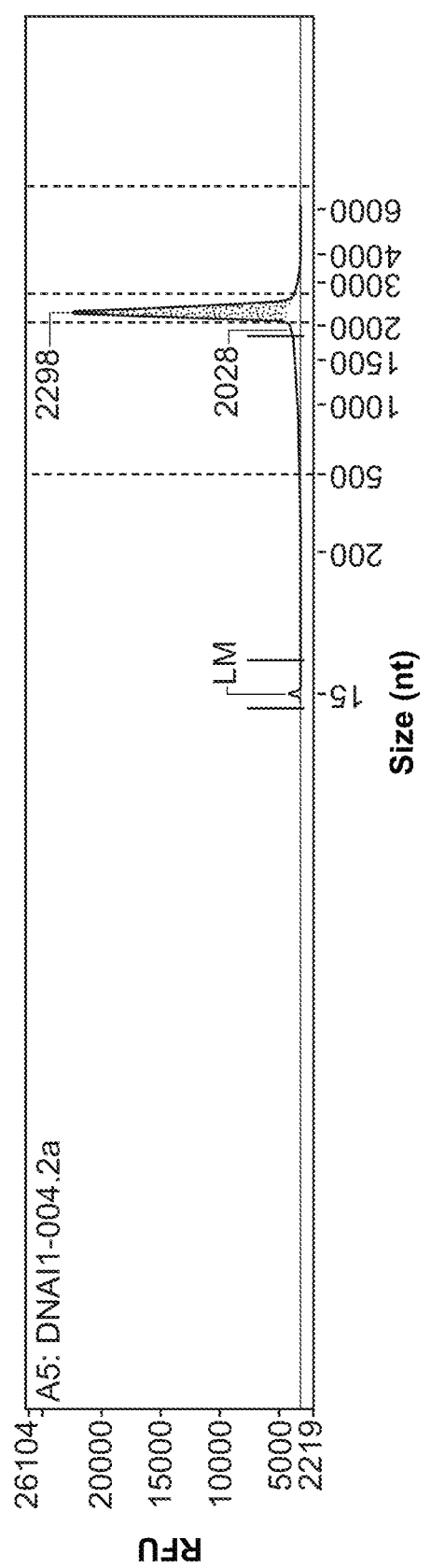
FIG. 8 illustrates fragment analyzer data of an in vitro transcribed DNAI1 mRNA comprising 100% pseudouridine (Ψ).
Figure 9:
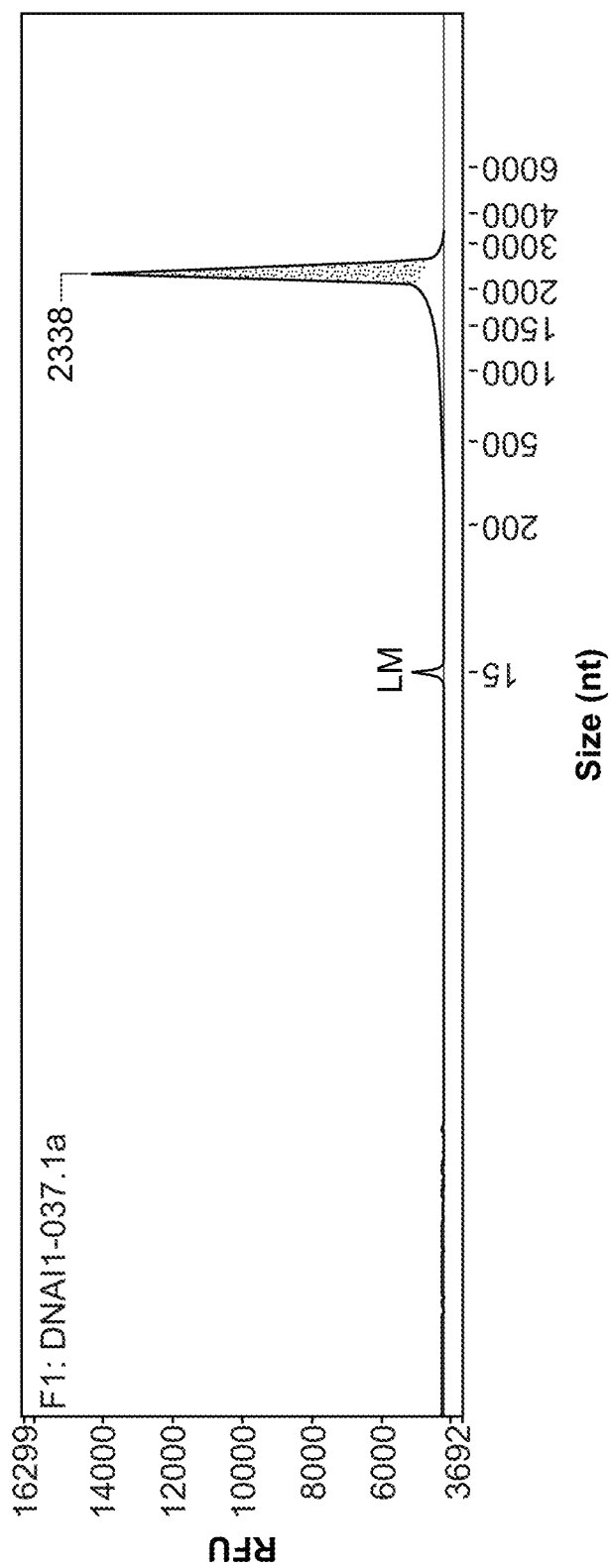
FIG. 9 illustrates fragment analyzer data of an in vitro transcribed DNAI1 mRNA comprising 100% 1-methylpseudouridine that was post-transcriptionally poly adenylated.

CV, the quantification accuracy is approximately within ±20%; and the quantification precision is approximately 10% CV. FIG. 6 illustrates the fragment analyzer data for the in vitro reaction comprising the canonical nucleotides only, namely: adenosine 5'-triphosphate, guanosine 5'-triphosphate, cytidine 5'-triphosphate, and uridine 5'-triphosphate. FIG. 7 illustrates the fragment analyzer data for the in vitro reaction comprising 50%/50% mixtures of pseudouridine and uridine 5'-triphosphate. FIG. 8 illustrates the fragment analyzer data for the in vitro reaction comprising 100% pseudouridine 5'-triphosphate. FIG. 9 illustrates the fragment analyzer data for the in vitro reaction comprising 100% 1-methyl-pseudouridine 5'-triphosphate. TABLE 7 summarizes the results of the RNA smear analysis.

TABLE 7

| Sample | % smear pre-peak | % smear post-peak | % full-length | Length |
|---|---|---|---|---|
| DNAI1-RNA-002.2a | 24.9 | 3.9 | 71.2 | 2366 |
| DNAI1-RNA-003.2a | 18.5 | 2.5 | 79.0 | 2338 |
| DNAI1-RNA-004.2a | 16.4 | 3.0 | 80.6 | 2298 |
| DNAI1-RNA-037.1a | 17.7 | 0.4 | 81.9 | 2338 |

Figure 10:
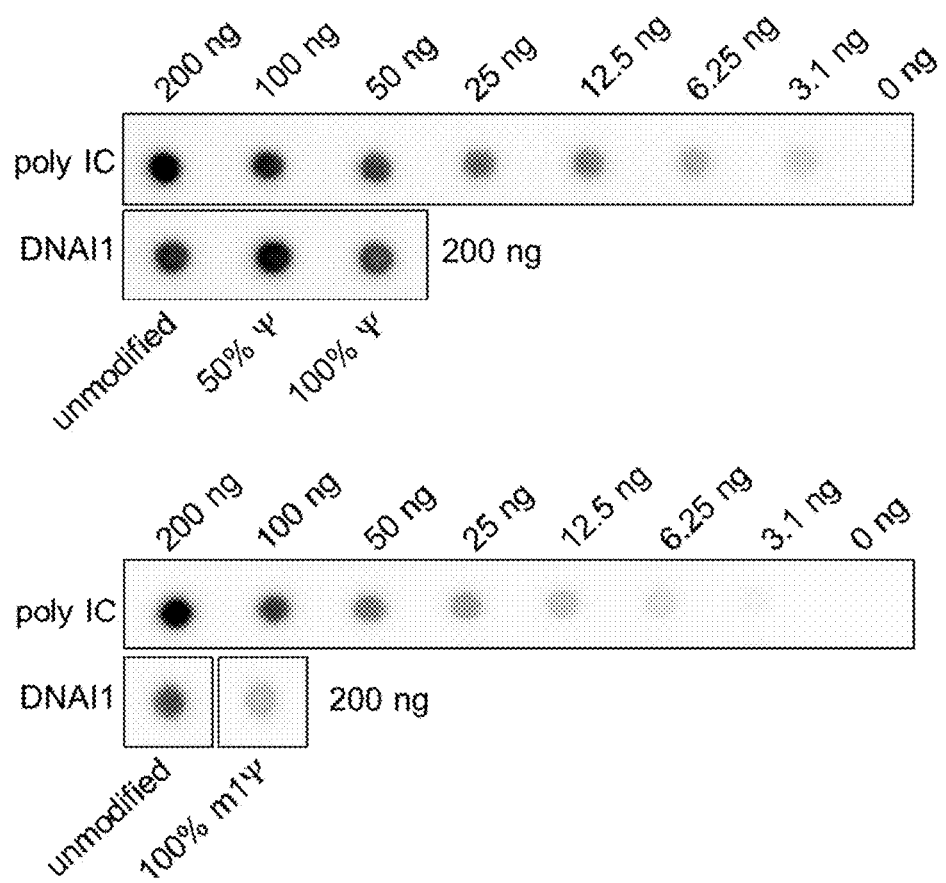
FIG. 10 illustrates double-stranded RNA content as detected by dot-blot.

Double-stranded RNA content as detected by dot-blot showed reactivity with J2 antibody. FIG. 10 illustrates double-stranded RNA content, as detected by dot-blot analysis, of in vitro transcribed RNAs from a nucleic acid construct that encodes dynein axonemal intermediate chain 1 as well as the double-stranded RNA content of DNAI1 constructs transcribed with the various specific modifications shown on TABLE 5.

Nucleoside Composition Analysis

Figure 11:
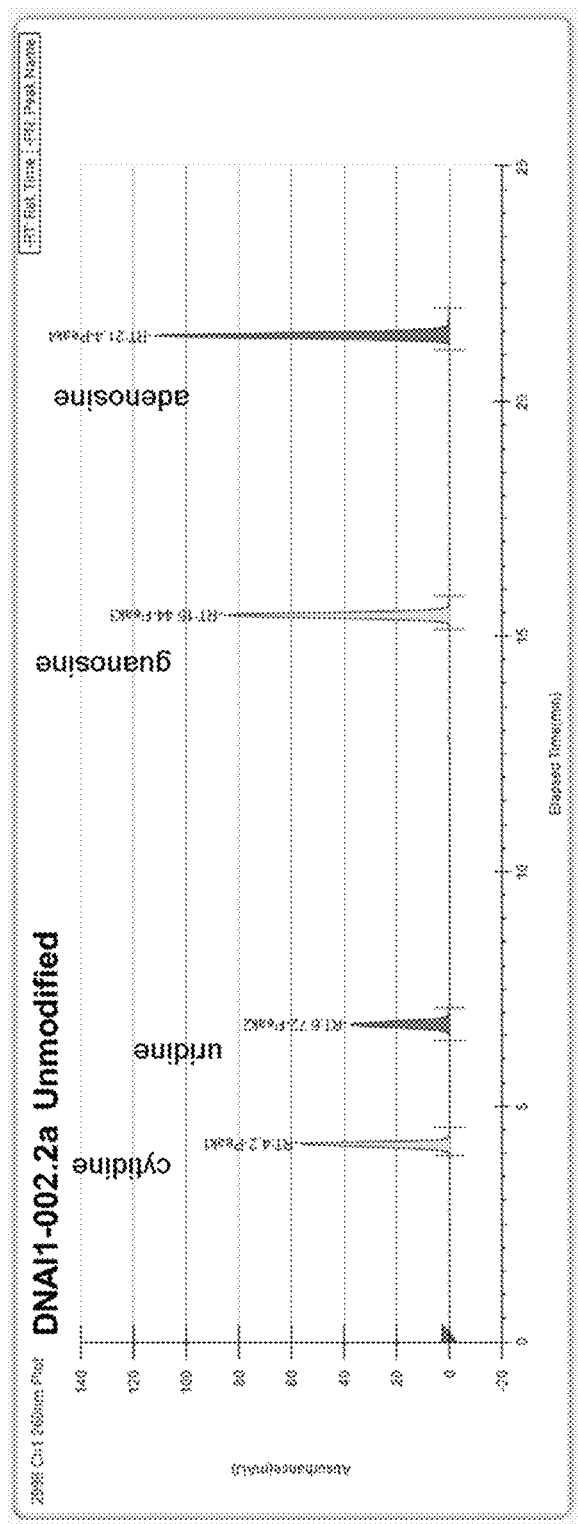
FIG. 11 illustrates the HPLC-based nucleotide composition analysis of an in vitro transcribed nucleic acid construct that encodes dynein axonemal intermediate chain 1, transcribed with unmodified nucleotides.
Figure 12:
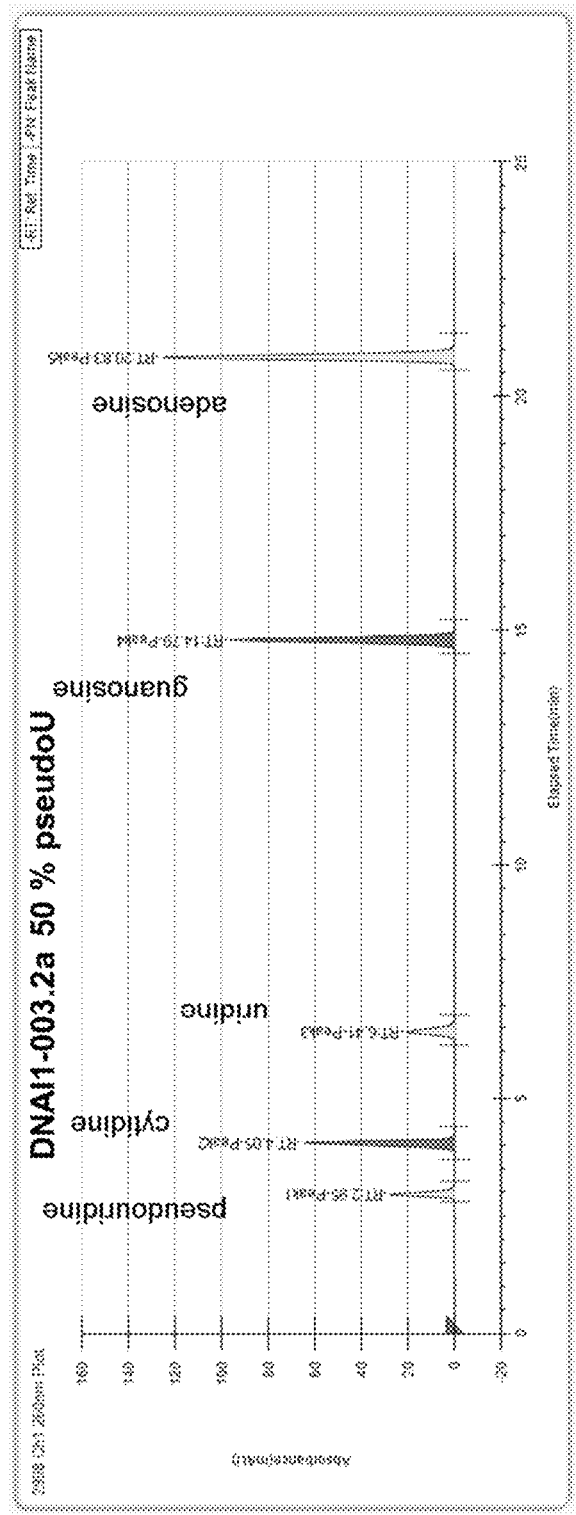
FIG. 12 illustrates the HPLC-based nucleotide composition analysis of an in vitro transcribed nucleic acid construct that encodes dynein axonemal intermediate chain 1, transcribed with 50% Ψ.
Figure 13:
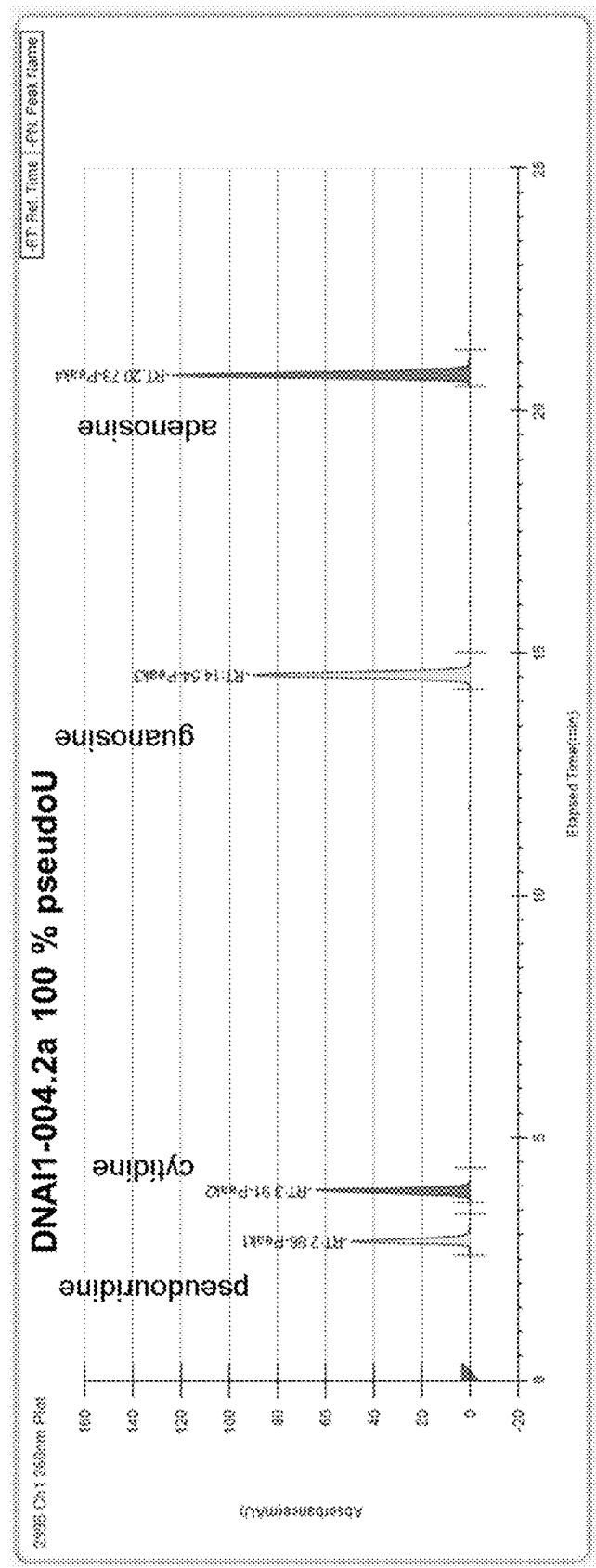
FIG. 13 illustrates the HPLC-based nucleotide composition analysis of an in vitro transcribed nucleic acid construct that encodes dynein axonemal intermediate chain 1, transcribed with 100% Ψ.

TABLES 8-10 illustrate the nucleotide composition analysis of in vitro transcribed RNAs from a nucleic acid construct that encodes dynein axonemal intermediate chain 1. The various specific nucleotide modifications are shown on TABLE 5. FIGS. 11-13 illustrate the corresponding HPLC chromatograms of individual ribonucleotides obtained after nuclease digestion of the transcripts and subsequent dephosphorylation.

TABLE 8 illustrates the nucleotide composition analysis of in vitro transcribed RNA from a nucleic acid construct that encodes dynein axonemal intermediate chain 1, transcribed with unmodified nucleotides. FIG. 11 illustrates the corresponding HPLC chromatogram.

TABLE 8

| Nucleotide composition (unmodified) | % abundance exp. [theoretical] |
|---|---|
| A | 28.9 [27.3] |
| C | 26.9 [26.5] |
| G | 26.6 [28.9] |
| U | 17.7 [17.3] |

TABLE 9 illustrates the nucleotide composition analysis of in vitro transcribed RNA from a nucleic acid construct that encodes dynein axonemal intermediate chain 1, transcribed with 50% pseudouridine. FIG. 12 illustrates the corresponding HPLC chromatogram. The retention time for the hydrophobic 1-methyl-pseudouridine using identical reverse-phase HPLC conditions averages ca. 9.5 minutes and is well separated from all other ribonucleotides investigated (data not shown).

TABLE 9

| Nucleotide composition | % abundance exp. |
|---|---|
| A | 28.2 |
| C | 27.0 |
| G | 26.9 |
| U | 8.1 |
| Ψ | 9.7 $(\varepsilon_{262})$ * |

* concentration estimated using empirical absorption coefficient ratio of $\varepsilon_{262}/\varepsilon_{260} = 1.001$ (Ψ)

TABLE 10 illustrates the nucleotide composition analysis of in vitro transcribed RNA from a nucleic acid construct that encodes dynein axonemal intermediate chain 1, transcribed with 100% pseudouridine. FIG. 13 illustrates the corresponding HPLC chromatogram.

TABLE 10

| Nucleotide composition | % abundance exp. |
|---|---|
| A | 28.8 |
| C | 26.5 |
| G | 26.9 |
| Ψ | 17.8 $(\varepsilon_{262})$ * |

* concentration estimated using empirical absorption coefficient ratio of $\varepsilon_{262}/\varepsilon_{260} = 1.001$ (Ψ)

Example 6: Translation Efficiency

The translation efficiency of the aforementioned DNAI1 transcripts was assessed in three cell lines: 1) HEK-293 human embryonic kidney cells; 2) A549 adenocarcinomic human alveolar basal epithelial cells; and 3) MLE-15 murine lung epithelial cells. Each cell line was transfected in triplicate with each DNAI1 transcript and the resulting cell extracts were analyzed for DNAI1 protein expression with western blotting. Briefly, either 1×10⁶ (HEK-293, MLE-15) or 2×10⁶ (A549) cells per well were plated 18 hours before transfection in 6-well plates. Cells were transfected with about 100 ng of each RNA using MessengerMax transfection reagent at a RNA:MessengerMax ratio of 1:37.5. Cells were harvested at 6 hours post-transfection and whole cell extracts were prepared in RIPA buffer (50 mM Tris-HCl pH 8, 150 mM NaCl, 1% Triton X-100, 0.1% SDS, 0.5% Sodium taurocholate). 3.5 µg of total protein from each extract was prepared in 1×LDS sample buffer containing 2.5% beta-mercaptoethanol and loaded on a 4-12% Bis-Tris SDS-PAGE gel. The gel was then run for 30 min. at 30 V constant voltage followed by 1 hour at 150 V. The proteins were transferred to PVDF membrane for 1 hour at 25 V in 1×NuPAGE transfer buffer containing 10% methanol. Following the transfer, DNAI1 protein was detected by western blot using an anti-DNAI1 antibody and developed using an alkaline phosphatase chemiluminescent substrate. The western blot values were normalized using Sypro Ruby total protein staining as a loading control and are expressed as relative expression to unmodified RNA. Each data point is the mean±standard deviation of three biological (transfection) replicates.

Figure 14:
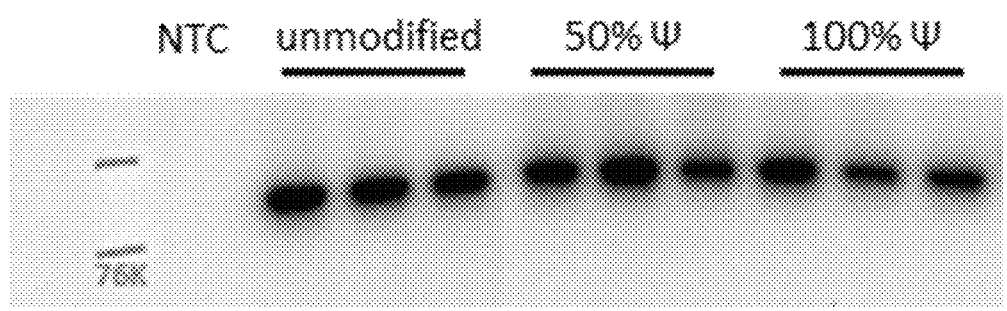
FIG. 14 is a graph illustrating the relative expression levels of DNAI1 protein in HEK-293, A549, and MLE-15 cells.
Figure 15:
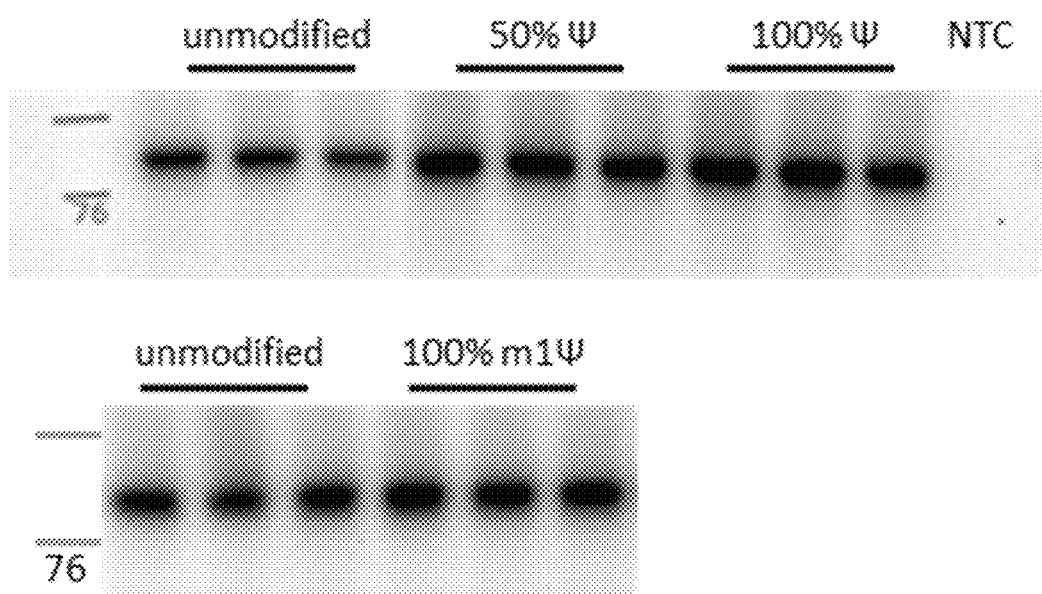
FIG. 15 illustrates the induction of IL-6 in A549 cells transfected with the DNAI1 mRNA variants.
Figure 16:
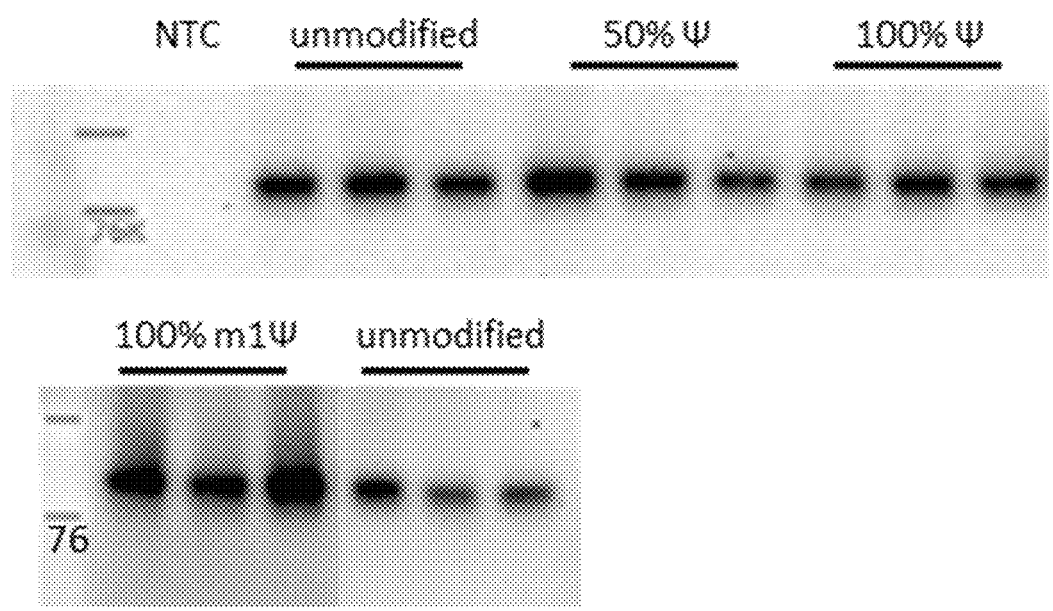
FIG. 16 illustrates the induction of IL-6 in A549 cells transfected with the DNAI1 mRNA variants.
Figure 17:
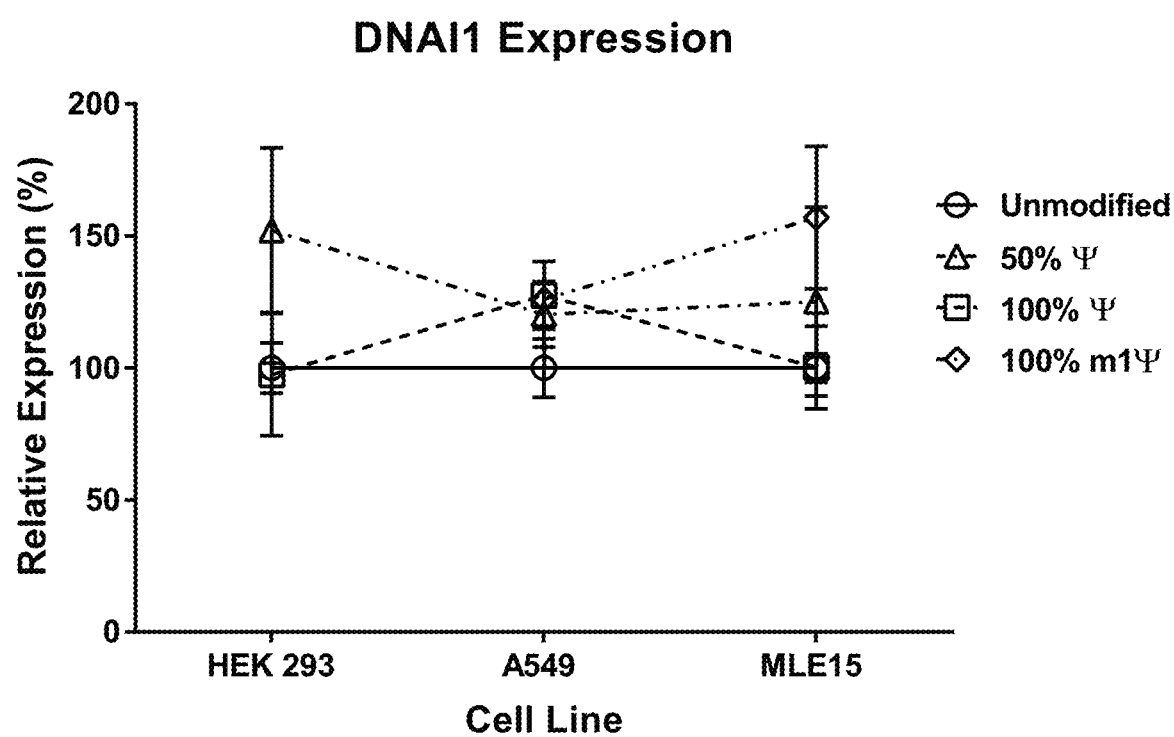
FIG. 17 is a graph illustrating the relative expression of DNAI1 protein in HEK-293, A549, and MLE-15 cells.

FIGS. 14, 15, and 16 illustrate the expression of DNAI1 protein in HEK-293, A549, and MLE-15 cells respectively. DNAI1 was expressed as a 699 amino acid, 79.3 kDa protein. The pseudouridine (Ψ) containing transcripts express well in all three cell types, with expression levels at or above the unmodified RNA. Similarly, the 1-methylpseudouridine (m¹Ψ)-containing transcript produced expression levels at or above the unmodified RNA in A549 and MLE15 cells (Expression in HEK-293 cells was not tested for this transcript). Importantly, the expression levels of each transcript and their relative rankings were similar in each cell line, indicating that there were no cell-type specific effects on DNAI1 translation. FIG. 17 is a graph illustrating the relative expression of DNAI1 protein in HEK-293, A549, and MLE-15 cells. Western blot signal values were normalized using total protein staining and are plotted as the mean expression ±std. dev. relative to the unmodified DNAI1 mRNA.

TABLE 11 is a summary of the relative expression of DNAI1 protein in each of the aforementioned cell lines.

TABLE 11

| Sample | Modified Nucleotide Composition | HEK-293 Cells Relative Expression (% ± Std. Dev). | A549 Cells Relative Expression (% ± Std. Dev). | MLE15 Cells Relative Expression (% ± Std. Dev). |
| --- | --- | --- | --- | --- |
| DNAI1-RNA-002.2a | Unmodified | 100 ± 9.57 | 100 ± 11.09 | 100 ± 5.35 |
| DNAI1-RNA-003.2a | 50% Ψ | 152.21 ± 31.21 | 120.36 ± 12.40 | 125.18 ± 35.84 |
| DNAI1-RNA-004.2a | 100% Ψ | 97.52 ± 23.12 | 127.57 ± 12.90 | 100.26 ± 15.71 |
| DNAI1-RNA-037.3a | 100% m1Ψ | n.d. | 126 ± 3 | 164 ± 17 |

Example 7: Immunogenicity of Nucleic Acid Constructs Encoding Human DNAI1 In Vitro The immunogenicity of the aforementioned transcripts was tested in two cell lines namely, A549 adenocarcinomic human alveolar basal epithelial cells and HepG2 human liver carcinoma cells, by measuring cytokine production. Production of IL-6 in response to the transcripts was measured in A549 cells, while production of IP-10 was measured in HepG2 cells. Each cell line was transfected in triplicate with a titration of each RNA. Briefly, either 20,000 (A549) or 40,000 (HepG2) cells per well were plated 24 hours prior to transfection in 96 well plates. The cells were then transfected with a titration of each transcript: From 250 ng to 7 ng per well for unmodified, 50% Ψ, and 100% Ψ transcripts; and from 1000 ng to 32 ng per well for the 100% mPP mRNA using MessengerMax reagent at a RNA:MessengerMax ratio of 1:1.5.

Culture supernatants were harvested at 18 hours post-transfection. Cell viability was measured immediately following supernatant removal using the CellTiter-Glo assay kit (Promega) which measures ATP levels as an indication of metabolically active cells. For IL-6 detection, A549 cell culture supernatants were diluted 1:20 in assay buffer and IL-6 levels were measured using the IL-6 High Sensitivity Human ELISA kit (Abcam ab46042). IP-10 was detected in undiluted HepG2 cell culture supernatants using the Human IP-10 ELISA Kit SimpleStep (Abcam ab173194).

Figure 18:
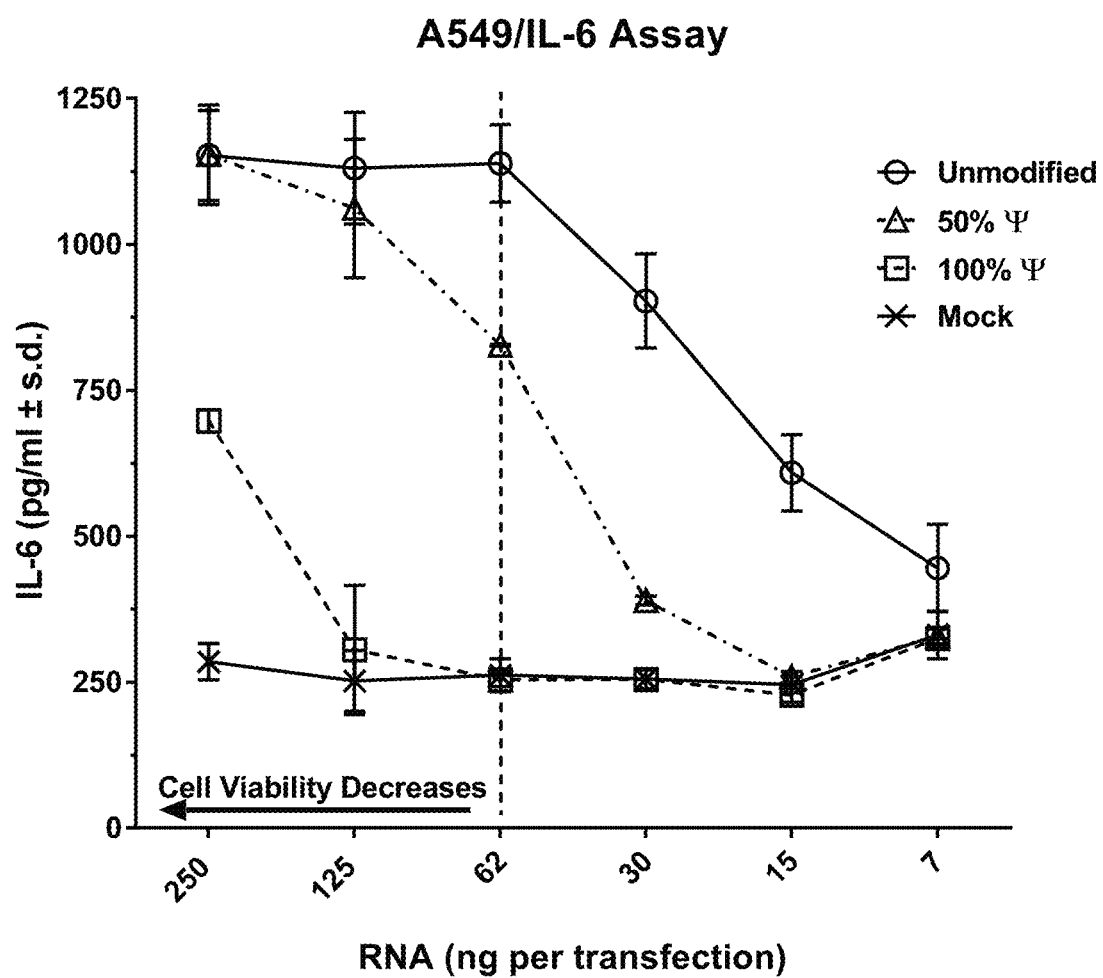
FIG. 18 illustrates induction of IL-6 in A549 cells by DNAI1 transcripts.
Figure 19:
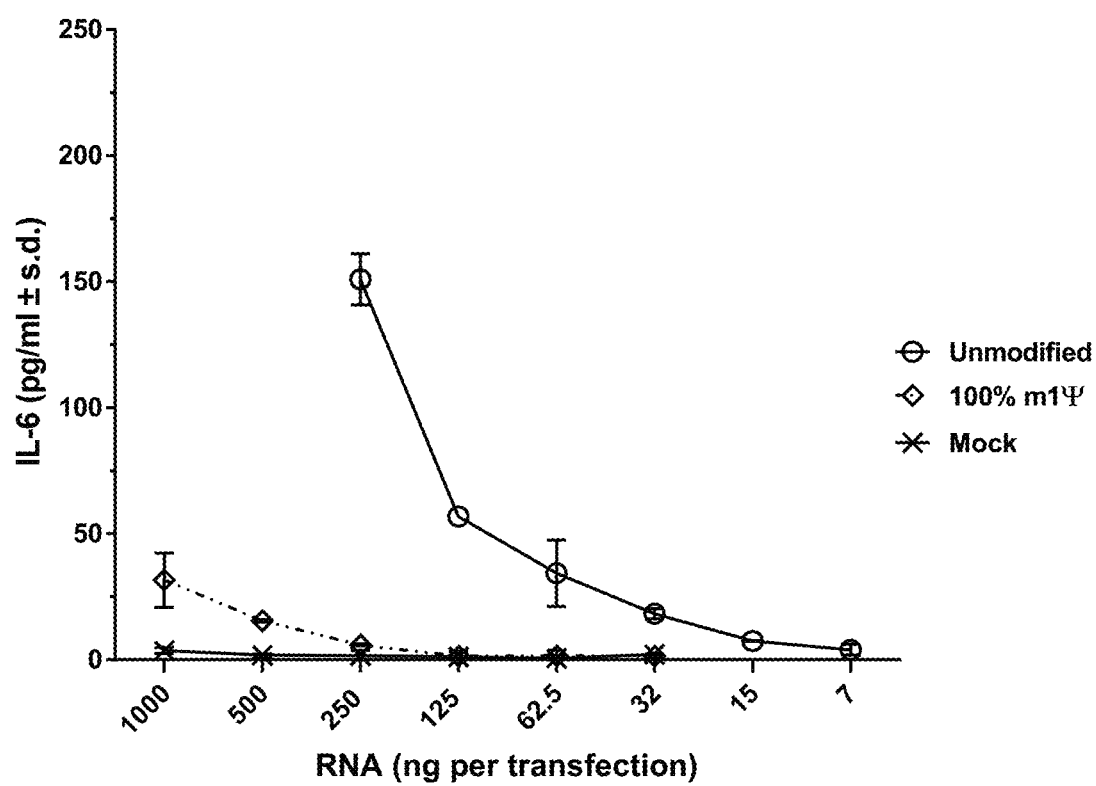
FIG. 19 illustrates induction of IL-6 in A549 cells by DNAI1 transcripts.
Figure 20:
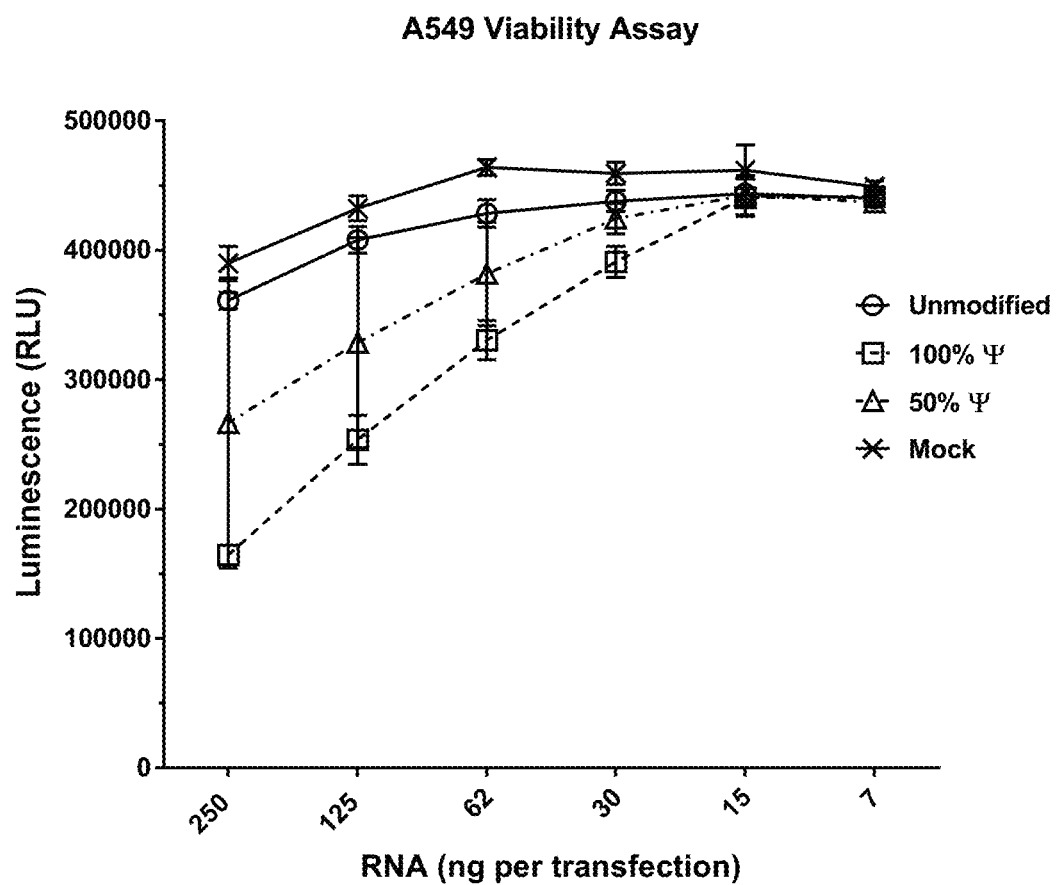
FIG. 20 illustrates cell viability of A549 cells after transfection with various amounts of each DNAI1 mRNA measured using the CellTiter-Glo assay.
Figure 21:
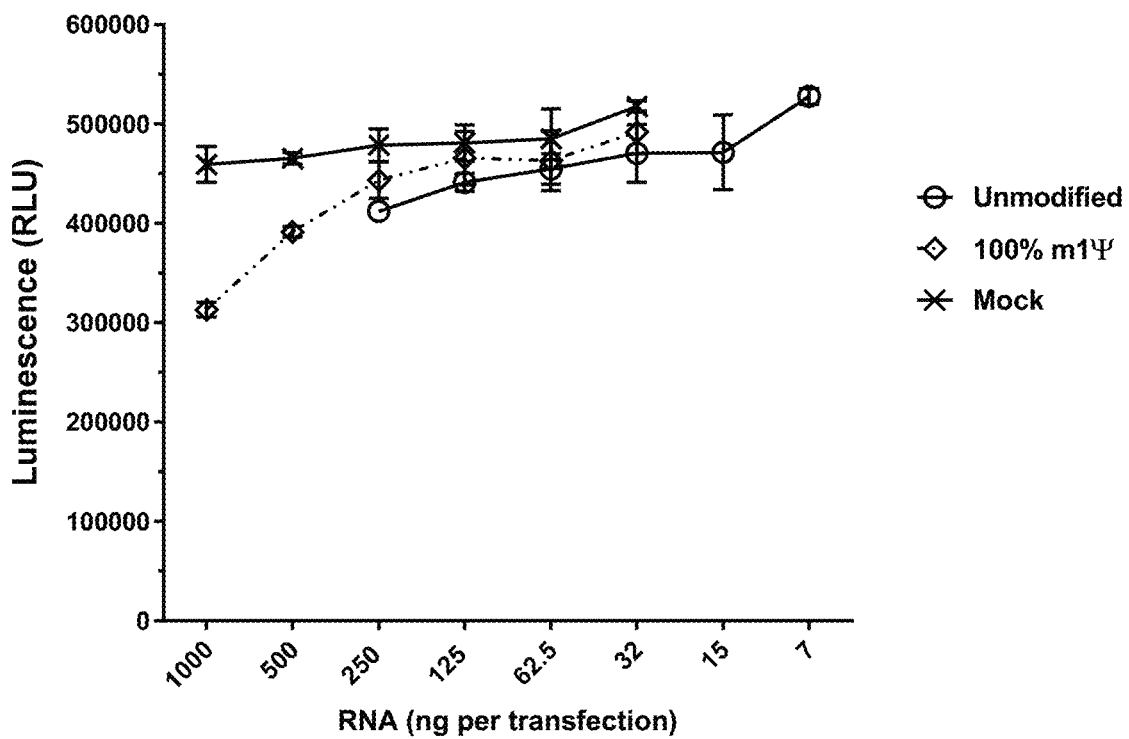
FIG. 21 illustrates cell viability of A549 cells after transfection with various amounts of each DNAI1 mRNA measured using the CellTiter-Glo assay.
Figure 22:
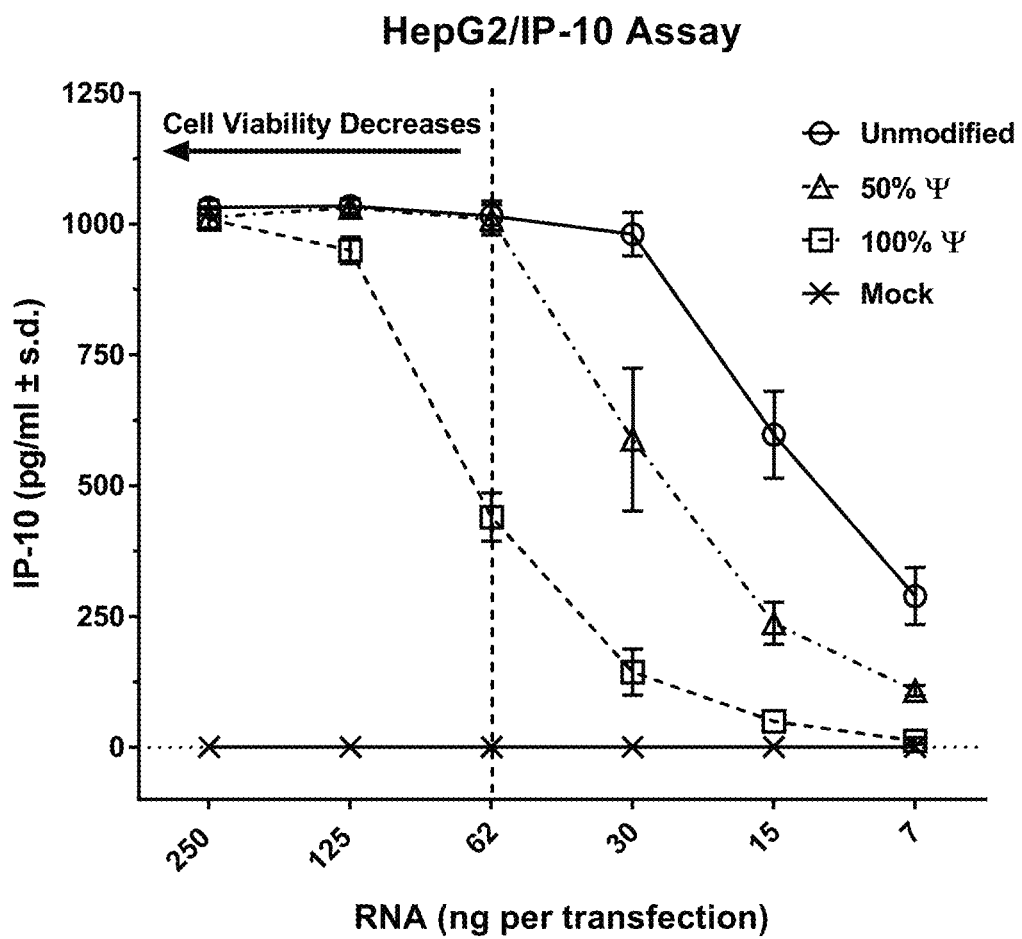
FIG. 22 illustrates induction of IP-10 in HepG2 cells by DNAI1 transcripts.
Figure 23:
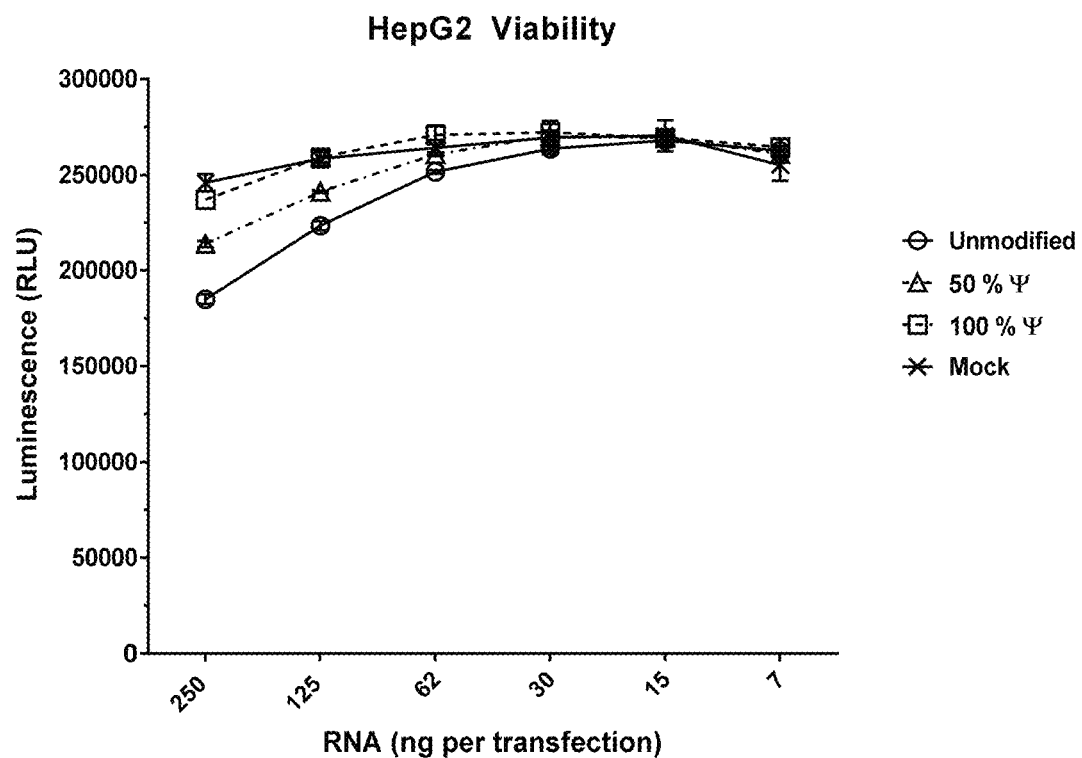
FIG. 23 illustrates cell viability of HepG2 cells after transfection with various amounts of each DNAI1 mRNA measured using the CellTiter-Glo assay.

FIGS. 18 and 19 illustrate the induction of IL-6 in A549 cells treated with the DNAI1 transcripts. For the assay shown in FIG. 18, cells were exposed to the RNA-MessengerMax complexes for 18 hrs, while for the assay shown in FIG. 19 the RNA-MessengerMax complexes were removed at 2 hrs post-transfection. In both cases the cell culture supernatants were harvested at 18 hrs for detection of IL-6 by ELISA. FIGS. 20 and 21 illustrate cell viability for the assay shown in FIGS. 18 and 19 as measured using the CellTiter-Glo assay. FIG. 22 illustrates induction of IP-10 in HepG2 cells by DNAI1 transcripts. For this assay, cells were exposed to the RNA-MessengerMax complexes for 18 hrs. IP-10 expression induced by various amounts of each DNAI1 mRNA was then measured by ELISA. FIG. 23 illustrates cell viability for the assay shown in FIG. 22 as measured using the CellTiter-Glo assay.

Example 8: Translation of DNAI1 mRNA in HEK293 Cells

Figure 24:
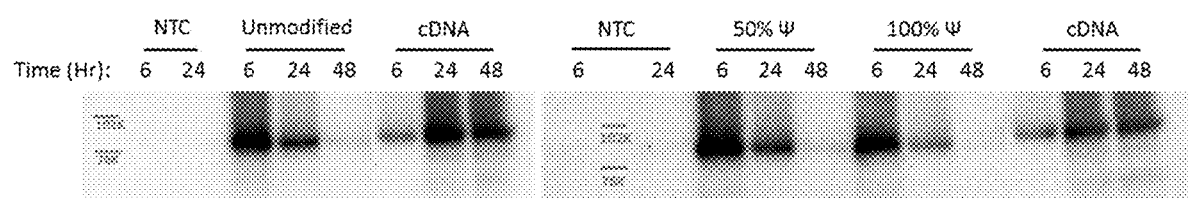
FIG. 24 illustrates the peak expression of dynein axonemal intermediate chain 1 (DNAI1) protein or other controls in HEK-293 cells.

FIG. 24 illustrates the peak expression of a nucleic acid encoding dynein axonemal intermediate chain 1 (DNAI1), or nucleic acid controls, in HEK293 cells. As shown in FIG. 24, in HEK293 cells, translation of DNAI1 nucleic acid construct in HEK293 cells peaks at 6 hours but is still present at 48 hours.

Figure 25:
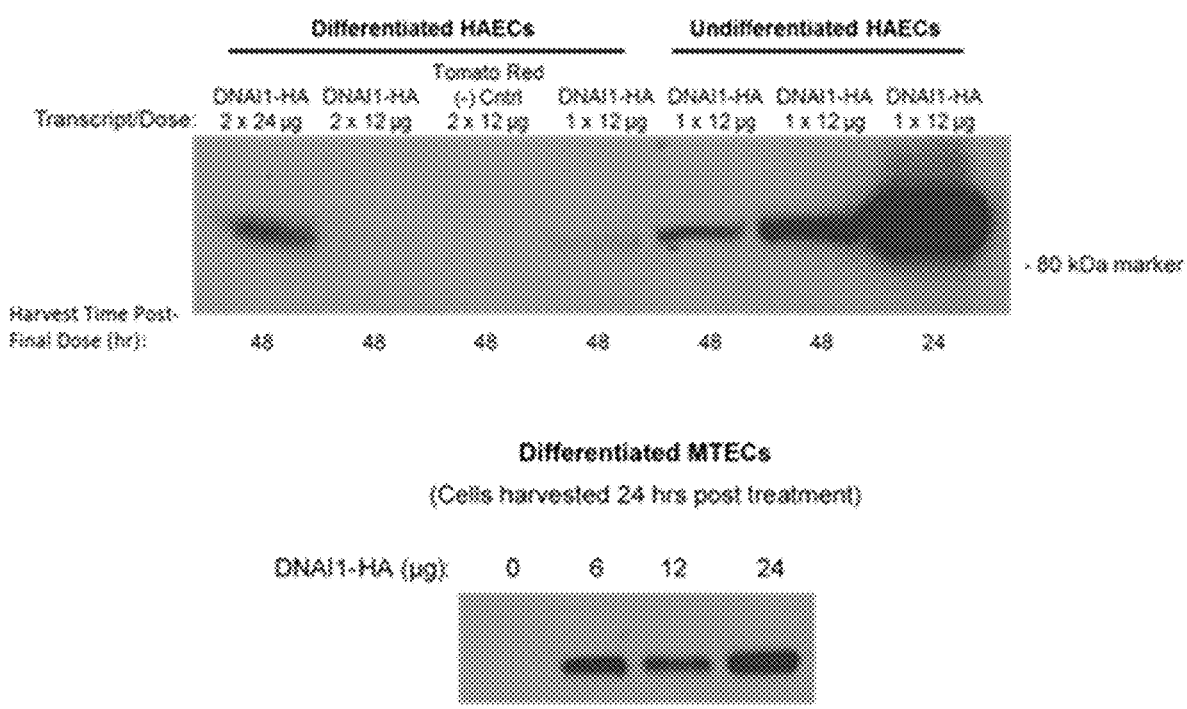
FIG. 25 expression of DNAI1 in fully differentiated human airway epithelial cells.

Example 9: Expression of DNAI1 Protein in Undifferentiated and Fully-Differentiated Human Airway Epithelial Cells (HAECs) and Mouse Tracheal Epithelial Cells (MTECs) Following Administration of Lipoplex-Formulated 100% m1 Ψ-Containing DNAI1 mRNA Expression of DNAI1 protein in primary human airway epithelial cells and mouse tracheal epithelial cells following treatment with lipoplex-formulated DNAI1-HA mRNA was assessed by western blot. The 100% m1Ψ-containing transcript used for this experiment was produced from a DNAI1 alternate codon usage template (SEQ ID NO 15) that contains an HA epitope tag. Primary human epithelial cells were maintained in submerged liquid culture for undifferentiated cultures or maintained at an air-liquid interface and allowed to differentiate for ~3 weeks into fully-differentiated ciliated epithelia. Next 12 or 24 µg of lipoplex-formulated DNAI1-HA mRNA was applied to the apical side of the fully-differentiated cultures or directly to the undifferentiated liquid cultures. Cells were treated either once or once per day for two consecutive days. Cells were then harvested at 24 or 48 hrs after the final treatment and whole cell extracts were prepared in RIPA buffer (50 mM Tris-HCl pH 8, 150 mM NaCl, 1% Triton X-100, 0.1% SDS, 0.5% Sodium taurocholate). Total protein from each extract was separated on a 4-12% Bis-Tris SDS-PAGE gel and transferred to PVDF membrane. DNAI1-HA protein was detected by western blot using an anti-HA antibody and developed using an enhanced chemiluminescent substrate. As shown in FIG. 25, DNAI1-HA protein was expressed at high levels in both the undifferentiated and fully-differentiated, ciliated human airway epithelial cells and in mouse tracheal epithelial cells.

Example 10: Altered Nucleotide Usage in Coding Regions Increases mRNA Stability for Transcript Therapy Altered nucleotide usage schemes aiming to reduce the number of more reactive dinucleotides within codons as well as across codons of modified mRNAs partially alleviate limitations imposed by the inherent chemical instability of RNA. At the same time, lowering the U-content in RNA transcripts renders them less immunogenic. Traditional codon optimization (CO) can be performed prior to (+) removal of reactive dinucleotide and (+) U-reduction in general yielding ORFs that are termed CO++.

Figure 27:
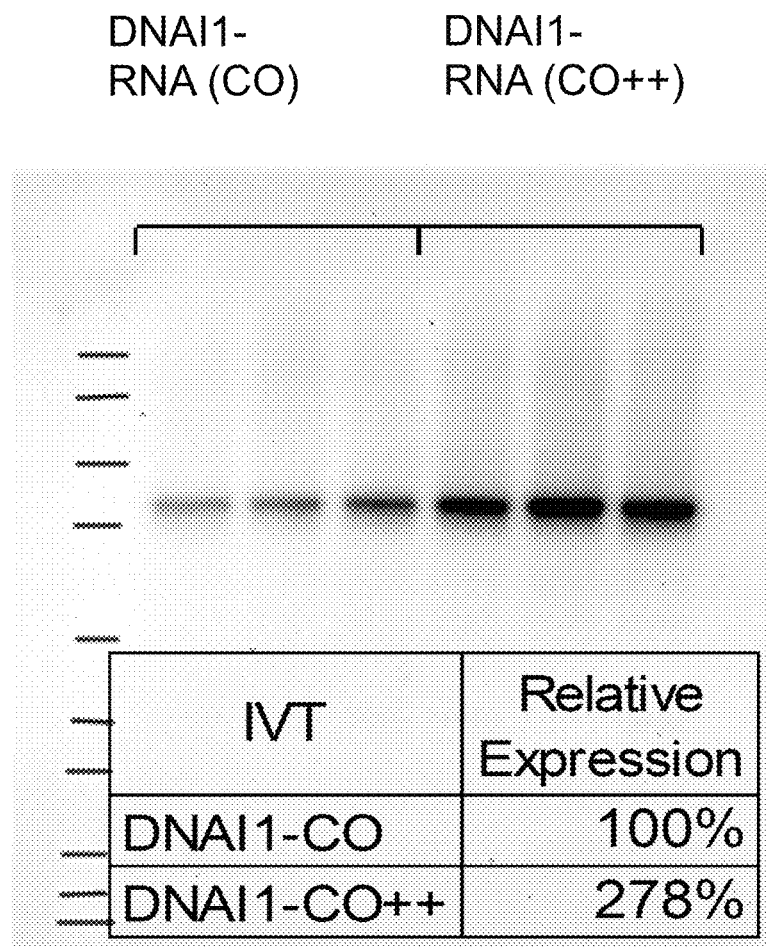
FIG. 27 illustrates an overall improvement in translation efficiency in A549 cells of a polyribonucleotide of SEQ ID NO 15 (B) as compared to a polyribonucleotide of SEQ ID NO 14 (A).

FIGS. 26A-26B illustrate an overall quality improvement in DNAI1 expressing a polyribonucleotide of SEQ ID NO 15 (B) as compared to a polyribonucleotide of SEQ ID NO 14 (A). The overall quality improvement is judged by the increasing main RNA peak % of the fragment analyzer traces in the polyribonucleotide engineered with the altered codon usage strategy. Furthermore, DNAI1 mRNA featuring the CO++-optimized open reading frame, i.e., altered codon usage, show an improvement in translation efficiency in transfected A549 cells when compared with transcripts that have been traditionally optimized (CO) (see FIG. 27). Here, 1.25×10⁶ cells per well were plated 18 hours before transfection in 6-well plates. Cells were transfected with about 100 ng of each RNA using MessengerMax transfection reagent at a RNA:MessengerMax ratio of 1:12 and harvested 6 h post transfection. Western blotting using an anti-DNAI1 antibody revealed DNAI1 protein expression as a 699 amino acid, 79.3 kDa protein. Relative translation efficiencies are indicated as the mean of three biological (transfection) replicates.

Figure 28:
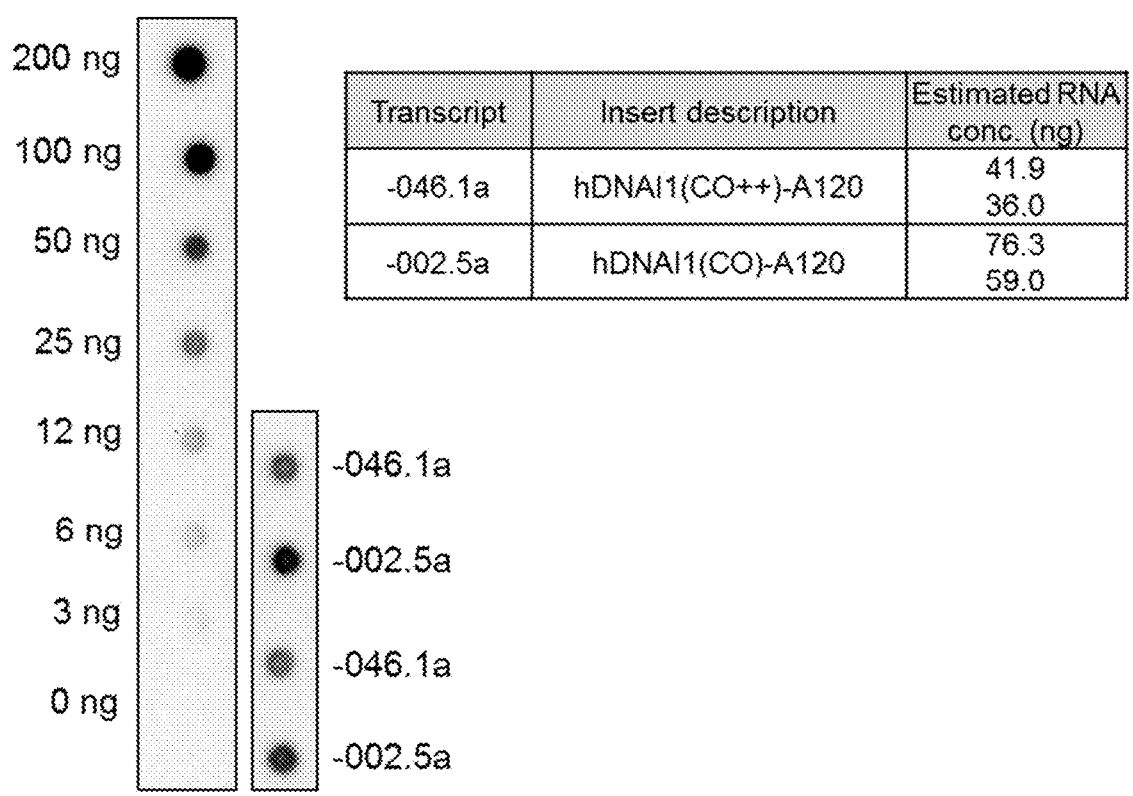
FIG. 28 illustrates an analysis of double-stranded RNA content of a polyribonucleotide of SEQ ID NO 15 as compared to known concentrations of known concentrations of poly-IC.
Figure 29A:
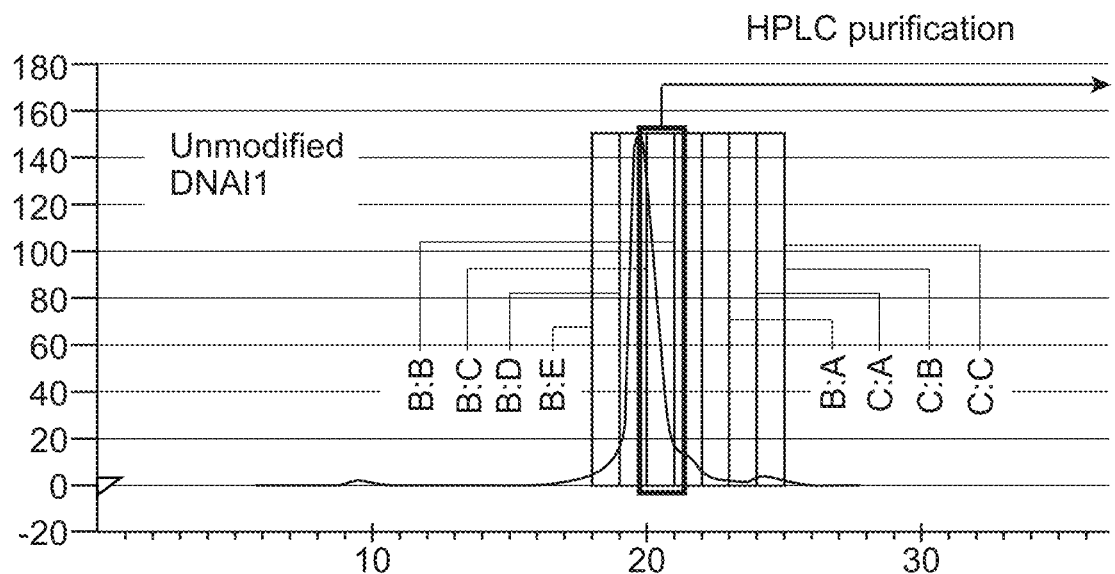
FIGS. 29A-29D illustrate HPLC-purification of unmodified and 100% $m^1\Psi$-containing DNAI1 mRNA.
Figure 29B:
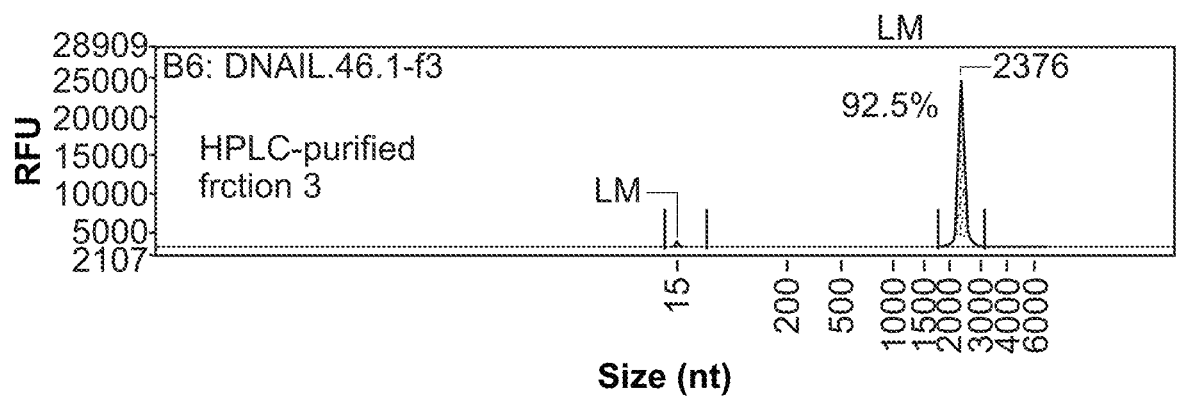
Figure 29B:
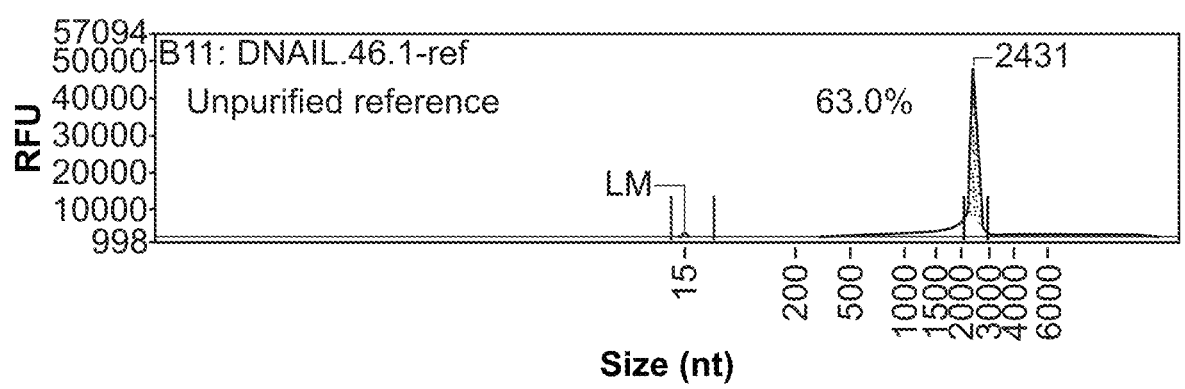
Figure 29C:
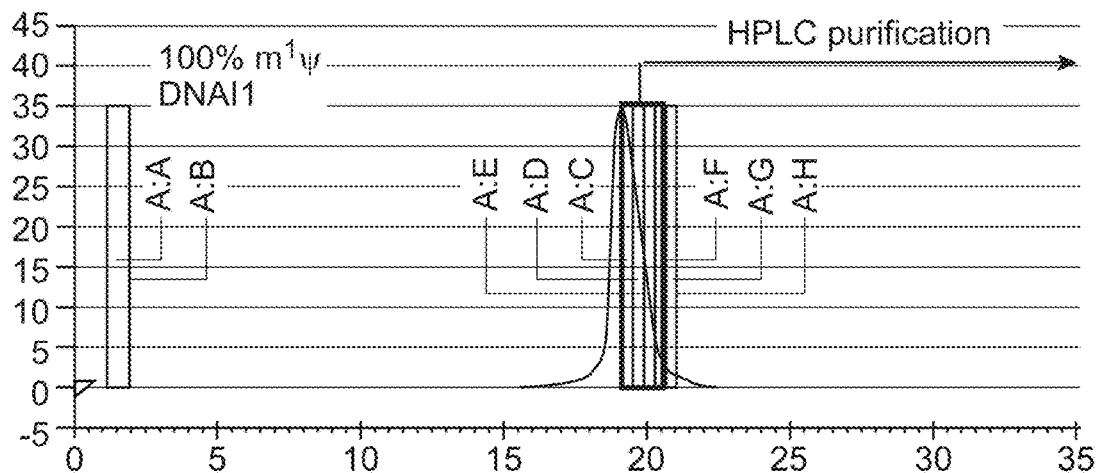
Figure 29D:
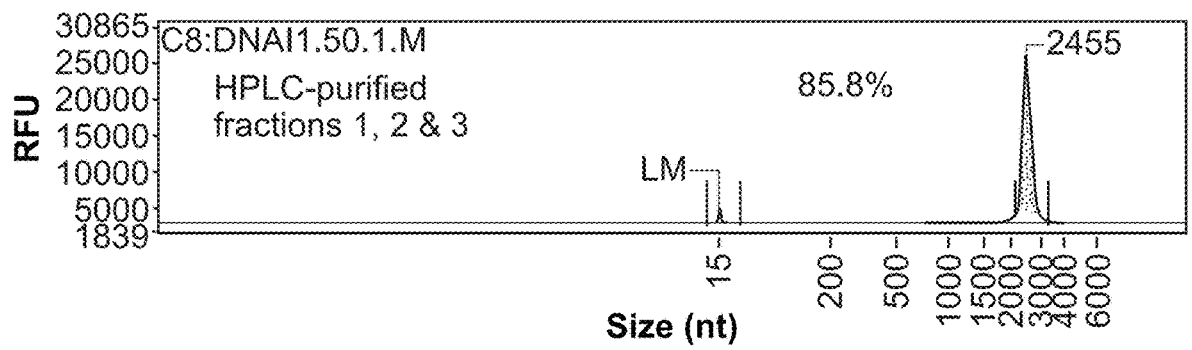
Figure 29D:
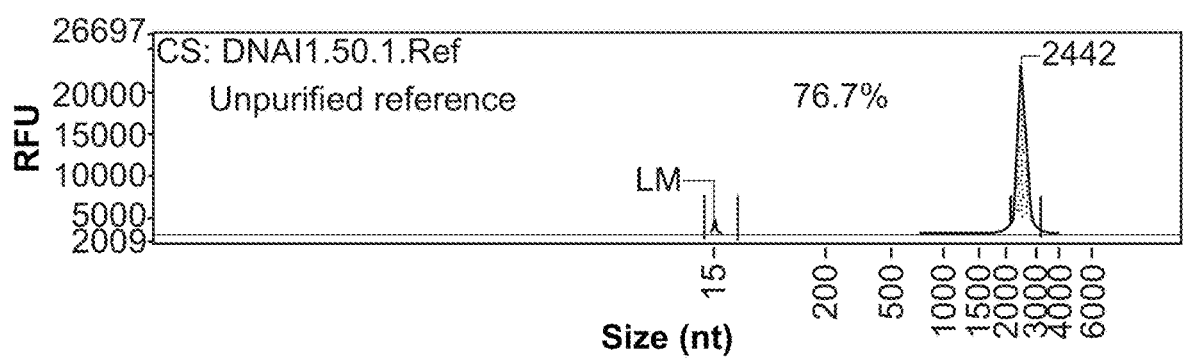
Figure 30A:
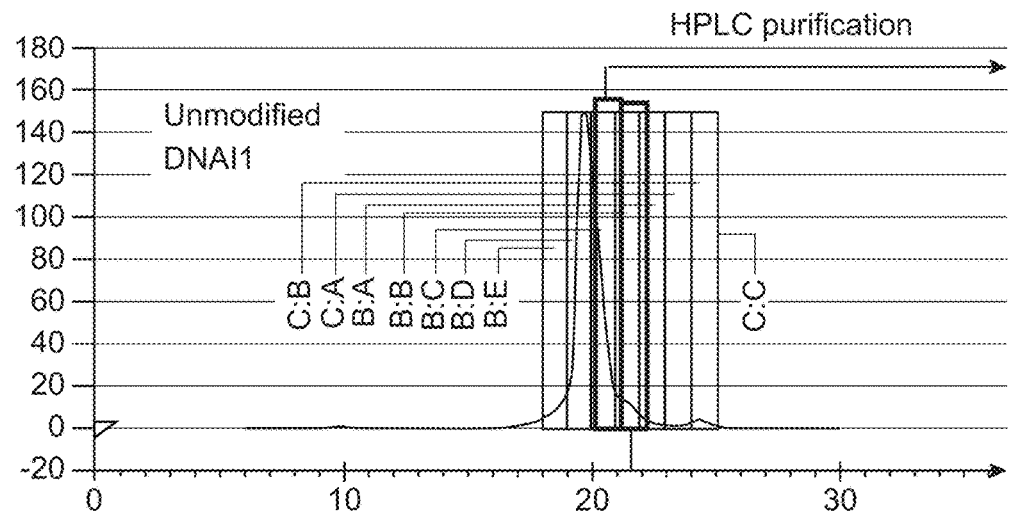
Figure 30B:
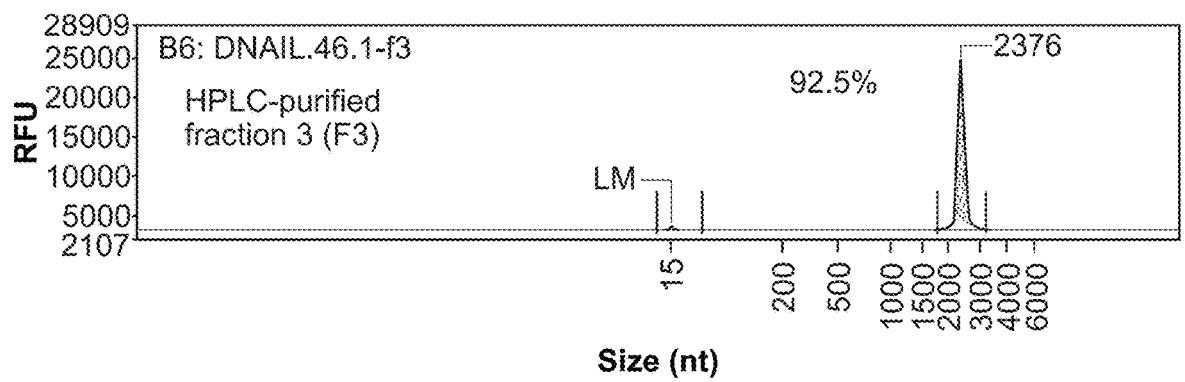
Figure 30B:
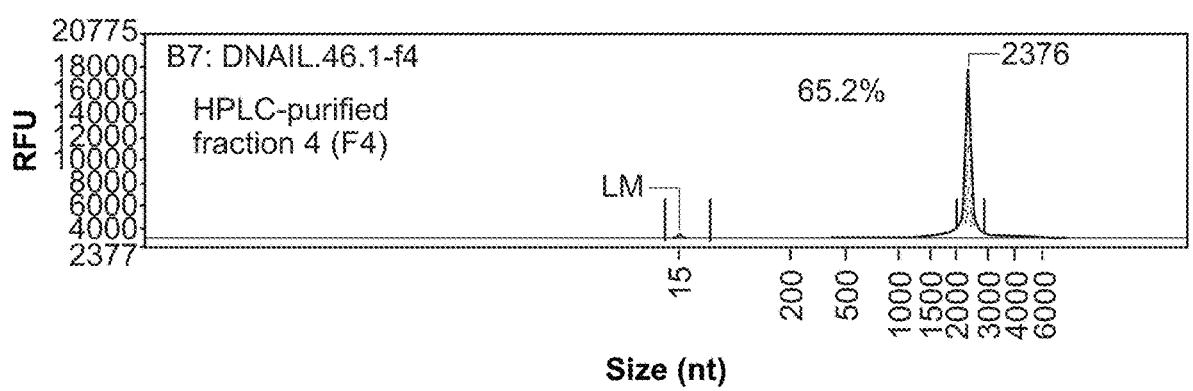

Altered reactivity with J2 antibody sensing double-stranded RNA content was observed as shown in FIG. 28. Based on comparison with known concentrations of poly-IC, the dsRNA content of DNAI1-coding mRNA featuring the CO++ORF averaged 39 ng while RNAs with a CO ORF were estimated to contain 68 ng of dsRNA contaminants when 200 ng of in vitro transcribed mRNA were dotted.

Example 11: HPLC-Purification of Unmodified and 100% m¹Ψ-Containing DNAI1 mRNA

Reverse phase high-performance liquid chromatography (HPLC) of DNAI1 mRNA was employed to purify full-length RNA and remove contaminants such as long dsRNA generated during the in vitro transcription using T7 RNA polymerase. Fractionation and purification results obtained using a non-porous RNASep C18 semi prep (100 mm×21.2 mm, column volume (CV) ca. 2.4 mL) column together with mobile phases containing triethylammonium acetate (TEAA) as an ion-pairing agent and increasing Acetonitrile content are shown in FIGS. 29A-29D. Judged by fragment analyzer evaluation of purified fractions, an overall quality improvement and full-length RNA enrichment using semi-prep RNASep column was observed. This quality improvement was achieved for both, unmodified (A, B) and 100% m¹Ψ-containing DNAI1 mRNA species (C, D).

As shown in FIGS. 30A-30E, a moderate improvement of translation activity was observed for fractions enriched in full-length, unmodified mRNA transcripts in A549 cells (A and B). Here, 1×10⁶ A549 cells per well were plated 18 hours before transfection in 6-well plates. Cells were transfected with about 100 ng of each RNA using MessengerMax transfection reagent at a RNA:MessengerMax ratio of 1:12 and harvested 6 h post transfection. Western blotting using a 1:2000 rabbit-anti-DNAI1 (AbCam ab166912, rabbit monoclonal to recombinant DNAI1 fragmentanti-DNAI1) antibody revealed DNAI1 protein expression as a 699 amino acid, 79.3 kDa protein (C). Relative translation efficiencies are indicated as the mean±standard deviation of three biological (transfection) replicates.

Importantly, HPLC readily removes late-eluting dot-blot reactive species at semi-prep scale. Detectable double-stranded RNA content reacting with J2 antibody was observed exclusively within the late-eluting fraction F7 and the unpurified control transcript while undetectable in all other HPLC-purified DNAI1 mRNA fractions F1 through F6 (D). The immunogenicity of unmodified, HPLC-purified transcripts was further tested in A549 cells by monitoring production of IL-6 in response to the transfected mRNA. Each cell line was transfected in triplicate with a titration of each RNA. Briefly, 20,000 cells per well were plated 18 hours prior to transfection in 96 well plates. The cells were then transfected with a titration of each transcript, from 250 ng to 7 ng per well, using MessengerMax reagent at a RNA:MessengerMax ration of 1:1.5. A reduction of IL-6 response was observed for the HPLC-purified fraction F3 producing the highest relative DNAI1 protein level (unpurified reference DNAI1 mRNA: (727+/−109 pg/mL)>F3 (73+/−30 pg/mL) for cells transfected with 125 ng RNA) (E).

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

---

What is claimed is:

1. A composition comprising a nucleic acid construct encoding a polypeptide at least 95% identical to a coiled-coil domain containing 39 (CCDC39) polypeptide, wherein said composition is formulated for administration to lung cells of a subject, wherein said composition comprises
   a cationic lipid;
   a fusogenic lipid;
   a cholesterol; and
   a polyethylene glycol (PEG) lipid;
   and wherein said nucleic acid construct comprises 1-methylpseudouridine.

2. The composition of claim 1, wherein said nucleic acid construct comprises codons that provide for heterologous expression of said polypeptide.

3. The composition of claim 1, further comprising a second nucleic acid encoding a second polypeptide, wherein said second polypeptide is at least 95% identical to a coiled-coil domain containing 40 (CCDC40) polypeptide.

4. The composition of claim 1, wherein said nucleic acid construct further encodes a second polypeptide, wherein said second polypeptide is at least about 95% identical to a CCDC40 polypeptide.

5. The composition of claim 1, wherein said polypeptide is identical to said CCDC39 polypeptide.

6. The composition of claim 1, wherein said nucleic acid construct is a ribonucleic acid (RNA).

7. The composition of claim 6, wherein said RNA is a messenger RNA (mRNA).

8. The composition of claim 6, wherein substantially all uridine residues in said nucleic acid construct are replaced with nucleotide analogues.

9. The composition of claim 8, wherein said nucleotide analogues comprise 1-methylpseudouridine.

10. The composition of claim 1, wherein said composition is formulated in a nanoparticle or a nanocapsule.

11. The composition of claim 1, wherein said nucleic acid construct further comprises a 3' or 5' noncoding region, wherein said 3' or 5' noncoding region enhances expression of said nucleic acid construct within a lung cell of said subject.

12. The composition of claim 11, wherein said nucleic acid construct further comprises a 5' cap structure.

13. The composition of claim 11, wherein said 3' noncoding region comprises a polyadenosine (poly(A)) tail.

14. The composition of claim 13, wherein said poly(A) tail enhances a half-life of said nucleic acid construct.

15. The composition of claim 13, wherein a length of said poly(A) tail is at most 200 adenosines.

16. The composition of claim 1, wherein fewer than 12.5% of all nucleotides within said nucleic acid construct are nucleotide analogues.

17. The composition of claim 1, wherein fewer than 10% of all nucleotides within said nucleic acid construct are nucleotide analogues.

18. A vector comprising a sequence that encodes said nucleic acid construct of claim 1.

19. An isolated nucleic acid comprising said vector of claim 18 and a heterologous sequence.

20. The composition of claim 1, wherein fewer than 15% of all nucleotides in said nucleic acid construct are nucleotide analogues.

* * * * *

SEQUENCE LISTING

```
Sequence total quantity: 20
SEQ ID NO: 1           moltype = DNA  length = 72
FEATURE                Location/Qualifiers
misc_feature           1..72
                       note = Description of Artificial Sequence: Synthetic
                       oligonucleotide
source                 1..72
                       mol_type = other DNA
                       organism = synthetic construct
SEQUENCE: 1
gggagacata aaccctggcg cgctcgcggc ccggcactct tctggtcccc acagactcag    60
agagaagcca cc                                                        72

SEQ ID NO: 2           moltype = DNA  length = 72
FEATURE                Location/Qualifiers
misc_feature           1..72
                       note = Description of Artificial Sequence: Synthetic
                       oligonucleotide
source                 1..72
                       mol_type = other DNA
                       organism = synthetic construct
SEQUENCE: 2
```

```
gggagacata aaccctggcg cgctcgcggg ccggcactct tctggtcccc acagactcag    60
agagaagcca cc                                                        72

SEQ ID NO: 3            moltype = DNA   length = 43
FEATURE                 Location/Qualifiers
misc_feature            1..43
                        note = Description of Artificial Sequence: Synthetic
                         oligonucleotide
source                  1..43
                        mol_type = other DNA
                        organism = synthetic construct
SEQUENCE: 3
gggagactct tctggtcccc acagactcag agagaacgcc acc                      43

SEQ ID NO: 4            moltype = DNA   length = 511
FEATURE                 Location/Qualifiers
misc_feature            1..511
                        note = Description of Artificial Sequence: Synthetic
                         polynucleotide
source                  1..511
                        mol_type = other DNA
                        organism = synthetic construct
SEQUENCE: 4
gttattttcc accatattgc cgtcttttgg caatgtgagg gcccggaaac ctggccctgt    60
cttcttgacg agcattccta ggggtctttc cctctcgcc aaaggaatgc aaggtctgtt    120
gaatgtcgtg aaggaagcag ttcctctgga agcttcttga agacaaacaa cgtctgtagc   180
gaccctttgc aggcagcgga accccccacc tggcgacagg tgcctctgcg gccaaaagcc   240
acgtgtataa gatacacctg caaaggcggc acaaccccag tgccacgttg tgagttggat   300
agttgtggaa agagtcaaat ggctctcctc aagcgtattc aacaaggggc tgaaggatgc   360
ccagaaggta cccattgta tgggatctga tctgggggcct cggtgcacat gctttacgtg   420
tgtttagtcg aggttaaaaa acgtactaggc cccccgaacc acggggacgt ggttttcctt   480
tgaaaaacac gatgataata tggccacaac c                                  511

SEQ ID NO: 5            moltype = DNA   length = 143
FEATURE                 Location/Qualifiers
misc_feature            1..143
                        note = Description of Artificial Sequence: Synthetic
                         polynucleotide
source                  1..143
                        mol_type = other DNA
                        organism = synthetic construct
SEQUENCE: 5
aaataacaaa tctcaacaca acatatacaa aacaaacgaa tctcaagcaa tcaagcattc    60
tacttctatt gcagcaattt aaatcatttc ttttaaagca aaagcaattt tctgaaaatt    120
ttcaccattt acgaacgata gca                                           143

SEQ ID NO: 6            moltype = DNA   length = 47
FEATURE                 Location/Qualifiers
misc_feature            1..47
                        note = Description of Artificial Sequence: Synthetic
                         oligonucleotide
source                  1..47
                        mol_type = other DNA
                        organism = synthetic construct
SEQUENCE: 6
gggagacaag agagaaaaga agagcaagaa gaaatataag agccacc                  47

SEQ ID NO: 7            moltype = DNA   length = 66
FEATURE                 Location/Qualifiers
misc_feature            1..66
                        note = Description of Artificial Sequence: Synthetic
                         oligonucleotide
source                  1..66
                        mol_type = other DNA
                        organism = synthetic construct
SEQUENCE: 7
gggagaccca agctggctag cgtttaaact taagcttggc aatccggtac tgttggtaaa    60
gccacc                                                               66

SEQ ID NO: 8            moltype = DNA   length = 291
FEATURE                 Location/Qualifiers
misc_feature            1..291
                        note = Description of Artificial Sequence: Synthetic
                         polynucleotide
source                  1..291
                        mol_type = other DNA
                        organism = synthetic construct
SEQUENCE: 8
gggagaccca agctggctag cgtttaaact taagctttcc tttccgggcc ggctgggcgc    60
```

```
gccgaagcgc ctgcgccttg gctgctggtc ggttgctggg taaccgcgtc agggagttgg    120
attctatcct gcaagggcac ggggacccac aacgacggct gtccctaaag aaccgttgcg    180
actggtaact gaagtggaag agagtccaga tttcttgtgt gtggtcaagg agacggacaa    240
acttttgtc ttcagacgag ggagcgtttt gtaggctctc caggggttga g              291

SEQ ID NO: 9              moltype = DNA   length = 186
FEATURE                   Location/Qualifiers
misc_feature              1..186
                          note = Description of Artificial Sequence: Synthetic
                           polynucleotide
source                    1..186
                          mol_type = other DNA
                          organism = synthetic construct
SEQUENCE: 9
ggattgtgtc cgtaatcaca cgtggtgcgt acgataacgc atagtgtttt tccctccact    60
taaatcgaag ggttgtgtct tggatcgcgc gggtcaaatg tatatggttc atatacatcc   120
gcaggcacgt aataaagcga ggggttcgaa tcccccgtt accccggta ggggcccatt     180
gtcttc                                                              186

SEQ ID NO: 10             moltype = DNA   length = 114
FEATURE                   Location/Qualifiers
misc_feature              1..114
                          note = Description of Artificial Sequence: Synthetic
                           polynucleotide
source                    1..114
                          mol_type = other DNA
                          organism = synthetic construct
SEQUENCE: 10
tcagtagggt catgaaggtt tttcttttcc tgagaaaaca acacgtattg ttttctcagg    60
ttttgctttt tggcctttt ctagcttaaa aaaaaaaaa gcaaaattgt cttc           114

SEQ ID NO: 11             moltype = DNA   length = 112
FEATURE                   Location/Qualifiers
misc_feature              1..112
                          note = Description of Artificial Sequence: Synthetic
                           polynucleotide
source                    1..112
                          mol_type = other DNA
                          organism = synthetic construct
SEQUENCE: 11
tcagtagggt tgtaaaggtt tttcttttcc tgagaaaaca accttttgtt ttctcaggtt    60
ttgcttttg gcctttccct agctttaaaa aaaaaaagc aaaattgtct tc             112

SEQ ID NO: 12             moltype = DNA   length = 68
FEATURE                   Location/Qualifiers
misc_feature              1..68
                          note = Description of Artificial Sequence: Synthetic
                           oligonucleotide
source                    1..68
                          mol_type = other DNA
                          organism = synthetic construct
SEQUENCE: 12
gaagtggcgg ttcggccgga ggttccatcg tatccaaaag gctcttttca gagccaccca    60
ttgtcttc                                                            68

SEQ ID NO: 13             moltype = DNA   length = 239
FEATURE                   Location/Qualifiers
misc_feature              1..239
                          note = Description of Artificial Sequence: Synthetic
                           polynucleotide
source                    1..239
                          mol_type = other DNA
                          organism = synthetic construct
SEQUENCE: 13
ggggctggcc tcagtctctg tcccatcgct tgaatacagt actcctaggg cttgaccctg    60
gtacccagcc cagccttagc acccagcatg tgacccact cctgatcagg tcccagcatc   120
ttcccttctt gttctgttcc ttaaggtccc agcaccttac cccaggactt ggtcttaac    180
caccattacc cctctaactt tgcacaaata aacctgtgta gaaacccacc ccaaaaaaa    239

SEQ ID NO: 14             moltype = DNA   length = 2100
FEATURE                   Location/Qualifiers
misc_feature              1..2100
                          note = Description of Artificial Sequence: Synthetic
                           polynucleotide
source                    1..2100
                          mol_type = other DNA
                          organism = synthetic construct
SEQUENCE: 14
atgatcccag caagcgccaa ggcaccacac aagcagcccc acaagcagag catctccatc    60
```

```
ggcagggca   caaggaagag   ggacgaggat   agcggaaccg   aagtgggaga   gggaacagac    120
gagtgggcac  agtccaaggc   aaccgtgcgc   ccacctgacc   agctggagct   gacagatgcc    180
gagctgaagg  aggagttcac   caggatcctg   acagccaaca   atccacacgc   ccccagaac     240
atcgtgcgct  actcttcaa    ggagggcaca   tataagccaa   tcggctttgt   gaaccagctg    300
gccgtgcact  atacccaagt   gggcaatctg   atccccaagg   actccgatga   gggccggaga    360
cagcactaca  gggacgagct   ggtggcagga   tcccaggagt   ctgtgaaagt   gatctctgag    420
accggcaatc  tggaggagga   cgaggagcca   aaggagctgg   agaccgagcc   aggaagccag    480
acagatgtgc  ctgcagcagg   agcagcagag   aaggtgaccg   aggaggagct   gatgacacct    540
aagcagccaa  aggagcggaa   gctgaccaac   cagttcaatt   tttccgagag   agcctctcag    600
acatacaaca  atccagtgcg   ggacagagag   tgccagaccg   agccaccccc   tagaaccaac    660
ttttccgcca  cagccaatca   gtgggagatc   tacgatgcct   atgtggagga   gctggagaag    720
caggagaaga  ccaaggagaa   ggagaaggcc   aagacacccg   tggccaagaa   gtccggcaag    780
atggccatgc  ggaagctgac   cagcatggag   tcccagacag   acgatctgat   caagctgtct    840
caggccgcca  agatcatgga   gagaatggtg   aaccagaata   cctatgacga   tatcgcccag    900
gacttcaagt  actatgacga   tgcagcagac   gagtacaggg   atcaagtggg   cacactgctg    960
cctctgtgga  agtttcagaa   cgataaggcc   aagaggctga   gcgtgaccgc   cctgtgctgg    1020
aatccaaagt  acagggaacct  gttcgcagtg   ggatacggat   cttatgactt   catgaagcag    1080
agcagaggca  tgctgctgct   gtattccctg   aagaacccct   ctttccctga   gtacatgttt    1140
agctccaatt  ccggcgtgat   gtgcctggac   atccacgtgg   atcacccca    cctggtggcc    1200
gtgggccact  atgacggcaa   cgtggccatc   tacaatctga   agaagcctca   ctctcagccc    1260
agcttctgtt  ctagcgccaa   gagcggcaag   cactccgatc   ccgtgtggca   ggtgaagtgg    1320
cagaaggacg  atatgaccaa   gaacctgaat   ttcttttccg   tgtcctctga   tggcaggatc    1380
gtgtcttgga  ccctggtgaa   gcgcaagctg   gtgcacatcg   acgtgatcaa   gctgaaggtg    1440
gagggcagca  ccacagaggt   gccagaggga   ctgcagctgc   accagtggga   tgcggcaca    1500
gccttcgact  tcacaaagga   gatcgatat   atgttcctgg   tgggcaccga   ggagggcaag    1560
atctacaagt  gttctaagag   ctatagctcc   cagtttctgg   acacatatga   tgcccacaac    1620
atgagcgtgg  ataccgtgtc   ctggaatcct   taccacacaa   aggtgttcat   gagctgctct    1680
agcgactgga  ccgtgaagat   ctgggatcac   accatcaaga   cacctatgtt   tatctatgac    1740
ctgaactccg  ccgtgggcga   tgtggcatgg   gcaccatact   cctctacagt   gttcgcagca    1800
gtgaccacag  acggcaaggc   acacatcttt   gatctggcca   tcaacaagta   cgaggccatc    1860
tgtaatcagc  ccgtggccgc   caagaagaac   aggctgaccc   acgtgcagtt   caatctgatc    1920
caccctatca  tcatcgtggg   cgacgatcgg   ggccacatca   tctctctgaa   gctgagcccc    1980
aacctgagaa  agatgcctaa   ggagaagaag   ggacaggagg   tgcagaaggg   accagcagtg    2040
gagatcgcaa  agctggacaa   gctgctgaat   ctggtgcgcg   aggtgaagat   caagacctga    2100

SEQ ID NO: 15             moltype = DNA   length = 2100
FEATURE                   Location/Qualifiers
misc_feature              1..2100
                          note = Description of Artificial Sequence: Synthetic
                          polynucleotide
source                    1..2100
                          mol_type = other DNA
                          organism = synthetic construct
SEQUENCE: 15
atgatcccag  caagcgccaa   ggcaccacac   aagcagcccc   acaagcagag   catcagcatc    60
ggcagggca   caaggaagag   ggacgaggac   agcggaaccg   aagtgggaga   gggaacagac    120
gagtgggcac  agagcaaggc   aaccgtgcgc   ccacccgacc   agctggagct   gacagacgcc    180
gagctgaagg  aggagttcac   caggatcctg   acagccaaca   acccacacgc   ccccagaac     240
atcgtgcgct  acagcttcaa   ggagggcaca   tacaagccaa   tcggcttcgt   gaaccagctg    300
gccgtgcact  acacccaagt   gggcaacctg   atccccaagg   acagcgacga   gggccggaga    360
cagcactaca  gggacgagct   ggtggcagga   agccaggaga   gcgtgaaagt   gatcagcgag    420
accggcaacc  tggaggagga   cgaggagcca   aaggagctgg   agaccgagcc   aggaagccag    480
acagacgtgc  ccgcagcagg   agcagcagag   aaggtgaccg   aggaggagct   gatgacaccc    540
aagcagccaa  aggagcggaa   gctgaccaac   cagttcaact   tcagcgagag   agccagccag    600
acatacaaca  acccagtgcg   ggacagagag   tgccagaccg   agccacccc    cagaaccaac    660
ttcagcgcca  cagccaacca   gtgggagatc   tacgacgcct   acgtggagga   gctggagaag    720
caggagaaga  ccaaggagaa   ggagaaggcc   aagacacccg   tggccaagaa   gagcggcaag    780
atggccatgc  ggaagctgac   cagcatggag   agccagacag   acgacctgat   caagctgagc    840
caggccgcca  agatcatgga   gagaatggtg   aaccagaaca   cctacgacga   catcgcccag    900
gacttcaagt  actacgacga   cgcagcagac   gagtacaggg   accaagtggg   cacactgctg    960
cccctgtgga  agttccagaa   cgacaaggcc   aagaggctga   gcgtgaccgc   cctgtgctgg    1020
aacccaaagt  acagggaacct  gttcgcagtg   ggatacggaa   gctacgactt   catgaagcag    1080
agcagaggca  tgctgctgct   gtacagcctg   aagaacccca   gcttcccga    gtacatgttc    1140
agcagcaaca  gcggcgtgat   gtgcctggac   atccacgtgg   accacccta    cctggtggcc    1200
gtgggccact  acgacggcaa   cgtggccatc   tacaacctga   agaagccca   cagcagccc     1260
agcttctgca  gcagcgccaa   gagcggcaag   cacagcgacc   ccgtgtggca   ggtgaagtgg    1320
cagaaggacg  acatgaccaa   gaacctgaac   ttcttcagcg   tgagcagcga   cggcaggatc    1380
gtgagctgga  ccctggtgaa   gcgcaagctg   gtgcacatcg   acgtgatcaa   gctgaaggtg    1440
gagggcagca  ccacagaggt   gccagaggga   ctgcagctgc   accagtggga   tgcggcaca    1500
gccttcgact  tcacaaagga   gatcgactac   atgttcctgg   tgggcaccga   ggagggcaag    1560
atctacaagt  gcagcaagag   ctacagcagc   cagttcctgg   acacatacga   cgcccacaac    1620
atgagcgtgg  acaccgtgag   ctggaacccc   taccacacaa   aggtgttcat   gagctgcagc    1680
agcgactgga  ccgtgaagat   ctgggaccac   accatcaaga   cacccatgtt   catctacgac    1740
ctgaactccg  ccgtgggga    cgtggcatgg   gcaccataca   gcagcacagt   gttcgcagca    1800
gtgaccacag  acggcaaggc   acacatcttc   gacctggcca   tcaacaagta   cgaggccatc    1860
tgcaaccagc  ccgtggccgc   caagaagaac   aggctgaccc   acgtgcagtt   caacctgatc    1920
caccccatca  tcatcgtggg   cgacgaccgg   ggccacatca   tcagcctgaa   gctgagcccc    1980
aacctgagaa  agatgcccaa   ggagaagaag   ggacaggagg   tgcagaaggg   accagcagtg    2040
gagatcgcaa  agctggacaa   gctgctgaac   ctggtgcgcg   aggtgaagat   caagacctga    2100
```

```
SEQ ID NO: 16          moltype = DNA  length = 2100
FEATURE                Location/Qualifiers
misc_feature           1..2100
                       note = Description of Artificial Sequence: Synthetic
                       polynucleotide
source                 1..2100
                       mol_type = other DNA
                       organism = synthetic construct
SEQUENCE: 16
atgatcccag caagcgccaa ggcaccacac aagcagcccc acaagcagag catctccatc    60
ggcaggggca caaggaagag ggacgaggac agcggaaccg aagtgggaga gggaacagac   120
gagtgggcac agtccaaggc aaccgtgcgc ccacctgacc agctggagct gacagatgcc   180
gagctgaagg aggagttcac caggatcctg acagccaaca atccacacgc ccccagaac   240
atcgtgcgct acagcttcaa ggagggcaca tacaagccaa tcggcttcgt gaaccagctg   300
gccgtgcact acacccaagt gggcaatctg atccccaagg actccgatga gggccggaga   360
cagcactaca gggacgagct ggtggcagga tcccaggagt ctgtgaaagt gatctctgag   420
accggcaatc tggaggagga cgaggagcca aaggagctgg agaccgagac aggaagccag   480
acagatgtgc ctgcagcagg agcagcagag aaggtgaccg aggaggagct gatgacaccc   540
aagcagccaa aggagcggaa gctgaccaac cagttcaact tctccgagag agcctctcag   600
acatacaaca atccagtgcg ggacagagag tgccagaccg agccaccccc agaaccaac   660
ttctccgcca cagccaatca gtgggagatc tacgatgcct acgtggagga gctggagag   720
caggagaaga ccaaggagaa ggagaaggcc aagacacccg tggccaagaa gtccggcaag   780
atggccatgc ggaagctgac cagcatggag tcccagacag acgatctgat caagctgtct   840
caggccgcca agatcatgga gaatgtgta accagaaca cctacgacga catcgcccag   900
gacttcaagt actacgacga tgcagcagac gagtacagag atcaagtgca cactgctg   960
cctctgtgga agttccagaa cgacaaggcc aagaggctga gcgtgaccgc cctgtgctga  1020
aatccaaagt cagggaccct gttcgcagtg ggatacggaa gctacgactt catgaagcag  1080
agcagaggca tgctgctgct gtactccctg aagaacccca gcttccctga gtacatgttc  1140
agctccaact ccggcgtgat gtgcctggac atccacgtgg atcaccccta cctggtggcc  1200
gtgggccact acgacggcaa cgtggccatc acaatctga agaagcctca ctctcagccc  1260
agcttctgca gcagcgccaa gagcggcaag cactccgatc ccgtgtggca ggtgaagtgg  1320
cagaaggacg acatggacca gaacctgaac ttcttctccg tgtcctctga tggcaggatc  1380
gtgagctgga cctggtgaa gcgcaagctg gtgcacatcg acgtgatcaa gctgaaggtg  1440
gagggcagca ccacagaggt gccagaggga ctgcagctgc acccagtggg atgcggcaca  1500
gccttcgact ccacaagga gatcgactac atgttcctgg tgggcaccga ggagggcaag  1560
atctacaagt gcagcaagag ctacagctcc cagttcctgg acacatacga tgcccacaac  1620
atgagcgtgg acaccgtgtc ctggaatccc taccacacaa aggtgttcat gagctgcagc  1680
agcgactgga ccgtgaagat ctgggatcac accatcaaga cacccatgtt catctacgac  1740
ctgaactccg ccgtgggcga tgtggcatgg gcaccatact ccagcacagt gttcgcagca  1800
gtgaccacag acggcaaggc acacatcttc gatctggcca tcaacaagta cgaggccatc  1860
tgcaatcagc ccgtggccgc caagaagaac aggctgaccc acgtgcagtt caatctgatc  1920
caccccatca tcatcgtggg cgacgatcgg ggccacatca tctctctgga gctgagcccc  1980
aacctgagaa agatgcccaa ggagaagaag ggacaggagg tgcagaaggg accagcagtg  2040
gagatcgcaa agctggacaa gctgctgaat ctggtgcgcg aggtgaagat caagacctga  2100

SEQ ID NO: 17          moltype = DNA  length = 13875
FEATURE                Location/Qualifiers
misc_feature           1..13875
                       note = Description of Artificial Sequence: Synthetic
                       polynucleotide
source                 1..13875
                       mol_type = other DNA
                       organism = synthetic construct
SEQUENCE: 17
atgttcagaa tcggcagacg gcagctgtgg aagcacagcg tgaccagagt gctgacccag    60
cggctgaagg gcgagaaaga ggccaagaga gccctgctgg acgcccggca caactacctg   120
ttcgccatcg tggccagctg cctgaccctg aacaagaccg aggtggaaga cgccatcctg   180
gaaggcaacc agatcgagcg gatcgaccag ctgttcgccg tgggcggact gcgcaccctg   240
atgttctact accaagacgt ggaagaggcc gagacggcc agctgggcga gctgggcgga   300
gtgaacctgg tgagcggcaa gatcaagaaa cccaaggtgt cgtgaccga gggcaacgac   360
gtggccctga caggcgtgtg cgtgttcttc atcagaaccg accccagcaa ggccatcacc   420
cccgacaaca tccaccagga agtgagcttc aacatgctgg acgccgccga cggcggcctg   480
ctgaacagcg tgcggagact gctgagcgac atcttcatcc ccgtgctgga agccacaagc   540
cacggctggg agagctggaa ggactgcag gacgccgcca acatccggca ggaattcctg   600
agcagcctgg aaggattcgt gaacgtgctg agcggcgccc aggaaagcct gaagaaaaa   660
gtgaacctgc ggaagtgcga catcctggaa ctgaaaaccc tgaaagagcc cacccactac   720
ctgaccctgg ccaacaaccc cgagacactg ggccaagatg aggactgcat gaaagtgtgg   780
atcaagcaga ccgaacctgg gctggccgag aacaaccagc tgctgaaaga agccgacgac   840
gtgggcccaa gagccgagct ggaacactgg aagaagcggc tgagcaagtt caactacctg   900
ctggaacagc tgaagagccc cgacgtgaag gccgtgctgg ccgtgctggc agccgccaag   960
agcaaactgc tgaaacctg gcgcgagatg gacatccgga tcaccgacgc caccaacgag  1020
gccaaggaca acgtgaagta cctgtacacc tggaaaagt gctgcgaccc cctgtacagc  1080
agcgactgcc tgagcatgat ggacgccatc cccgtggca tccacaagatgatc  1140
tacagcatca gccactacta caacaccagc gagaagatcc cagcctgtt cgtgaaagtg  1200
accaaccaga tcatcagcgc ctgcaaggcc tacatcacca caaacggcac cgcagcatc  1260
tggaaccagc cccaggacgt ggtggaagag aagatcctga cgccatcaa gctgaagcag  1320
gaataccagc tgtgcttcca caagaccaag cagaagctga acagaacccc aacgccaag  1380
cagttcgact tcagcgagat gtacatcttc ggcaagttcg acattcca ccggcggctg  1440
```

-continued

```
gccaagatca tcgacatctt caccaccctg aaaacataca gcgtgctgca ggacagcacc    1500
atcgagggcc tggaagacat ggccaccaag taccagggca tcgtggccac catcaagaag    1560
aaagagtaca acttcctgga ccagcgcaag atggacttcg accaggacta cgaggaattc    1620
tgcaagcaga caaacgacct gcacaacgag ctgcgcaagt tcatgacgt gaccttcgcc    1680
aagatccaga acaccaacca ggccctgcgg atgctgaaga agttcgagag actgaacatc    1740
cccaacctgg gcatcgacga caagtaccag ctgatcctgg aaaactacgg cgccgacatc    1800
gacatgatca gcaagctgta cacaaagcag aagtacgacc cccccctggc ccggaaccag    1860
cccccatcg ccggcaaaat cctgtgggcc agacagctgt tccaccggat ccagcagccc    1920
atgcagctgt tccagcagca cccgccgtg ctgagcacga ccgaggccaa acccatcatc    1980
cggagctaca accggatggc caaggtgctg ctggaattcg aggtgctgtt ccaccgggcc    2040
tggctgcggc agatcgaaga gatccacgtg ggactggaag ccagcctgct cgtgaaggcc    2100
cccgaaccg gcgagctgtt cgtgaacttc gacccccaga tcctgatcct gttccgggaa    2160
accgagtgca tggcccagat ggggctgaaa gtgagccccc tggccaccag cctgttccag    2220
aagcggaac ggtacaagcg gaacttcagc aacatgaaga tgatgctggc cgagtaccag    2280
cgcgtgaaga gcaagatccc cgccgccatc gagcagctga tcgtgcccca cctggccaaa    2340
gtggacgagg ccctgcagcc aggactggcc gccctgacat ggaccagcct gaacatcgag    2400
gcctacctgg aaaacacatt cgccaaaatc aaggacctgg aactgctgct ggaccgcgtg    2460
aacgacctga tcgagttccg gatcgacgcc atcctggaag atgagcag caccccctg    2520
tgccagctgc cccaggaaga acccctgacc tgcgaagagt tcctgcagat gaccaaggac    2580
ctgtgcgtga acgcgccca gatcctgcac ttcaagagca gcctggtgga agaagccgtg    2640
aacgagctcg tgaacatgct gctggacgtg aagtgctga gcgaggaaga gagcgagaag    2700
atcagcaacg agaacagcgt gaactacaag aacgagagca gcgccaagcg ggaagagggc    2760
aacttcgaca ccctgaccag cagcatcaac gccagagcca acgccctgct gctgaccacc    2820
gtgacccgga agaaaaaaga aaccgagatg ctgggcgaag aggccagaga gctgctgagc    2880
cacttcaacc accagaacat ggacgccctg ctgaaagtga cacggaacac cctggaagcc    2940
atccggaaca ggatccacag cagccacacc atcaacttcc gggacagcaa cagcgccgag    3000
aacatgaagc agaacagcct gcccatcttc cgggccagcg tgacactggc catccccaac    3060
atcgtgatgg ccccgccct ggaagacgtg cagcagacac tgaacaaggc cgtggaatgc    3120
atcatcagcc tgcccaaggg cgtgcggcag tggagcagcg aactgctgag caagaagaag    3180
atccaggaac ggaaaatggc cgccctgcca agcaacgagg acagccgacag cgacgtggaa    3240
atgggcgaga acgagctgca ggacacactg gaaatcgcca gcgtgaacct gcccatcccc    3300
gtgcagacca gaactacta caagaacgtg agcgaaaaca aagaaatcgt gaagctggtg    3360
agcgtgctga gcaccatcat caacagcacc aagaaagaag tgatcaccag catggactgc    3420
ttcaagcggt acaaccacat ctggcagaag ggcaaagaag aggccatcaa gaccttcatc    3480
acccagagcc ccctgctgag cgagttcgag agccagatcc tgtacttcca gaacctggaa    3540
caggaaatca acgccgagcc cgagtacgtg tgcgtgggca gcatcgccct gtacaccgcc    3600
gacctgaagt tcgccctgac cgccgagaca aaggccggaa tggtcgtgat cggccggcac    3660
tgcaacaaaa agtacagaag cgagatggaa aacatcttca tgctgatcga ggaattcaac    3720
aagaaactga accggcccat caaggacctg gacgacatca gaatcgccat ggccgcactg    3780
aaagagatca gagaggaaca gatcagcatc gacttccaag tgggcccat cgaggaaagc    3840
tacgccctgc tgaacagata cggactgctg atcgcccggg aagagatcga caaggtggac    3900
accctgcact acgcctggga agctgctg gccagagccg cgaggtgca gaacaaactg    3960
gtgagcctgc agcccagctt caagaaagaa cgtgatcagcg ccgtgaagt gttcctgcag    4020
gactgccacc agttctacct ggactacgac ctgaacggcc ccatggccag cggcctgaaa    4080
ccccaggaag ccagcgaccg gctgatcatg ttccagaacc agttcgacaa catctaccgg    4140
aagtacatca cctacacagg cggcgaggaa ctgttcggcc tgcccgccac acagtacccc    4200
cagctgctgg aaatcaagaa cagctgaac ctgctgcaga atcatccctgtacaac    4260
agcgtgatcg agacagtgaa cagctactac gacatcctgt ggagcgaagt gaacatcgag    4320
aagatcaaca cgaactgct ggaattccag aaccggtgcc ggaagctgcc cagagcactg    4380
aaggactggc aggccttcct ggacctgaag aaaatcatcg acgacttcag cgagtgctgc    4440
ccctgctgg agtacatggc cagcaaggcc atgatggaac ggcactggga gaatccan    4500
acactgaccg gccacagcct ggacgtgggc aacgagagct tcaagctgcg gaacatcatg    4560
gaagccccac tgctgaagta caagaggaa atcgaggaca tctgcatcag cgccgtgaaa    4620
gagcgggaca tcgagcagaa actgaaacaa gtgatcaacg agtgggacaa caagaccttc    4680
acctcggca gcttcaagac cagaggcgag ctgctgctgc ggggcgacag caccagcgag    4740
atcatcgcca acatggaaga cagcctgatg ctgctgggca gcctgctgag caacccggtac    4800
aacatgccct tcaaggccca gatccagaaa tgggtgcagt acctgagcaa cagcaccgac    4860
atcatcgaga gctggatgac cgtgcagaac ctgtggatct acctggaagc cgtgttcgtg    4920
ggcggcgaca tcgccaagca gctgcccaaa gaggccagc ggttcagcaa catcgacaag    4980
agctgggtca agatcatgac cagagcccac gaggtgccca cgtggtgca gtgctgcgtg    5040
ggcgacgaaa cactgggaca gctgctgccc cacctgctgg accagctgga aatctgccag    5100
aagagcctga ccggctacct ggaaaagaaa cggctgtgct ccccggtt cttcttcgtg    5160
agcgaccccg ccctgctgga aatcctgggc caggccagcg acagccacac aatccaggcc    5220
cacctgctga acgtgttcga caacatcaag aggcctgcct tccacgagaa aatctacgac    5280
cggatcctga gcatcagcag ccaggaaggc gagacaatcg agctgacaa gcccgtgatg    5340
gccgagggaa acgtggaagt gtggctgaac agcctgctgg aagagagcca gagcagcctg    5400
cacctcgtga tcagacaggc cgccgccaac atccaggaaa ccggcttcca gctgaccgag    5460
ttcctgagca gcttcccagc acaagtggga ctgctggca tccagatgat ctggaccgaga    5520
gacagcgaag aggcctgag aaacgccaag ttcgacaaga aaatcatgca gaaaacaaac    5580
caggcattcc tggaactgct gaacaccctg atcgacgtga ccaccgggaa cctgagcagc    5640
accgagagag tgaagtacga cactgatc accatccacg tgcaccagcg ggacatcttc    5700
gacgacctgt gccacatgca catcaagagc cccatggact cgagtggct gaagcagtgc    5760
aggttctact caacgagga cagcgacaag atgatgatcc acatccaccga cgtggccttc    5820
atctaccaga tcaacagttcct ggctgtacc cctgaccgag tgatcaccc cctgaccgac    5880
cggtgctaca tcacactggc ccaggcactg gcatgagca tgggaggcgc accaccagga    5940
cccgccggca caggcaagac cgaaaccacc aaggacatgg gacgctgcct gggcaaatac    6000
gtggtggtgt caactgcag cgaccagatg gacttccggg gcctgggccg gatcttcaag    6060
ggcctggcac agagcggaag ctggggctgc ttcgacgagt tcaacagaat cgacctgccc    6120
gtgctgagcg tggccgcaca gcagatcagc atcatcctga catgcaaaaa agagcacaag    6180
```

```
aagagcttca tcttcaccga cggcgacaac gtgaccatga accccgagtt cggcctgttc    6240
ctgacaatga accccggcta cgccggacgg caggaactgc ccgagaacct gaagatcaac    6300
ttccggagcg tggccatgat ggtgcccgac cggcagatca tcatcagagt gaaactggcc    6360
agctgcggct tcatcgacaa cgtggtgctg gcccggaagt tcttcacact gtacaagctg    6420
tgcgaagaac agctgagcaa acaggtgcac tacgacttcg gcctgaggaa catcctgagc    6480
gtgctgagaa ccctgggagc cgccaagcgg gccaacccca tggacaccga gagcacaatc    6540
gtgatgcggg tgctgcggga catgaacctg agcaagctga tcgacgagga cgagcccctg    6600
ttcctgagcc tgatcgagga cctgttcccc aacatcctgc tggacaaggc cggctacccc    6660
gaactggaag ccgccatcag cagacaggtg aagaggccgg gcctgatcaa ccaccccctg    6720
tggaaactga aagtgatcca gctgttcgag acacagcgcg tgcggcacgg catgatgaca    6780
ctgggaccca gcggagccgg caagaccacc tgcatccaca cactgatgcg ggccatgacc    6840
gactgcggca agccccaccg cgagatgcgg atgaacccca aggccatcac cgcccccag    6900
atgttcggca gactggacgt ggccaccaac gactggaccg acggcatctt cagcaccctg    6960
tggcgcaaga ccctgcgggc caagaagggc gagcacatct ggatcatcct ggacggcccc    7020
gtggacgcca tctggatcga gaacctgaac agcgtgctgg acgacaacaa gacactgacc    7080
ctggccaacg cgaccggat ccccatggcc cccaactgca agatcatctt cgagcccac    7140
aacatcgaca acgccagccc cgccaccgtg agcagaaacg gcatggtgtt catgagcagc    7200
agcatcctgg actggagccc catcctgaa ggcttcctga agaagcggaa ccccaggaa    7260
gccgagatcc tgagacagct gtacaccgag agcttccccg acctgtaccg gttctgcatc    7320
cagaacctgg agtacaagat ggaagtgctg gaagccttcg tgatcaccca gagcatcaac    7380
atgctgcagg gcctgatccc cctgaaagaa cagggcggag aagtgagcca ggcccacctg    7440
ggcagactgt tcgtgttcgc cctgctgtgg agcgccgggc ccgccctga actggacgga    7500
aggcggagac tggaactgtg gctgcggagc agaccaccg gcaccctgga actgcccca    7560
ccagccggac ccggcgacac cgccttcgac tactacgtgg cccccgacgg cacctggacc    7620
cactggaaca cccggaccca ggaatacctg taccccagcg cacaccaccc cgagtacggc    7680
agcatcctgg tgcccaacgt ggacaacgtg cggaccgact tcctgatcca gacaatgcc    7740
aagcagggaa aggccgtgct gctgatcgg gagcagggca cagccaagac cgtgatcatc    7800
aagggcttca tgagcaagta cgaccccgag tgccacatga tcaagagcct gaacttcagc    7860
agcgccacca ccccactgat gttccagcgg accatcgaga gctacgtgga caagcggatg    7920
ggcaccacct acggccccc agccggcaag aaaatgactg tgttcatcga cgacgtgaac    7980
atgcccatca tcaacgagtg gggcgaccaa gtgaccaacg agatcgtgcg gcagctgatg    8040
gaacagaacg gcttctacaa cctggaaaag cccggcgagt tcaccagcat cgtggacatc    8100
cagttcctgg ccgccatgat ccaccccggc ggcggaagaa cgacatccc cagcggctg    8160
aagcggcagt tcagcatctt caactgcacc ctgcccagcg aggccagcgt ggacaagatc    8220
ttcggcgtga tcggcgtggg ccactactgc acccagaaga gcttcagcga gaagtgcgg    8280
gacagcgtga ccaagctggt gcccctgaca agacggctgt ggcagatgac caagatcaag    8340
atgctgccca ccccgccaa gttccactac gtgttcaacc tgcggacct gagcagagtg    8400
tggcagggaa tgctgaacac caccagcgaa gtgatcaaag agccaacga cctgctgaag    8460
ctgtgcgaag cgagtgcaa gagagtgatc gccgaccggt tcaccgtgag cagcgacgtg    8520
acatggttcg acaagcct ggtgagcctg gtggaagagg aattcggcga agagaagaa    8580
ctgctggtgg actgcggcat cgacacctac ttcgtggact tcctgcgcga cgcccccgaa    8640
gccgccggcg agacaagcga agaggccgac gccgagacac ccaagatcta cgagcccatc    8700
gagagcttca gccacctgaa agaaaggctg aacatgttcc tgcagctgta caacgagagc    8760
atccggggag ccggcatgga catggtgttc ttcgccgacg ccatggtgca cctcgtgaag    8820
atcagcagag tgatccggac cccccagggc aacgccctgc tcgtgggagt gggaggcagc    8880
ggcaagcaga gcctgaccag actggccagc ttcatcgccg gctacgtgag cttccagatc    8940
accctgaccc ggagctacaa caccagcaac ctgatggaag acctgaaggt gctgtaccgg    9000
acagccggcc agcagggaa gggcatcacc ttcatcttca ccgacaacga gatcaaggac    9060
gagagcttcc tggagtacat gaacaacgtg ctgagcagcg cgaggtgag caacctgttc    9120
gcccgggacg agatcgacga gatcaacagc gacctggcca gcgtgatgaa gaaagaattc    9180
ccccgtgcc tgcccacaaa cgagaacctg cacgactact tcatgagcag agtgcggcag    9240
aacctgcaca tcgtgctgtg cttcagcccc gtgggcgaga agttcagaaa ccggccctg    9300
aagttccccg ccctgatcag cggctgcacc atcgactggt tcagccggtg gcccaaggac    9360
gccctggtgg ccgtgagcga gcacttcctg accagctacg acatcgactg cagcctggaa    9420
atcaagaaag aggtggtgca gtgcatgagc agcttccagg acggcgtggc cgagaaatgc    9480
gtggactact tccagcggtt ccggcggagc acccacgtga cccccaagag ctacctgagc    9540
ttcatccagg gctacaagtt catctacggc gagaagcacg tggaagtgcg cacactggcc    9600
aaccggatga caccggcct ggaaaaactg aagaggcca cgagagcgt ggccgccctg    9660
agcaaagaac tggaagtgaa agaaaaagaa ctgcaggtgg ccaacgacaa ggccgacatg    9720
gtgctgaaag aagtgaccat gaaggcccag gccgccgaga aagtgaaagc cgaggtgcag    9780
aaagtgaagg accgggccca ggccatcgtg acagcatca gcaaggacaa ggccatcgcc    9840
gaggaaaagc tggaagcagc caagcccgcc ctggaagagg cagaagccgc cctgcagacc    9900
atccggccca gcgacatcgc cacagtgcgg accctggaa ggcccccca cctgatcatg    9960
cggatcatgg actgcgtgct gctgctgttc cagagaaagg tggcgcgt gaagatcgac   10020
ctggaaaaaa gctgcaccat gcccagctgg caggaaagcc tgaagctgat gaccgccggc   10080
aacttcctgc agaacctgca gcagttcccc aaggacacca tcaacgagga agtgatcgag   10140
ttcctgagcc cctacttcga gatgcccgac tacaacatcg aaaccgccaa acgcgtgtgc   10200
ggcaacgtgg ccggactgtg cagctggacc aaggccatgg ccagcttctt cagcatcaac   10260
aaagaggtgc tgccctgaa ggccaacctg gtggtgcaga aaaaccggca cctgctggcc   10320
atgcaggacc tgcagaaagc ccaggccag ctggacgaca gcaggccga gctggacgtg   10380
gtgcaggcca gtacgagca ggccatgacc gagaagcaga cccctgga agacgcgag   10440
cggtgcagac acaagatgca gaccgccagc accctgatca gcggactggc cggcgaaaa   10500
gagcggtgga ccgagcagag ccaggaattc gccgcccaga ccaagcggct cgtgggagac   10560
gtgctgtcc accgcctt cctgagctac agcgccgt tcaaccagga attcaggga   10620
ctgctgctga cgactggcg gaaagagatg aaggccagaa agatcccctt cggcaagaac   10680
ctgaacctga gcgagatgct gatcgacgcc ccaccatca gcgagtggaa cctgcaggga   10740
ctgcccaacg acgacctgag catccagaac ggaatcatcg tgaccaaagc cagcagatac   10800
cccctgctga tcgaccccca gacacagggc aagatctgga tcaagaacaa agagagccgg   10860
aacgagctgc agatcaccag cctgaaccac aagtacttcc ggaaccacct ggaagacagc   10920
```

-continued

```
ctgagcctgg gcaggccact gctgatcgag gacgtgggcg aggaactgga cccagccctg  10980
gacaacgtgc tggaacggaa cttcatcaag accggcagca ccttcaaagt gaaagtgggc  11040
gacaaagaag tggacgtgct ggacggcttc cggctgtaca tcaccaccaa gctgcccaac  11100
cccgcctaca ccccccgagat cagcgcccgg accagcatca tcgacttcac cgtgacaatg  11160
aagggactgg aagaccagct gctgggacgc gtgatcctga cagagaagca ggaactggaa  11220
aaagaacgga cccacctgat ggaagacgtg accgccaaca agcggcggat gaaggaactg  11280
gaagacaacc tgctgtacag gctgaccagc cccagggca gctggtgga agacgagagc  11340
ctgatcgtgt gctgagcaa caccaagcgg accgcagagg aagtgaccca gaagctggaa  11400
atcagcgccg agacagaggt gcagatcaac agcgccaaga agagtaccg gcccgtgtgc  11460
acccggggaa gcatcctgta cttcctgatc accgagatgc ggctcgtgaa cgagatgtac  11520
cagaccagcc tgcggcagtt cctgggcctg ttcgacctga gcctggccag aagcgtgaag  11580
agccccatca ccagcaagag aatcgccaac atcatcgagc acatgaccta cgaggtgtac  11640
aaatacgccg ccagaggcct gtacgaggaa cacaagttcc tgttcacact gctgctgacc  11700
ctgaagatcg acatccagcg gaacagagtg aagcacgaag agttcctgac actgatcaag  11760
gggggagcca gcctggacct gaaggcctgc ccccccaagc ccagcaagtg gatcctggac  11820
atcacctggc tgaacctggt ggaactgagc aagctgagac agttcagcga cgtgctggac  11880
cagatcagcc gcaacgagaa gatgtggaag atctggttcg acaaagagaa ccccgaggaa  11940
gaacccctgc ccaacgccta cgacaagagc ctggactgct tccggcggct gctgctgatc  12000
agaagctggt gccccgaccg gacaatcgcc caggcccgca agtacatcgt ggacagcatg  12060
ggagagaagt acgccgaggg cgtgatcctg gacctggaaa agaccgggga ggaaagcgac  12120
cccagaaccc ccctgatctg cctgctgagc atgggcagcg accccaccga cagcatcatc  12180
gccctgggca agagactgaa gatcgagaca agatacgtgg aggccaggaa gtgcacgcca  12240
gtgcacgcca gaaagctgct gcagcagacc atggccaacg gcggctgggc cctgctgcag  12300
aactgccacc tggggctgga cttcatggac gaactgatgg acatcatcat cgagacagag  12360
ctggtgcacg acgccttcag actgtggatg accaccgagg cccacaagca gttccccatc  12420
accctgctgc agatgagcat caagttcgcc aacgacccc ccagggact gagagccgac  12480
ctgaagagaa cctacagcgg cgtgagccag gacctgctgg acgtgagcag cggcagccag  12540
tggaagccca tgctgtacgc cgtggcattc ctgcacagca ccgtgcagga acggcggaag  12600
ttcggcgccc tgggatggaa catccctac gagttcaacc aggccgactt caacgccacc  12660
gtgcagttca tccagaacca cctggacgac atggacgtga ggaaaggggt gagctggaca  12720
accatccggt acatgatcgg agagatccag tacggcggca gagtgaccga cgactacgac  12780
aagaggctgc tgaacacctt cgccaaagtg tggttcagcg agaacatgtt cggccccgac  12840
ttcagcttct accagggcta caacatcccc aagtgcagca ccgtgacaa ctacctgcag  12900
tacatccaga gcctgcccgc ctacgacagc cccgaggtgt tcggactgca ccccaacgcc  12960
gacatcacct accagagcaa actggcccaag gacgtgctgg acaccatcct gggcatccag  13020
cccaaggaca ccagcggcgg aggcgacgaa cccgggaag cagtggtggc cagactggcc  13080
gacgacatgc tggaaaagct gccccccgac tacgtgccct cgaagtgaa agaacgcctg  13140
cagaagatgg gccccttcca gcccatgaac atcttcctga ggcaggaaat cgaccggatg  13200
cagcggctgc tgagcctcgt gcggagcaca ctgaccgagc tgaaactgac catcgacgc  13260
accatcatca tgagcgagaa cctgcgggac gcactggact gcatgttcga cgccagaatc  13320
cccgcatggt ggaaaaagc cagctggatc agcagcaccc tgggcttctg gttcaccgaa  13380
ctgatcgaga gaaacagcca gttcaccagc tgggtgttca acggcagacc ccactgcttc  13440
tggatgacgg gcttcttcaa cccacaaggc ttcctgacaa caatgcgcca ggaaatcacc  13500
agagccaaca agggctgggc cctggacaac atggtgctgt gcaacgaagt gaccaagtgg  13560
atgaaggacg acatcagcgc ccccccacca gagggcgtgt acgtgtacgg cctgtacctg  13620
gaaggcgccg gatgggacaa gagaaacatg aagctgatcg agagcaagcc caaggtgctg  13680
ttcgagctga tgcccgtgat caggatctac gccgagaaca acaccctgga ggaccccgtg  13740
ttctacagct gccccatcta caagaaaccc gtgcgcaccg acctgaacta catcgccgcc  13800
gtggacctga ggacagccca gacacccgag cactgggtgc tgagaggcgt ggcactgctg  13860
tgcgacgtga agtga                                                  13875
```

SEQ ID NO: 18   moltype = DNA length = 13875
FEATURE     Location/Qualifiers
misc_feature   1..13875
          note = Description of Artificial Sequence: Synthetic
         polynucleotide
source      1..13875
         mol_type = other DNA
         organism = synthetic construct
SEQUENCE: 18

```
atgttcagaa tcggcagacg gcagctgtgg aagcacagcg tgaccagagt gctgacccag    60
cggctgaagg gcgagaaaga ggccaagaga gccctgctgg acgcccggca caattacctg   120
tttgccatcg tggccagctg cctggacctg aacaagaccg aggtggaaga tgccatcctg   180
gaaggcaacc agatcgagcg gatcgaccag ctgtttgcc tggggcgact gccggcacctg   240
atgttctatt atcaagacgt ggaagaggcc gagacaggcc agctgggatc tctgggcgga   300
gtgaatctgg tgtccggcaa gatcaagaaa cccaaggtgt tcgtgaccga gggcaacgac   360
gtggccctga caggcgtgtg cgtgttcttc atcagaaccg accccagcaa ggccatcacc   420
cccgacaaca tccaccagga agtgtccttc aacatgctgg atgccgccga tggcggcaca   480
ctgaattctg tgcggagac gctgagcgac atcttcatcc cgccctgag agccacatct   540
cacggctggg gagagctgga aggactgcag gacgccgcca atatccggca ggaatttctg   600
agcagcctgg aaggattcgt gaacgtgctg tctggcgccc aggaaagcct gaagaaaaa   660
gtgaacctgc ggaagtgcga tatcctgaa ctgaaaccc tgaagagcc caccgactac   720
ctgaccctgc caacaaccc tgagacactg gcaagatcg aggactgcat gaaagtgtgg   780
atcaagcgaa ccgaacaggt gctggcgag agcaaccgga tcctgaaga agccgacgac   840
gtgggccaa gagccgagct ggaacactgg aagaagcggc tgagcaagtt caactacctg   900
ctggaacagc tgaagtcccc cgacgtgaag gccgtgctgg ctgtgctggc agccgccaag   960
agcaaactgc tgaaacctg gcgcgagatg gacatccgga tcaccgacgc caccaacgag  1020
gccaaggaca acgtgaagta cctgtacacc ctggaaaagt gctgcgaccc cctgtacagc  1080
agcgaccctc tgagcatgat ggacgccatc cctaccctga tcaacgccat caagatgatc  1140
```

```
tacagcatca gccactacta caacaccagc gagaagatca ccagcctgtt cgtgaaagtg   1200
accaatcaga tcatcagcgc ctgcaaggcc tacatcacca acaacggcac cgccagcatc   1260
tggaaccagc cccaggatgt ggtggaagag aagatcctgt ctgccatcaa gctgaagcag   1320
gaataccagc tgtgttttca caagaccaag cagaagctga acagaaccc caacgccaag    1380
cagttcgact tcagcgagat gtatatcttc ggcaagttcg agacattcca ccggcggctg   1440
gccaagatca tcgacatctt taccaccctg aaaacataca gcgtgctgca ggacagcacc   1500
atcgagggcc tggaagatat ggccaccaag taccagggca ttgtggccac catcaagaag   1560
aaagagtaca acttcctgga ccagcgcaag atggacttcg accaggacta cgaggaattc   1620
tgcaagcaga caaacgacct gcacaacgag ctgcgcaagt ttatggacgt gaccttcgcc   1680
aagatccaga acaccaacca ggccctgcgg atgctgaaga gtttgagag actgaacatc    1740
cccaacctgg gcatcgacga taagtaccag ctgatcctgg aaaactacgg cgccgacatc   1800
gacatgatca gcaagctgta cacaaagcag aagtacgacc cccccctggc ccggaatcag   1860
cctcctatcg ccggcaaaat cctgtgggct agacagctgt tcaccggat ccagcagccc    1920
atgcagctgt tccagcagca ccctgccgtg ctgagcaccg ccgaggccaa acccatcatc   1980
cggtcctaca accggatggc caaggtgctg ctggaattcg aggtgctgtt ccaccgggcc   2040
tggctgcggc agatcgaaga gattcacgtg ggactggaag ccagcctgct cgtgaaggct   2100
cctggaaccg gcgagctgtt tgtgaacttc gaccccaga tcctgatcct gttccgggaa    2160
accgagtgca tggcccagat ggggctggaa gtgtctcctc tggccacctc cctgttccag   2220
aagcgggacc ggtacaagcg gaacttcagc aacatgaaga tgatgctggc tgagtaccag   2280
cgcgtgaagt ccaagatccc cgctgccatc gagcagctga tcgtgcctca cctgccaaa    2340
gtggacgagg ccctgcagcc aggactggcc gctctgacat ggaccagcct gaacatcgag   2400
gcctatctgg aaaacacatt cgccaaaatc aaggatctgc aactgctgct ggaccgcctg   2460
aacgacctga tcgagttccg gatcgacgcc attctggaag atgtccag caccccctg      2520
tgtcagctgc ccaggaaga acccctgacc tgcaagagt tcctgcagat gaccaaggac     2580
ctgtgcgtga acggcgccca gattctgcac ttcaagtcca gcctggtgga agaagccgtg   2640
aacgagctgc tgaatatgct gctggatgtg gaagtgctga gcgaggaaga gtccgagaag   2700
atctccaacg agaacagcgt gaactacaag aacgagtcca gcgccaagcg ggaagagggc   2760
aacttcgaca ccctgaccag ctccatcaat gccagagcca acgccctgct gctgaccacc   2820
gtgacccgga gaaaaaaga aaccgagatg ctgggcgaag aggctagaga gctgctgtcc    2880
cacttcaacc accagaacat ggatgccctg ctgaaagtga cacggaatac cctgaagcc    2940
atccggaagc ggatccacag cagccacacc atcaacttcc gggacagcaa cagcgccagc   3000
aatatgaagc agaacagcct gcccatcttc cgggcctccg tgacactggc catccccaat   3060
atcgtgatgc ccctgctct ggaagatgtg cagcagacac tgaacaaggc cgtggaatgc    3120
atcatctccg tgcccaaggg cgtgcggcag tggtctagcg aactgctgct caagaagaag   3180
atccaggaac ggaaaatggc cgccctgcag tctaacgagg acagcgactc cgacgtggaa   3240
atgggcgaga atgagctgca ggatacactg gaaatcgcct ctgtgaatct gcccatcccc   3300
gtgcagacca gaactacta taagaacgtg tccgaaaaca agaaatcgt gaagctggtg     3360
tctgtgctgt ccaccatcat caacagcacc aagaagaag tgatcacctc catggactgc    3420
ttcaagcggt acaaccacat ctggcagaag ggcaaagaag aggccattaa gaccttcatc   3480
acccagagcc ccctgctgtc cgagttcgag tctcagatcc tgtacttcca gaacctggaa   3540
caggaaatca acgccgagcc cgagtacgtg tgtgtgggct ctatcgccct gtataccgcc   3600
gacctgaagt tcgccctgac cgccgagaca aaggcctgga tggtcgtgat cggccggcac   3660
tgcaacaaaa agtacagatc cgagatgaaa aacatcttta tgctgattga ggaattcaa    3720
aagaaactga accggcccat taaggacctg gacgacatca gaatcgccat ggccgcactg   3780
aaaagagatca gagaggaaca gatcagcatc gacttccaag tgggcccat cgaggaaagc   3840
tacgctctgc tgaacagata cggactgctg atcgcccggg aagagatcga caaggtggac   3900
acctgcact acgcctggga gaagctgcg gctagagccg gaagtgca gaacaaactg       3960
gtgtctctgc agcccagctt taagaaagaa ctgatctccg ccgtggaagt gtttctgcag   4020
gactgccacc agttctacct ggactacgac ctgaacggcc ccatgcctc tggcctgaaa    4080
cctcaggaag cctccgaccg gctgattatg tttcagaacc agttcgacaa tatctaccgg   4140
aagtacatca cctacacagg cggcgaggaa ctgttcgcca tgcctgccac acagtacccc   4200
cagctgctgg aaatcaagaa gcagctgaac ctgctgcaga gatctacac cctgtacaac   4260
tccgtgatcg agacagtgaa cagctactac gacatcctgt ggagcgaagt gaacattgag   4320
aagattaaca tgaactgct ggaatttcag accggtgcc ggaagctgcc cagagcactg     4380
aaggattggc aggcctttct ggatctgaaa aaatcatcg acgacttctc cgagtgctgc   4440
cctctgctgg agtacatggc ctccaaggcc atgatgaac ggcactggga gagaataccc    4500
acactgaccg gccacagcct ggacgtgggc aacgagagct tcaagctgcg gaacatcatg   4560
gaagcccac tgctgaagta caagaggaa atcgaggaca tctgtatcag cgccgtgaaa     4620
gagcgggata tcgagcagaa actgaaacaa gtgatcaacg agtgggacaa caagaccttt   4680
accttcggca gcttcaagac cagaggcgag ctgctgctgc ggggcgatag cacctctgag   4740
atcattgcca acatggaaga tagcctgatg ctgctgggct ccctgctgag caaccggtat   4800
aacatgcct tcaaggctca gattcagaaa tgggtgcagt acctgagcaa ctccaccgac    4860
atcatcgagt cctggatgac cgtgcagaac ctgtggatct acctggaagc cgtgttcgtg   4920
ggcggcaca ttgccaagca gctgcccaaa gaggctaag ggttctccaa catcgacaag    4980
agctgggtca agatcatgac cagagcccac gaggtgccca gcgtggtgca gtgctgtgtg   5040
ggcgacgaaa cactgggaca gctgctgcct catctgctgg accagctgga aatctgccag   5100
aagtccctga ccgctacct ggaaagaaa cggctgtgtt tcccccggtt cttcttcgtg     5160
tccgaccccg ccctgctgga aattctgggc caggccagcg actcacacac aattcaggcc   5220
catctgctga atgtgttcga taacatcaag agctgaagc tccacgagaa aatctacgac    5280
cggatcctga gcatcagctc ccaggaaggc gagacaatcg agctgcaa gcctgtgatg    5340
gccgagggaa acgtggaagt gtggctgaac agcctgctgg aagagtccca gagcagcctg   5400
cacctcgtga tcagacaggc cgctgccaac atccaggaaa ccggctttca gctgaccgag   5460
ttcctgtcca gcttccagc acaagtggga ctgctgggca tccagatgat ttggaccaga   5520
gactccgaag aggccctgag aaacgccaag ttcgataaga aattatgca gaaaacaaat    5580
caggcatttc tggaactgct gaacaccctg atcgacgtga ccaccgggga cctgagcagc   5640
accgagagag tgaagtacga gacactgatc accatccacg tgcaccagcg ggacatcttc   5700
gacgacctgt gccacatgca catcaagtct cccatggatt tcgagtggct gaagcagtgc   5760
aggttctact tcaacgagga ctccgacaag atgatgatcc acatcaccga tgtggccttt   5820
atctatcaga atgagttcct gggctgtacc gatcgcctc tgattacccc cctgaccgac   5880
```

```
cggtgttaca tcacactggc ccaggcactg ggcatgtcta tgggaggcgc accagcagga    5940
cctgccggca caggcaagac cgaaaccacc aaggacatgg gacgctgcct gggcaaatac    6000
gtggtggtgt tcaactgcag cgaccagatg gatttccggg gcctgggccg gatctttaag    6060
ggcctggcac agagcggaag ctggggctgc ttcgacgagt tcaacagaat cgacctgccc    6120
gtgctgtccg tggccgcaca gcagatctcc atcatcctga catgcaaaaa agagcacaag    6180
aagtccttca tcttcaccga cggcgacaat gtgaccatga accccgagtt tggcctgttc    6240
ctgacaatga accctggcta cgccggacgg caggaactgc ccgagaacct gaagatcaac    6300
tttcggagtg tggctatgat ggtgcccgac cggcagatca ttatcagagt gaaactggcc    6360
tcctgcggct tcatcgacaa cgtggtgctg gctcggaagt tcttcacact gtacaagctg    6420
tgcgaagaac agctgagtaa acaggtgcac tacgacttcg gcctgaggaa catcctgagc    6480
gtgctgagaa ctctgggagc cgctaagcgg gccaaccccc tggataccga gagcacaatc    6540
gtgatgcggt tgctgcggga catgaacctg tccaagctga tcgatgagga cgagcccctg    6600
tttctgtctc tgatcgagga tctgtttccc aacattctgc tggataaggc cggctacccc    6660
gaactggaag ctgctatcag cagacaggtg gaagaggctg gcctgatcaa ccaccccccc    6720
tggaaactga aagtgatcca gctgttcgag acacagcgcg tgcggcacgg catgatgaca    6780
ctgggaccta gcgagccgg caagaccacc tgtatccaca cactgatgcg ggccatgacc    6840
gattgcggca agccccaccg cgagatgcgg atgaacccca aggccattac cgcccctcag    6900
atgttcggca gactggacgt ggccaccaac gactggaccg acggcatctt cagcaccctg    6960
tggcgcaaga ccctgcgggc caagaagggc gagcacatct ggatcatcct ggacggcccc    7020
gtggacgcca tctggattga gaacctgaac agcgtgctgg acgacaacaa gacactgacc    7080
ctggccaacg gcgaccggat ccccatggcc cccaactgca gatcatctt cgagcccac     7140
aacatcgaca acgccagccc tgccaccgtg tccagaaacg gcatggtgtt catgagcagc    7200
agcatcctgg attggagccc tatcctgaa ggcttcctga agaagcgag ccccaggaa     7260
gccgagatcc tgagacagct gtacaccgag agcttcccg acctgtaccg gttctgcatc    7320
cagaatctgg agtacaagat ggaagtgctg gaagcctttg tgatcaccca gagcatcaac    7380
atgctgcagg gcctgatccc cctgaaagaa cagggcgagg aagtgtccca ggcccacctg    7440
ggcagactgt tcgtgtttgc cctgctgtgg agcgctggcg ccgctctgga actggatgga    7500
aggcggagac tggaactgtg gctgcgggag agacctaccg gcaccctgga actgcctcca    7560
ccagctggac ctggcgacac cgccttcgat tactacgtgg cccctgacgg cacctggacc    7620
cactggaata cccggaccca ggaatacctg taccccagcg acaccaccca cgagtacgg    7680
tctatcctgg tgcccaacgt ggacaacgtg cggaccgact tcctgatcca gacaatcgcc    7740
aagcagggaa aggccgtgct gctgatcgc gagcagggca cagccaagac cgtgatcatc    7800
aagggcttta tgtctaagta cgaccccgag tgccacatga tcaagagcct gaacttcagc    7860
tccgccacca ccccactgat gttccagcgg accatcgaga gctatgtgga caagcggatg    7920
ggcaccacct acggccctcc agccggcaag aaaatgaccg tgttcatcga cgacgtgaac    7980
atgcccatca tcaacgagtg gggcgaccaa gtgaccaacg agatcgtgcg gcagctgatg    8040
gaacagaacg gcttctacaa cctggaaaag cccggcgagt tcacctctat cgtggacatc    8100
cagttctctg ccgccatgat ccaccctggc ggcggaagaa acgacatccc ccagcggctg    8160
aagcggcagt tcagcatctt caactgcacc gtgcccaagcg aggcagaagt gacaagatc    8220
tttggcgtga tcggcgtggg ccactactgc acccagagag gcttcagcga ggaagtgcgg    8280
gacagcgtga ccaagctggt gcctctgaca agacggctgt ggcagatgac caagatcaag    8340
atgctgccca ccccgccaa gttccactac gtgttcaacc tgcgggacct gagcagagtg    8400
tggcagggaa tgctgaacac caccagcgaa gtgatcaaag agcccaacga cctgctgaga    8460
ctgtggaagc acgagtgcaa gagagtgatc gccgaccggt tcaccgtgtc tagcgacgtg    8520
acatggttcg acaaggccct ggtgtccctg tggaagagg aattcggcga agagaagaaa    8580
ctgctggtgg actgcggcat cgataccac ttcgtggact tcctgcgcga cgcccctgaa    8640
gcctggcg agacaagtga agaggccgac gccgagaccc caagatcta cgagcccatc    8700
gagtccttca gccatctgaa agaaaggctg aatatgttcc tgcagctgta taacgagtcc    8760
atccggggag ccggcatgga tatggtgttc tttgccgacg ccatggtgca cctcgtgaag    8820
atcagcagag tgatccggac ccccccaggc aacgctctgc tcgtgggagt gggaggctct    8880
ggcaagcaga gcctgaccag actggcggcc tttatcgcg gctacgtgtc cttccagatg    8940
accctgaccc ggtcctacaa caccagcaac ctgatggaag atctgaaggt gctgtaccgg    9000
acagccggcc agcagggaa gggcatcacc ttcatcttca ccgacaatga gatcaaggac    9060
gagtctttcc tggagtatat gaacaatgtg ctgagcagcg gcgaggtgtc caacctgttc    9120
gcccggacg agatcgacga gattaacagc gacctggccc ccgtgatgaa gaaagaattc    9180
ccccggtgcc tgcccacaaa cgagaacctg cacgactact tcatgtccag agtgcggcag    9240
aatctgcaca tcgtgctgtg cttcagcccc gtgggcgaga gttcagaaa ccgggccctg    9300
aagttccccg ccctgatcag cggctgcacc atcgactggt tcagcggtg gcctaaggat    9360
gccctggtgg ccgtgtccga gcactttctg accagctacg acatcgactg cagcctggaa    9420
atcaagaaag aggtggtgca gtgcatgggc agcttccgg acggcgtggc cgagaaatgc    9480
gtggactact tccagcggtt ccggcggagc acccacgtga cccctaagag ctacctgagc    9540
ttcatccagg gctacaagtt catctacggc gagaagcacg tggaagtgcg cacactggcc    9600
aacccggatg acaccggcct ggaaaaactg aagaggcct ccgagagcgt ggccgccctg    9660
agcaaagaac tggaagcaa agaaaaagaa ctgcagttgg ccaacgataa ggccgacatg    9720
gtgctgaaag aagtgaccat gaaggcccag gccgccgaga aagtgaaagc cgaggtgcag    9780
aaagtgaagg accgggccca ggccatcgtg gactccatca gcaaggacaa ggccattgcc    9840
gaggaaaagc tggaagcagc caagcccgcc ctggaagagg cagaagctgc tctgcagacc    9900
atccggcct ccgatattgc cacagtgcgg accctggaa ggccccctca cctgatcatg    9960
cggatcatgg actgtgtgct gctgctgttc cagagaaagg tgtccgccgt gaagtcgac     10020
ctggaaaaat cctgcaccat gcctagctgg caggaatccc tgaagctgat gaccgccggc    10080
aacttcctgc agaacctgca gcagttcccc aaggacacca tcaatgagga agtgatcgag    10140
ttcctgagcc cctacttcga gatgcccgac tacaatatcg aaaccgccaa cgcgtgtgc    10200
ggcaacgtgc ccggactgtg ctcttggacc aaggctatgc tagcttctt tagcattaac    10260
aaagagcggt tgcctctgaa ggccaacctg gtggtgcagg aaaaccggca tgctgctggcc    10320
atgcaggacc tgcagaaagc ccaggccgag ctgacgata agcaggctga gctggatgtg    10380
gtgcaggcca gtacgagca ggccatgacc gagaagcaga cccctgctgga gatgcgagag    10440
cggtgcagac acaagatgca gaccgccagc accctgatct ctggactggc cggcgaaaaa    10500
gagcggtgga ccgagcagtc ccaggaattc gccgcccaga ccaagcggct cgtgggagat    10560
gtgctgctgg ccaccgcctt tctgagctac agcggccct tcaatcagga attcaggac      10620
```

```
ctgctgctga acgactggcg gaaagagatg aaggccagaa agatcccctt cggcaagaat  10680
ctgaacctga gcgagatgct gatcgacgcc cccaccatct ccgagtggaa tctgcaggga  10740
ctgcccaacg atgacctgtc catccagaac ggaatcatcg tgaccaaagc ctccagatac  10800
cccctgctga ttgaccccca gacacagggc aagatttgga tcaagaacaa agagagccgg  10860
aacggctgc agatcaccag cctgaaccac aagtacttcc ggaaccacct ggaagatagc  10920
ctgagcctgg gcaggccact gctgatcgag gatgtgggcg aggaactgga cccagccctg  10980
gataacgtgc tggaacggaa cttcatcaag accggctcca ccttcaaagt gaaagtgggc  11040
gacaaagaag tggacgtgct ggatggcttc cggctgtaca tcaccaccaa gctgcctaac  11100
cccgcctaca cccctgagat cagcgcccgg accagcatca tcgacttcac cgtgacaatg  11160
aagggactgg aagatcagct gctgggacgc gtgatcctga cagagaagca ggaactggaa  11220
aaagaacgga cccatctgat ggaagatgtg accgccaaca agcggcggat gaaggaactg  11280
gaagataacc tgctgtacag gctgaccagc acccagggca gtctggtgga agatgagagc  11340
ctgatcgtgg tgctgtccaa caccaagcgg accgcagagg aagtgaccca gaagctggaa  11400
atcagcgccg agacagaggt gcagatcaac agcgccaaga agtaccg gcctgtgcc  11460
acccggggat ccatcctgta ctttctgatc accgagatgc ggctcgtgaa cgagatgtac  11520
cagaccagcc tgcggcagtt cctgggcctg ttcgatctgt ccctggccag aagcgtgaag  11580
tcccccatca ccagcaagag aatcgccaac atcatcgagc acatgaccta cgaggtgtac  11640
aaatacgccg ccagaggcct gtacgaggaa cacaagtttc tgttcacact gctgctgacc  11700
ctgaagatcg atatccagcg gaacagagtg aagcacgaag agtttctgac actgatcaag  11760
gggggagcct ccctggacct gaaggcctgt cctcccaagc ccagcaagtg gatcctggac  11820
atcacctggc tgaatctggt ggaactgagc aagctgagac agttctccga tgtgctggac  11880
cagatcagcc gcaacagaa gatgtggaag atttggtttg acaaagagaa ccccgaggaa  11940
gaacccctgc ctaacgccta cgataagagc ctggactgct tccggcggct gctgctgatt  12000
agaagctggt gtcccgaccg gacaatcgcc caggcccgca agtacatcgt ggatagcatg  12060
ggagagaagt acgccgaggg cgtgatcctg gacctgaaaa agacctggga ggaaagcgac  12120
cccagaaccc ccctgatctg cctgctgagc atgggctccg accccaccga cagcattatc  12180
gccctgggca agagactgaa gattgagaca agatacgtgt ccatgggcca gggccaggaa  12240
gtgcacgcta gaaagctgct gcagcagact atggccaatg cggctgggc cctgctgcag  12300
aattgtcacc tggggctgga cttcatggac gaactgatgg acatcatcat tgagacagag  12360
ctggtgcaca acgccttcag actgtggatg accaccgagg cccataagca gttccccatt  12420
accctgctgc agatgagcat caagttcgcc aacgacccc ctcagggact gagagccggc  12480
ctgaagagaa cctactccgg cgtgtcacag gatctgctgg acgtgtcctc tggcagccag  12540
tggaagccta tgctgtacgc cgtggcattc ctgcacagca ccgtgcagga acggcggaag  12600
tttggcgccc tgggatggaa catccctac gagtttaacc aggccgactt caacgccact  12660
gtgcagttta tccagaacca tctgacgac atggacgtga agaaggggt gtcctggaca  12720
accatccggt acatgatcgg agagatccag tacgccggca gagtgaccga cgactacgac  12780
aagaggctgc tgaataccct cgccaaagtg tggttctccg agaacatgtt ggccccgac  12840
ttcagcttttt accagggcta taacatcccc aagtgctcca ccgtggataa ctacctgcag  12900
tacatccaga gcctgccgc ctacgacagc cctgaggtgt tcggactgca cccaacgcc  12960
gatatcacct accagagcaa actgccaag gatgtgctgg ataccatcct gggcatccag  13020
cccaaggata ccagtggcgg aggcgacgaa acccgggaag cagtggtggc tagactggcc  13080
gacgacatgc tggaaaagct gcccccgac tacgtgccct ttgaagtgaa agaacgcctg  13140
cagaagatgg gccccttcca gcctatgaac atcttcctga ggcaggaaat cgaccgggaa  13200
cagcgggtgc tgtctctcgt gcggagcaca ctgaccgagc tgaaactggc tatcgacggc  13260
accatcatca tgagcgagaa tctgcgggat gcactggact gcatgttcga cgccagaatc  13320
cccgcatggt ggaaaaggc cagctggatc agctctaccc tgggcttctg gttcaccgaa  13380
ctgatcgaga gaaacagcca gtttaccagc tgggtgttca acggcagacc tcactgcttc  13440
tggatgaccg gcttcttcaa tccacaaggc tttctgacag caatgcgcca ggaaatcacc  13500
agagccaaca agggctgggc tctggacaat atggtgctgt gtaacgaagt gactaagtgg  13560
atgaaggacg acatcagcgc ccctcccaca gagggcgtgt acgtgtacgg cctgtacctg  13620
gaaggcgccg gatgggacaa gagaaacatg aagctgatcg agagcaagcc caaggtgcta  13680
ttcgagctga tgcccgtgat caggatctat gccgagaaca acacccctgag gaccccgg  13740
ttctacagct gcccccatcta caagaaaccc gtgcgcaccg acctgaacta tatcgccgcc  13800
gtggacctga ggacagccca gacacctgag cattgggtgc tgagaggcgt ggcactgctg  13860
tgcgacgtga agtga                                                  13875
```

SEQ ID NO: 19          moltype = RNA    length = 10
FEATURE                Location/Qualifiers
misc_feature           1..10
                       note = Description of Artificial Sequence: Synthetic
                       oligonucleotide
source                 1..10
                       mol_type = other RNA
                       organism = synthetic construct
SEQUENCE: 19
gccrccatgg                                                                10

SEQ ID NO: 20          moltype = DNA    length = 11
FEATURE                Location/Qualifiers
misc_feature           1..11
                       note = Description of Artificial Sequence: Synthetic
                       oligonucleotide
source                 1..11
                       mol_type = other DNA
                       organism = synthetic construct
SEQUENCE: 20
gaattctgca g                                                              11